US010081815B2

(12) United States Patent
Fabijanski et al.

(10) Patent No.: US 10,081,815 B2
(45) Date of Patent: *Sep. 25, 2018

(54) PRODUCTION OF MODIFIED FATTY ACIDS IN PLANTS THROUGH RDNA TARGETED INTEGRATION OF HETEROLOGOUS GENES

(71) Applicant: Agrisoma Biosciences Inc., Gatineau (CA)

(72) Inventors: Steven Fabijanski, Orleans (CA); Michael Lindenbaum, Beaconsfield (CA); Ping Fu, Saskatoon (CA); Elizabeth-France Marillia, Asquith (CA)

(73) Assignee: Agrisoma Biosciences Inc., Ottawa (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/256,244

(22) Filed: Sep. 2, 2016

(65) Prior Publication Data
US 2017/0051299 A1 Feb. 23, 2017

Related U.S. Application Data

(63) Continuation of application No. 14/024,220, filed on Sep. 11, 2013, now abandoned, which is a continuation of application No. 12/571,012, filed on Sep. 30, 2009, now Pat. No. 8,546,645.

(60) Provisional application No. 61/102,509, filed on Oct. 3, 2008.

(51) Int. Cl.
*C12N 15/82* (2006.01)
*C11B 1/10* (2006.01)
*C11C 3/04* (2006.01)
*C12N 9/10* (2006.01)
*A01H 4/00* (2006.01)
*C12N 15/87* (2006.01)
*C12Q 1/6895* (2018.01)

(52) U.S. Cl.
CPC ........ *C12N 15/8247* (2013.01); *A01H 4/008* (2013.01); *C11B 1/10* (2013.01); *C11C 3/04* (2013.01); *C12N 9/1029* (2013.01); *C12N 15/87* (2013.01); *C12Q 1/6895* (2013.01); *C12Q 2600/13* (2013.01); *Y02E 50/13* (2013.01)

(58) Field of Classification Search
None
See application file for complete search history.

(56) References Cited

U.S. PATENT DOCUMENTS

| 4,683,195 A | 7/1987 | Mullis |
| 4,683,202 A | 7/1987 | Mullis |
| 4,940,838 A | 7/1990 | Schilperoort |
| 4,965,188 A | 10/1990 | Mullis |
| 5,384,253 A | 1/1995 | Krzyzek |
| 5,445,947 A | 8/1995 | Metz |
| 5,501,967 A | 3/1996 | Offringa |
| 5,658,772 A | 8/1997 | Odell |
| 5,824,858 A | 10/1998 | Davies |
| 5,929,301 A | 7/1999 | Baszcynski |
| 6,077,697 A | 6/2000 | Hadlaczky |
| 6,445,315 B1 | 9/2002 | den Breejen |
| 8,546,645 B2* | 10/2013 | Fabijanski ............... C11B 1/10 435/419 |
| 2006/0143732 A1 | 6/2006 | Perez |
| 2007/0204370 A1 | 8/2007 | Mietkiewska |
| 2010/0221720 A1 | 9/2010 | Perez |

FOREIGN PATENT DOCUMENTS

| CA | 2 306 053 A1 | 5/1999 |
| EP | 1 414 979 B1 | 9/2007 |
| WO | 91/00920 A2 | 1/1991 |
| WO | 92/06205 A1 | 4/1992 |
| WO | 98/13505 A1 | 4/1998 |
| WO | 2007/042510 A2 | 4/2007 |
| WO | 2008/061334 A1 | 5/2008 |

OTHER PUBLICATIONS

Marcotte, W.R., Jr., et al., "Regulation of a Wheat Promoter by Abscisic Acid in Rice Protoplasts," Nature 335(6189):454-457, Sep. 1988.
Matzke, M., and J.M. Matzke, "RNAi Extends Its Reach," Science 301(5636):1060-1601, Aug. 2003.
Mietkiewska, E., et al., "Seed-Specific Heterologous Expression of a Nasturtium FAE Gene in *Arabidopsis* Results in a Dramatic Increase in the Proportion of Erucic Acid," Plant Physiology 136(1):2665-2675, Sep. 2004.
Millar, A.A., and L. Kunst, "Very-Long-Chain Fatty Acid Biosynthesis Is Controlled Through the Expression and Specificity of the Condensing Enzyme," Plant Journal 12(1):121-131, Jul. 1997.
Pecorino, L.T., and D.C. Lo, "Having a Blast With Gene Transfer," Current Biology 2(1):30-32, Jan. 1992.
Potrykus, I., et al., "Direct Gene Transfer to Cells of a Graminaceous Monocot," Molecular and General Genetics 199(2):183-188, 1985.
Raina S.N., and Y. Mukai, "Detection of a Variable Number of 18S-5.8S-26S and 5S Ribosomal DNA Loci by Fluorescent In Situ Hybridization in Diploid and Tetraploid *Arachis* Species," Genome 42:52-59, 1999.

(Continued)

*Primary Examiner* — Eileen B O Hara
(74) *Attorney, Agent, or Firm* — Christensen O'Connor Johnson Kindness PLLC

(57) ABSTRACT

The present invention relates to transgenic plants comprising a plurality of nucleic acids heterologous to said plant, each of said nucleic acid comprising a coding sequence operably linked to one or more regulatory elements for directing expression of said coding sequence in said plant, said nucleic acid being stably integrated at or adjacent to rDNA sequences, or a seed, organ, tissue, part or cell thereof, or a descendant of said plant, seed, organ, tissue, part or cell; methods of producing the transgenic plants; and methods of producing oil using the transgenic plants.

18 Claims, 37 Drawing Sheets

Specification includes a Sequence Listing.

(56) References Cited

OTHER PUBLICATIONS

Reiss, B., "Homologous Recombination and Gene Targeting in Plant Cells," International Review of Cytology 228:85-139, 2003.
Roeder, R.G., "The Complexities of Eukaryotic Transcription Initiation: Regulation of Preinitiation Complex Assembly," Trends in Biochemical Sciences 16(11):402-408, Nov. 1991.
Rossolini, G.M., et al., "Kluyveromyces lactis rDNA as a Target for Multiple Integration by Homologous Recombination," Gene 119(1):75-81, Sep. 1992.
Sambrook, J., et al., "Analysis of Genomic DNA by Southern Hybridization," in "Molecular Cloning: A Laboratory Manual," 2d ed., Cold Spring Harbor Laboratory, Cold Spring Harbor, N.Y., 1989, vol. 2, Chap. 9, "Analysis and Cloning of Eukaryotic Genomic DNA," pp. 9.31-9.58.
Samoylov, V.M., et al., "A Liquid-Medium-Based Protocol for Rapid Regeneration From Embryogenic Soybean Cultures," Plant Cell Reports 18(1-2):49-54, 1998.
Schock, G., et al., "Glutamine Synthetase From Roots of *Brassica napus*," Plant Physiology 105(2):757-758, Jun. 1994.
Shi, L., et al., "Ribosomal RNA Genes in Soybean and Common Bean: Chromosomal Organization, Expression, and Evolution," Theoretical and Applied Genetics 93(1-2):136-141, Jul. 1996.
Simmonds, D., "Genetic Transformation of Soybean With Biolistics," in J.F. Jackson and H.F. Linskens (eds.), "Molecular Methods of Plant Analysis," 2nd ed., Springer-Verlag, Berlin, 2003, vol. 23, "Genetic Transformation of Plants," Chap. 10, pp. 159-174.
Simmonds, J., et al., "Oxalate Oxidase: A Novel Reporter Gene for Monocot and Dicot Transformations," Molecular Breeding 13(1):79-91, Dec. 2004.
Songstad, D.D., et al., "$AgNO_3$ Increases Type II Callus Production From Immature Embryos of Maize Inbred B73 and Its Derivatives," Plant Cell Reports 9(12):699-702, 1991.
Sorrell, D.A., and A.F. Kolb, "Targeted Modification of Mammalian Genomes," Biotechnology Advances 23(7-8):431-469, Nov. 2005.
Taylor, S.L., et al., "Determination of Oil Content in Oilseeds by Analytical Supercritical Fluid Extraction," Journal of the American Oil Chemists' Society (JAOCS) 70(4):437-439, Apr. 1993.
Voelker, T.A., et al., "Fatty Acid Biosynthesis Redirected to Medium Chains in Transgenic Oilseed Plants," Science 257(5066):72-74, Jul. 1992.
Voelker, T.A., et al., "Genetic Engineering of a Quantitative Trait: Metabolic and Genetic Parameters Influencing the Accumulation of Laurate in Rapeseed," Plant Journal 9(2):229-241, Feb. 1996.
Wagner, E., et al., "Coupling of Adenovirus to Transferrin-Polylysine/DNA Complexes Greatly Enhances Receptor-Mediated Gene Delivery and Expression of Transfected Genes," Proceedings of the National Academy of Sciences of the United States of America (PNAS) 89(13):6099-6103, Jul. 1992.
Wanzenbock, E.-M., et al., "Ribosomal Transcription Units Integrated via T-DNA Transformation Associate With the Nucleolus and Do Not Require Upstream Repeat Sequences for Activity in *Arabidopsis thaliana*," Plant Journal 11(5):1007-1016, May 1997.
Wong, T.-K., and E. Neumann, "Electric Field Mediated Gene Transfer," Biochemical and Biophysical Research Communications 107(2):584-587, Jul. 1982.
Xu, J., et al., "Cloning and Characterization of an Acyl-CoA-Dependent Diacylglycerol Acyltransferase 1 (DGAT1) Gene From *Tropaeolum majus*, and a Study of the Functional Motifs of the DGAT Protein Using Site-Directed Mutagenesis to Modify Enzyme Activity and Oil Content," Plant Biotechnology Journal 6(8):799-818, Oct. 2008.
Zatloukal, K., et al., "Transferrinfection: A Highly Efficient Way to Express Gene Constructs in Eukaryotic Cells," Annals of the New York Academy of Sciences 660(1):136-153, Oct. 1992.
Zou, J., et al., "Modification of Seed Oil Content and Acyl Composition in the *Brassicaceae* by Expression of a Yeast sn-2 Acyltransferase Gene," Plant Cell 9(6):909-923, Jun. 1997.
Extended European Search Report dated May 8, 2012, issued in corresponding European Application No. 09817129.1, filed Sep. 30, 2009, 6 pages.
European Examination Report dated Aug. 31, 2015, issued in corresponding European Application No. EP 09817129.1, filed Sep. 30, 2009, 5 pages.
Nath, U.K., "Increasing Erucic Acid Content in the Seed Oil of Rapeseed (*Brassica napus* L.) by Combining Selection for Natural Variation and Transgenic Approaches," doctoral dissertation, Georg-August-University, Gottingen, Germany, Jan. 2008.
Agrawal, N., et al., "RNA Interference: Biology, Mechanism, and Applications," Microbiology and Molecular Biology Reviews 67(4):657-685, Dec. 2003.
Armstrong, C.L., and C.E. Green, "Establishment and Maintenance of Friable, Embryogenic Maize Callus and the Involvement of L-Proline," Planta 164(2):207-214, May 1985.
Bailey, M.A., et al., "Genotype Effects on Proliferative Embryogenesis and Plant Regeneration of Soybean," In Vitro Cellular & Developmental Biology—Plant 29P(3):102-108, Jul. 1993.
Bernerth, R., and M. Frentzen, "Utilization of Erucoyl-CoA by Acyltransferases From Developing Seeds of *Brassica napus* (L.) Involved in Triacylglycerol Biosynthesis," Plant Science 67(1):21-28, Jan. 1990.
Blackwood, E.M., and J.T. Kadonaga, "Going the Distance: A Current View of Enhancer Action," Science 281(5373):60-63, Jul. 1998.
Borisjuk, N., et al., "Tobacco Ribosomal DNA Spacer Element Stimulates Amplification and Expression of Heterologous Genes," Nature Biotechnology 18(12):1303-1306, Dec. 2000.
Britten, R.J., et al., "Analysis of Repeating DNA Sequences by Reassociation," Methods in Enzymology 29E:363-406,1974.
Cao, Y.-Z., et al., "Lysophosphatidate Acyltransferase in the Microsomes From Maturing Seeds of Meadowfoam (*Limnanthes alba*)," Plant Physiology 94(3):1199-1206, Nov. 1990.
Capecchi, M.R., "High Efficiency Transformation by Direct Microinjection of DNA Into Cultured Mammalian Cells," Cell 22(2):479-488, Nov. 1980.
Clapp, D.W., "Somatic Gene Therapy Into Hematopoietic Cells: Current Status and Future Implications," Clinics in Perinatology 20(1):155-168, Mar. 1993.
Curiel, D.T., et al., "Adenovirus Enhancement of Transferrin-Polylysine-Mediated Gene Delivery," Proceedings of the National Academy of Sciences of the United States of America (PNAS) 88(19):8850-8854, Oct. 1991.
Curiel, D.T., et al., "High-Efficiency Gene Transfer Mediated by Adenovirus Coupled to DNA-Polylysine Complexes," Human Gene Therapy 3(2):147-154, Apr. 1992.
De Block, M., and D. Debrouwer, "Two T-DNA's Co-Transformed Into *Brassica napus* by a Double Agrobacterium tumefaciens Infection Are Mainly Integrated at the Same Locus," Theoretical and Applied Genetics 82(3):257-263, Sep. 1991.
Doelling, J.H., et al., "Functional Analysis of *Arabidopsis thaliana* rRNA Gene and Spacer Promoters In Vivo and by Transient Expression," Proceedings of the National Academy of Sciences of the United States of America (PNAS) 90(16):7528-7532, Aug. 1993.
Doelling, J.H., et al., "The Minimal Ribosomal RNA Gene Promoter of *Arabidopsis thaliana* Includes a Critical Element at the Transcription Initiation Site," Plant Journal 8(5):683-692, Nov. 1995.
Doran, P.M., "Foreign Protein Production in Plant Tissue Cultures," Current Opinion in Biotechnology 11(2):199-204, Apr. 2000.
Eglitis, M.A., and W.F. Anderson, "Retroviral Vectors for Introduction of Genes Into Mammalian Cells," BioTechniques 6(7):608-614, Jul.-Aug. 1988.
Eglitis, M.A., et al., "Retroviral-Mediated Gene Transfer Into Hemopoietic Cells," Advances in Experimental Medicine and Biology 241:19-27, 1988.
Fabijanski, S.F., "Designing Canola Oils Through Chromosome Engineering," Presentation to 4th "Applying Genomics to Canola Improvement" Workshop, Saskatoon, Canada, Dec. 13, 2007.

(56) References Cited

OTHER PUBLICATIONS

Finer, J.J., and M.D. McMullen, "Transformation of Soybean via Particle Bombardment of Embryogenic Suspension Culture Tissue," In Vitro Cellular & Developmental Biology—Plant 27P(4):175-182, Oct. 1991.

Fischer, R., et al., "Towards Molecular Farming in the Future: Transient Protein Expression in Plants," Biotechnology and Applied Biochemistry 30(Pt. 2):113-116, Oct. 1999.

Fischer, R., et al., "Towards Molecular Farming in the Future: Using Plant-Cell-Suspension Cultures as Bioreactors," Biotechnology and Applied Biochemistry 30(Pt. 2):109-112, Oct. 1999.

Fraley, R.T., et al., "The SEV System: A New Disarmed Ti Plasmid Vector System for Plant Transformation," Nature Biotechnology 3:629-635, Jul. 1985.

Frame, B.R., et al., "Production of Transgenic Maize From Bombarded Type II Callus: Effect of Gold Particle Size and Callus Morphology on Transformation Efficiency," In Vitro Cellular & Developmental Biology—Plant 36(1):21-29, Jan.-Feb. 2000.

Fromm, M., et al., "Expression of Genes Transferred Into Monocot and Dicot Plant Cells by Electroporation," Proceedings of the National Academy of Sciences of the United States of America (PNAS) 82(17):5824-5828, Sep. 1985.

Fynan, E.F., et al., "DNA Vaccines: Protective Immunizations by Parenteral, Mucosal, and Gene-Gun Inoculations," Proceedings of the National Academy of Sciences of the United States of America (PNAS) 90(24):11478-11482, Dec. 1993.

Gelvin, S.B., "Agrobacterium-Mediated Plant Transformation: The Biology Behind the 'Gene-Jockeying' Tool," Microbiology and Molecular Biology Reviews 67(1):16-37, Mar. 2003.

GenBank Accession No. AJ309824.2, "Zea mays 25S rRNA Gene and Transposon-Like Sequence," deposited in GenBank on Oct. 23, 2008, <http://www.ncbi.nlm.nih.gov/nuccore/AJ309824> [retrieved Jul. 23, 2010], 4 pages.

GenBank Accession No. AY935814.1, "Glycine Max Isolate 24 26S Ribosomal RNA Gene, Partial Sequence," deposited in GenBank on Mar. 14, 2007, <http://www.ncbi.nlm.nih.gov/nuccore/62902790> [retrieved Jul. 23, 2010], 1 page.

GenBank Accession No. X52320.1, "Arabidopsis thaliana Genes for 5.8S rRNA and 25S rRNA With 18S rRNA Fragment," deposited in GenBank on Mar. 18, 1991, <http://www.ncbi.nlm.nih.gov/nuccore/16131> [retrieved Jul. 23, 2010], 2 pages.

GenBank Accession No. X76736.1, "B. napus mRNA for Cytosolic Glutamine Synthetase Isoform (BnGSR1-1) Related to the A-Genome Type of Brassica campestris," deposited in GenBank on Apr. 1, 1999, <http://www.ncbi.nlm.nih.gov/nuccore/436421> [retrieved Jul. 23, 2010], 2 pages.

Graham, F.L., and A.J. Van Der Eb, "Transformation of Rat Cells by DNA of Human Adenovirus 5," Virology 54(2):536-539, Aug. 1973.

Grindley, N.D.F., et al., "Mechanisms of Site-Specific Recombination," Annual Review of Biochemistry 75:567-605, Jul. 2006.

Hitz, W.D., et al., "The Use of Cloned Rapeseed Genes for the Cytoplamsic Fatty Acid Desaturases and the Plastid Acyl-ACP Thioesterases to Alter Relative Levels of Polyunsaturated and Saturated Fatty Acids in Rapeseed Oil," Proceedings of the 9th International Rapeseed Congress, Cambridge, United Kingdom, Jul. 4-7, 1995, pp. 470-472.

Jiao, S., et al., "Particle Bombardment-Mediated Gene Transfer and Expression in Rat Brain Tissues," Nature Biotechnology 11:497-502, Apr. 1993.

Johnston, S.A., "Biolistic Transformation: Microbes to Mice," Nature 346(6286):776-777, Aug. 1990.

Johnston, S.A., and D.-C. Tang, "Gene Gun Transfection of Animal Cells and Genetic Immunization," Methods in Cell Biology 43(Pt. A):353-365, 1994.

Katavic, V., et al., "Biotechnological Aspects: Fatty Acids," Biochemical Society Transactions 28(6):935-938, 2000.

Katavic, V., et al., "Improving Erucic Acid Content in Rapeseed Through Biotechnology: What Can the Arabidopsis FAE1 and the Yeast SLC1-1 Genes Contribute?" Crop Science 41(3):739-747, May-Jun. 2001.

Kato, A., et al., "Sensitive Fluorescence In Situ Hybridization Signal Detection in Maize Using Directly Labeled Probes Produced by High Concentration DNA Polymerase Nick Translation," Biotechnic and Histochemistry 81(2-3):71-78, Mar.-Jun. 2006.

Klabunde, J., et al., "Integration of Heterologous Genes in Several Yeast Species Using Vectors Containing a Hansenula polymorpha-Derived rDNA-Targeting Element," FEMS Yeast Research 4(2):185-193, Nov. 2003.

Klabunde, J., et al., "Single-Step Co-Integration of Multiple Expressible Heterologous Genes Into the Ribosomal DNA of the Methylotrophic Yeast Hansenula polymorpha," Applied Microbiology and Biotechnology 58(6):797-805, May 2002.

Klein, T.M., et al., "Transfer of Foreign Genes Into Intact Maize Cells With High-Velocity Microprojectiles," Proceedings of the National Academy of Sciences of the United States of America (PNAS) 85(12):4305-4309, Jun. 1988.

Klein, T.M., et al., "Transformation of Microbes, Plants and Animals by Particle Bombardment," Nature Biotechnology 10:286-291, Mar. 1992.

Knutzon, D.S., et al., "Modification of Brassica Seed Oil by Antisense Expression of a Stearoyl-Acyl Carrier Protein Desaturase Gene," Proceedings of the National Academy of Sciences of the United States of America (PNAS) 89(7):2624-2628, Apr. 1992.

Landy, A., "Dynamic, Structural, and Regulatory Aspects of λ Site-Specific Recombination," Annual Review of Biochemistry 58:913-941, Jul. 1989.

Lassner, M.W., et al., "A Jojoba β-Ketoacyl-CoA Synthase cDNA Complements the Canola Fatty Acid Elongation Mutation in Transgenic Plants," Plant Cell 8(2):281-292, Feb. 1996.

Lester, R.L., et al., "Mutant Strains of Saccharomyces cerevisiae Lacking Sphingolipids Synthesize Novel Inositol Glycerophospholipids That Mimic Sphingolipid Structures," Journal of Biological Chemistry 268(2):845-856, Jan. 1993.

Lopes, T.S., et al., "High-Copy-Number Integration Into the Ribosomal DNA of Saccharomyces cerevisiae: A New Vector for High-Level Expression," Gene 79(2):199-206, Jul. 1989.

Lu, L., et al., "High Efficiency Retroviral Mediated Gene Transduction Into Single Isolated Immature and Replatable CD343+ Hematopoietic Stem/Progenitor Cells From Human Umbilical Cord Blood," Journal of Experimental Medicine 178(6):2089-2096, Dec. 1993.

Search Report and Report of Technical Exam dated Apr. 3, 2018, issued in corresponding Brazilian Application No. PI0913818-8, filed Sep. 30, 2009, with machine translation, 24 pages.

Katavic, V., et al., "Utility of the Arabidopsis FAE I and Yeast SLC-I Genes for Improvements in Erucic Acid and Oil Content in Rapeseed," Biochemical Society Transactions 28(6):935-937, Dec. 2000.

* cited by examiner

Figure 2
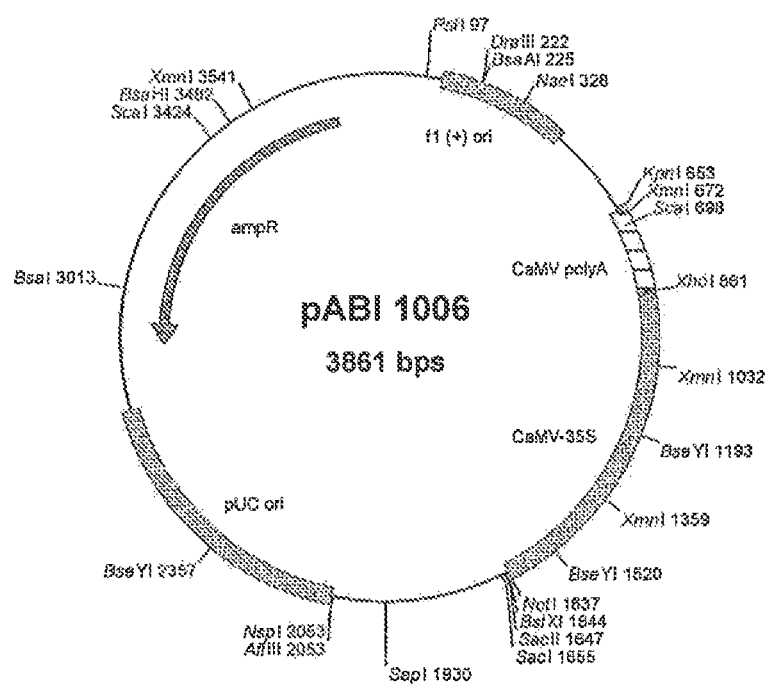
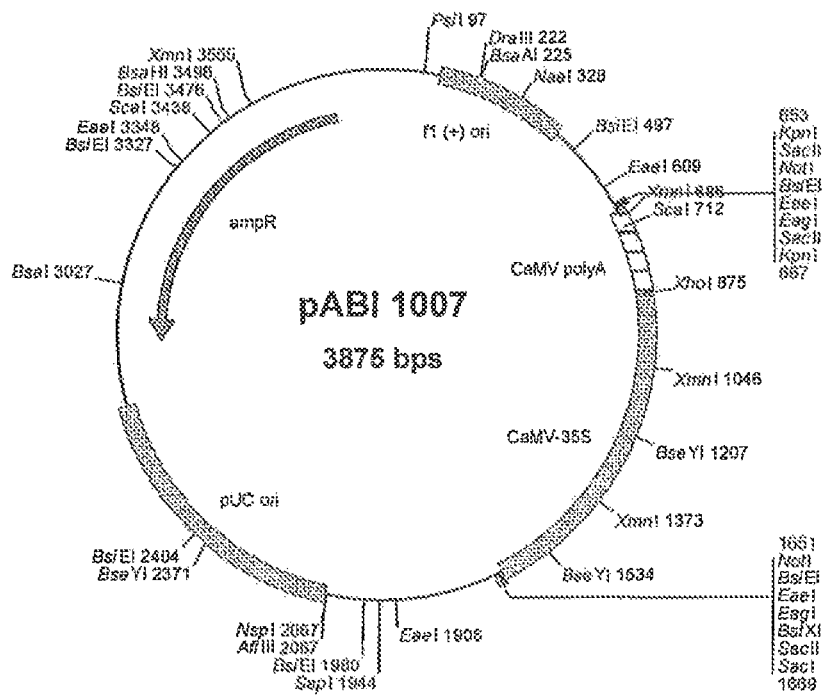

Figure 4:
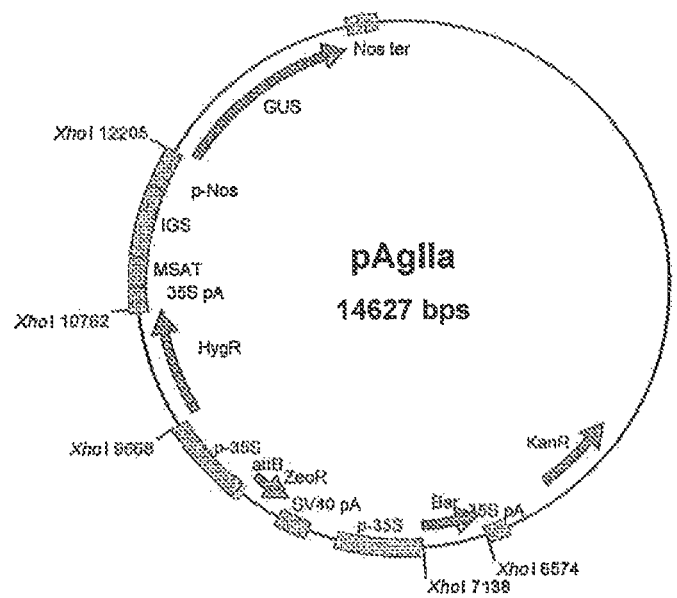
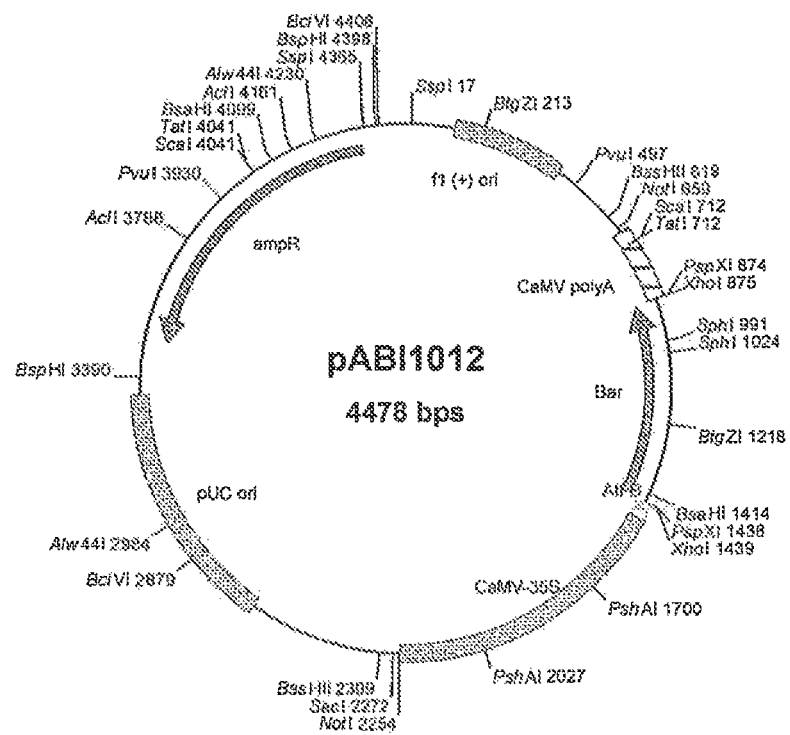

Figure 6:
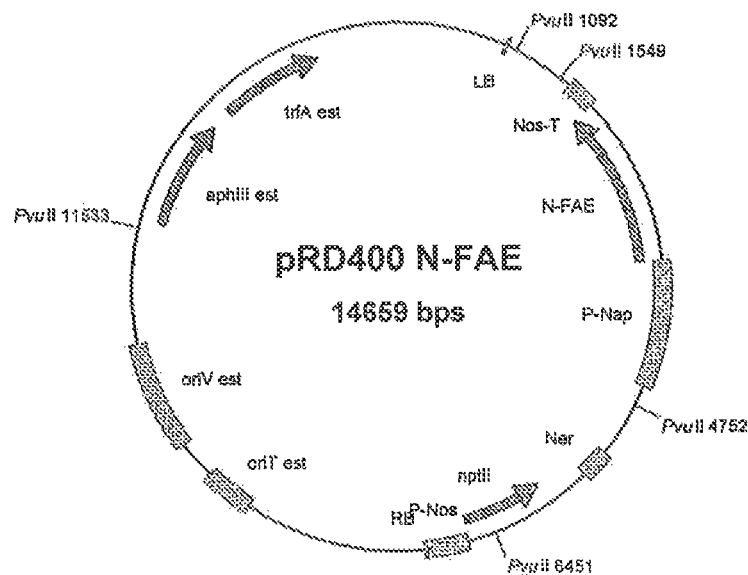
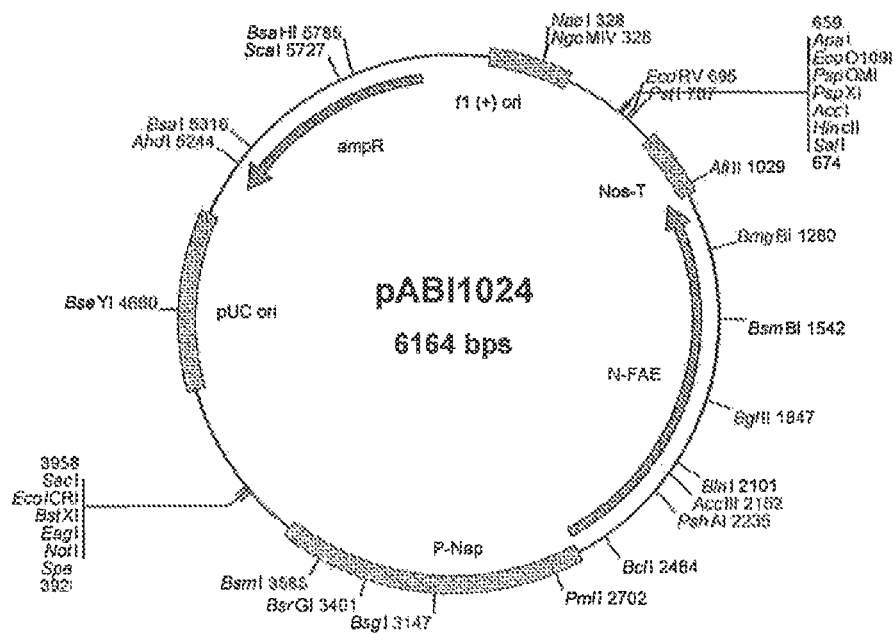

Figure 7:
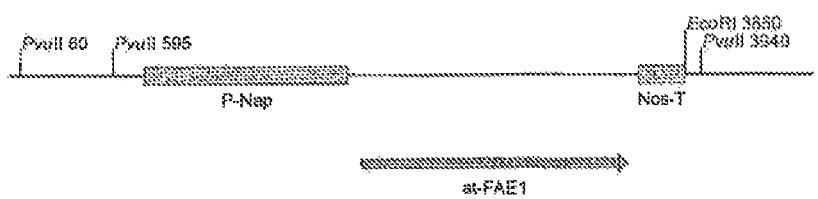
P-Nap:atFAE1:Nos-T cassette
(4570 bps)
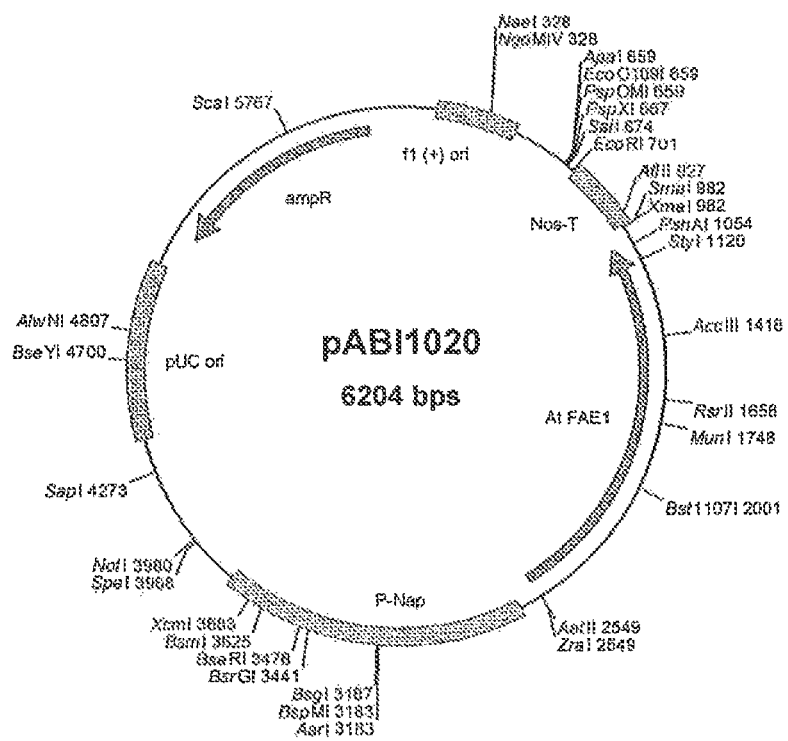

FIG. 12
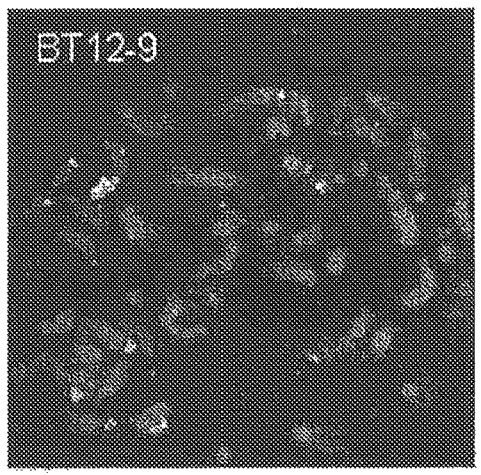
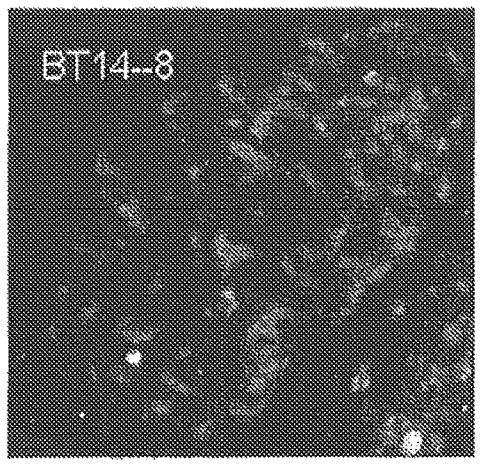
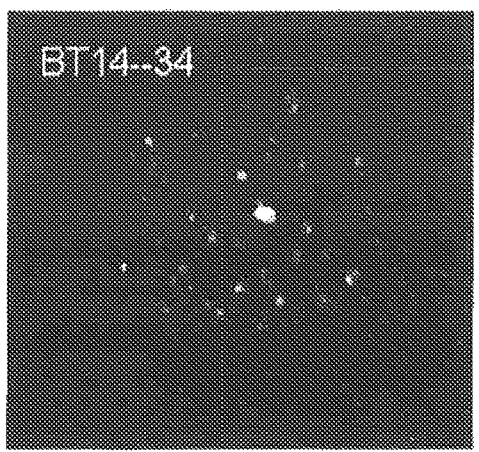

Figure 13
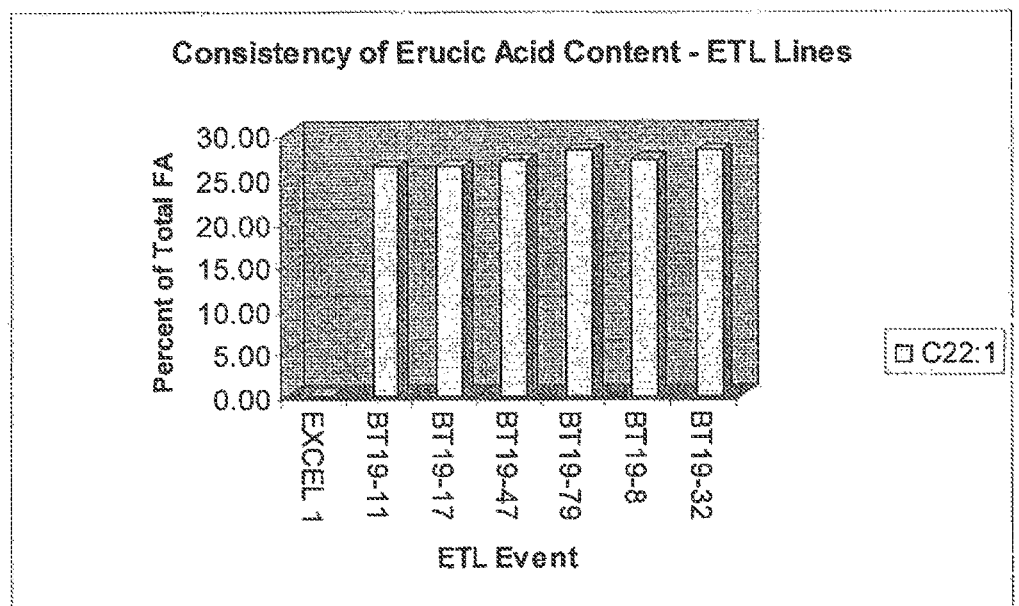
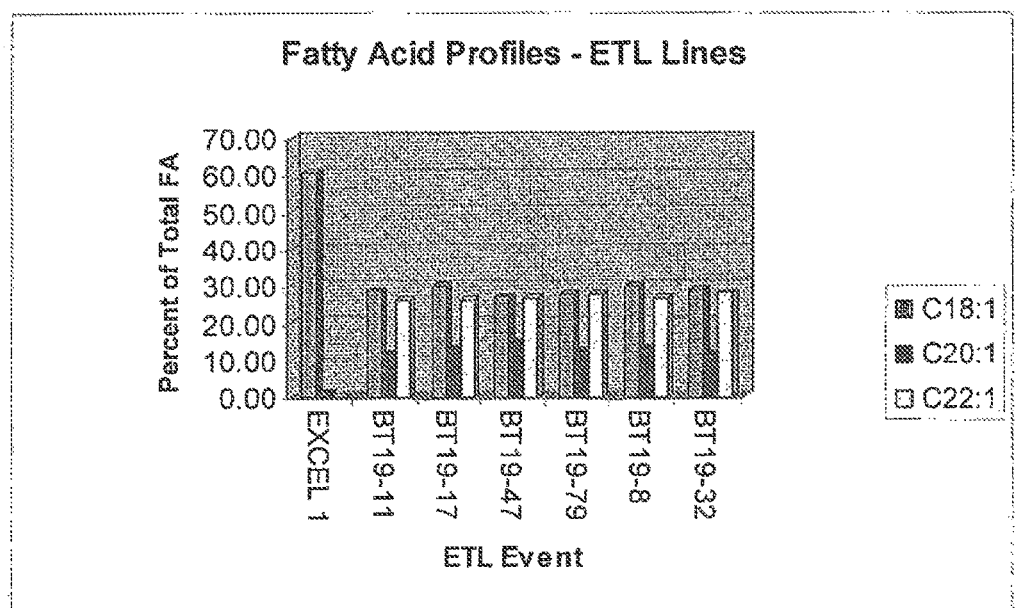

Nucleotide homology of Genbank X76736 sequence (Brassica napus cytoplasmic GS1.1 gene) and putative GS PCR clone 1.4

Protein coding sequence homology of Genbank X76736 (Brassica napus cytoplasmic GS1.1 translated gene product) and putative GS PCR clone 1.4 translated gene product

```
BNGLUTS    1  mslltdlynldlsdntekliaeylwvggsymdmrskartl
GS 1.4 Trans 1  mslltdlynldlsdntekliaeylwvqgsmdmrskartl BNGLUTS   41  pqpvtdpsklpkwnydgsstgqapgedsevilypqaifkd
GS 1.4 Trans 41 pqpvtdpsklpkwnydgsstgqapgedsevilypqaifkd BNGLUTS   81  pfrrgmnilvmcdtytpagepiptnkrhaaaqifsngdvv
GS 1.4 Trans 81 pfrrgmnilvmcdtytpagepiptnkrhaaaqifsmgdvv BNGLUTS  121  aevpwygleqeytllqkdvmwpvgwpigqflpqgpyycs
GS 1.4 Trans 121 aevpwygleqeytllqkdvmwpvgwpigqflpqgpyycs BNGLUTS  161  vgadksfqrdivdihykaclyaqinisqingevwpqqwef
GS 1.4 Trans 161 vqadksfqrdivdihykaclyaqinisqingevwpqqwef BNGLUTS  201  qvgpsvqisaadevwiarfileriteiagvvvstdpkpip
GS 1.4 Trans 201 qvgpsvqisaadevwiarfileriteiagvvvstdpkpip BNGLUTS  241  gdwngaqahtnystksmreeygyeilkkaidkiqlrhkeh
GS 1.4 Trans 241 gdwngaqahtnystksmreeygyeilkkaidkiqlrhkeh BNGLUTS  281  isaygeqnerrltqhhetadlntfkwgvanrqasirvgrd
GS 1.4 Trans 281 isaygeqnerrltqhhetadlntfkwgvanrqasirvgrd BNGLUTS  321  tekegkgyfedrrpasnmdpytvtsmiaettllwnp
GS 1.4 Trans 321 tekegkgyfedrrpasnmdpytvtsmiaettllwnp
```

FIG. 16

FIG. 18
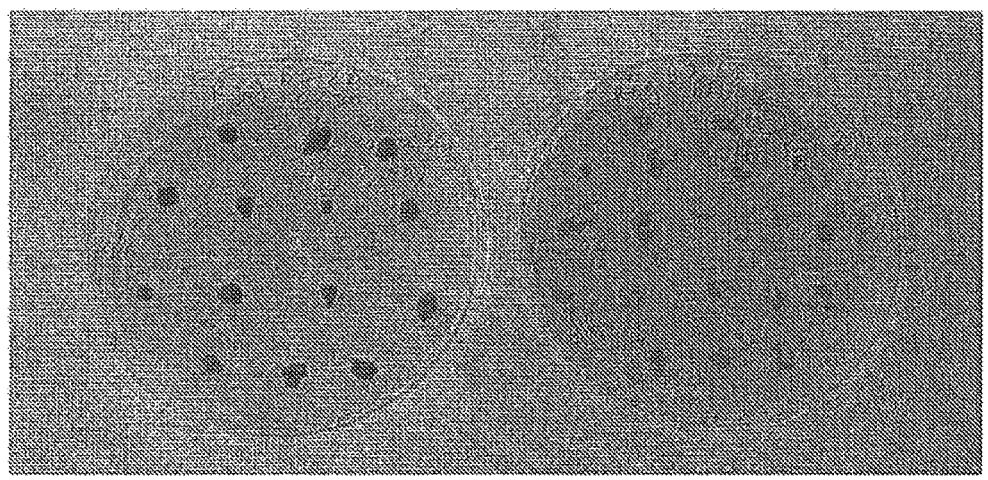
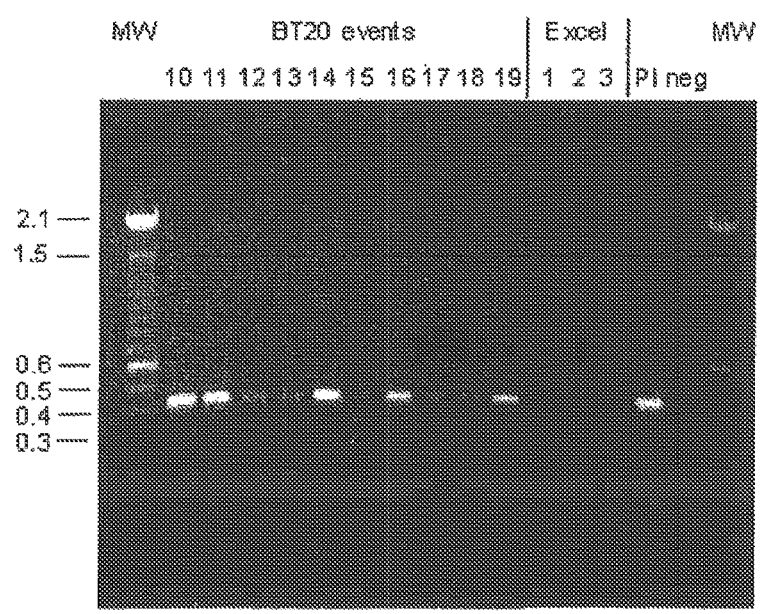

FIG. 19B

Figure 21:
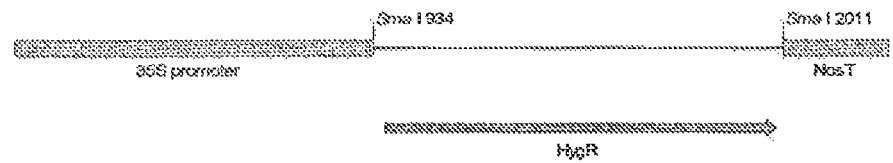
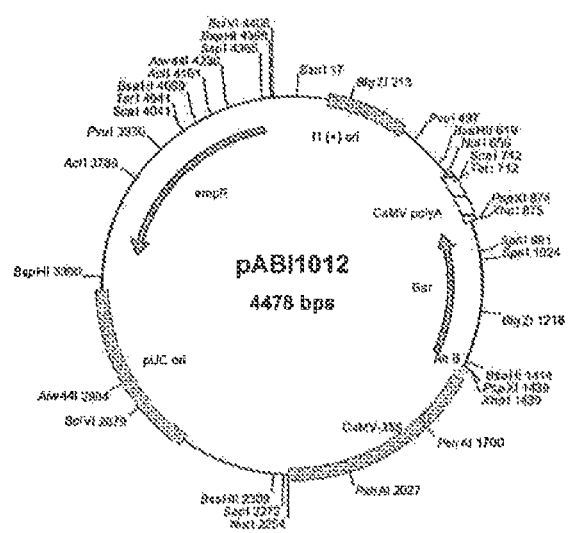
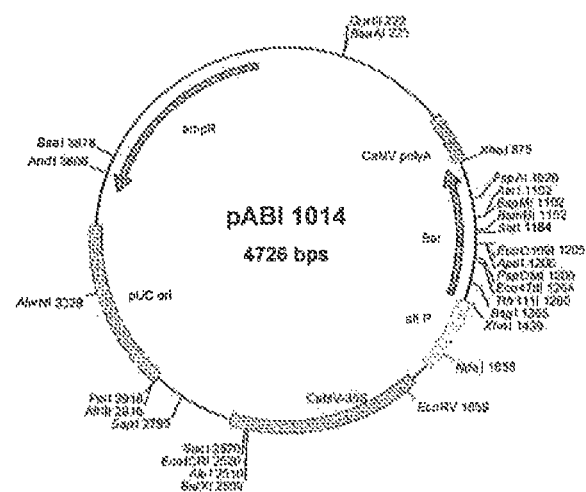

Figure 22:
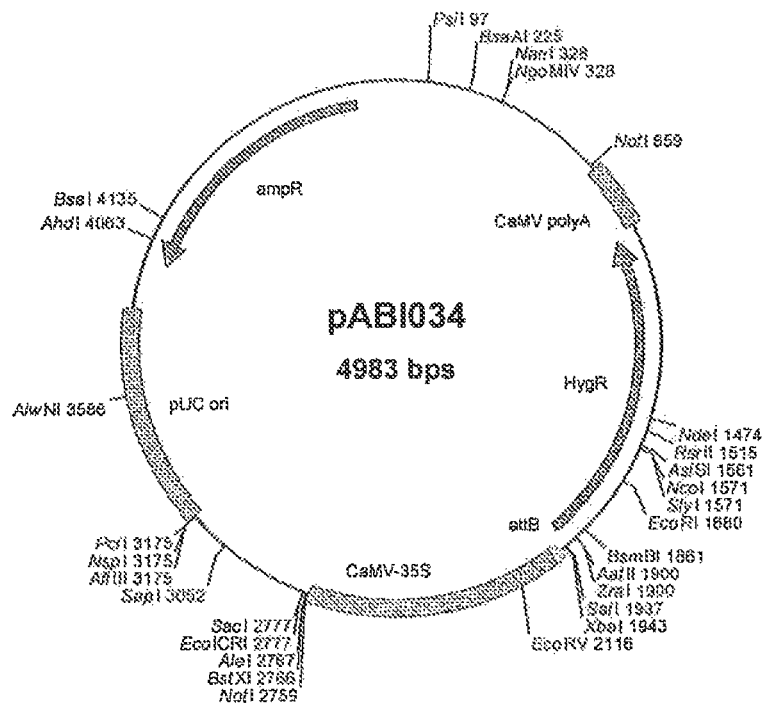
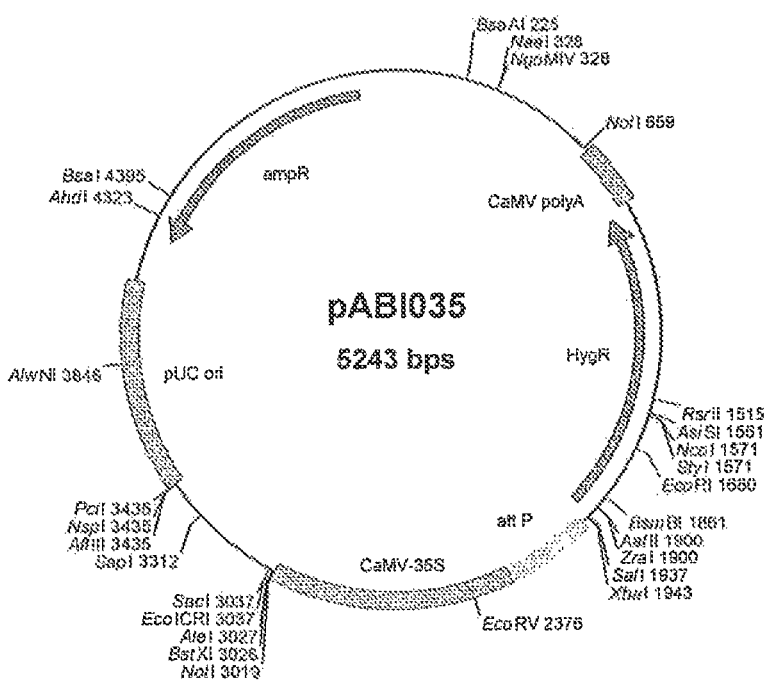

FIG. 23A

```
26S Zea Mays 1F >
CCGTC CAAGGCTAAA TACAG

1041 AAGTCCGTC CAAGGCTAAA TACAGCGGAG AGAGCGATAG AGACGGATAGA GGACTTGAA AAGAGAGTCA GAATCCCG GGAAGGAAGC GGAAGGAAGC
     TTCGAGCGTC GTTCGATTT AGTCGCGTC TCTGCGACTG GCCGGTCCGT GCTACTCAT TCTCAAACTT TTCTCACGA CTTAAGCGG CCCCACCCCG
     >................................................................................................> ...26S rDNA

1171 TGGCGACGCG CCCCGCGCT ATCGGAAGG GTCCTCGTG CGGTCGCGG GCCGAGCGC CTGGCCGCT TGTGCGCGC GCTGGCGGGC GCCCCCGGCA GCCGTCGTG
     ACGCGGCGC GGGCCGGCA TACGCGTTGC GGAGGACGAC GCCAGAGCTA GCCGAGCCG ACACGAGGCA TTCGGCGCC CGGGATCCG CGGGGGCGT GGGAGCAGC
     >................................................................................................> ...26S rDNA

1301 GGCCGGACGG TATCGGCGG CCTTCGCGG CCCTGGGGG GCTAGCTCGG ACGACTGC GAGCTCCCCA TCCGACCCT CTTGAAACAC AGGACCAAGGA GTCGACGAC GACGGGTCA
     CACGGCTGC ATAGGCGGCC GGAGACCCCG GGAGACTCGG GGATGCGGCG TGGCCAGCCG TGCCGAGCGT CTCGGAGGGT AGCTGGCA GAACTTGTG CTCGGTCT CAGCTGAC GCACGCTAG CTGCCAAGT
     >................................................................................................> ...26S rDNA

1431 CAAACTCGAG ATGGCCAAGG AAGCTCAAGGA GCGGGACGCC CTCAGGAGCC GCGGACCCGG GCTCTCGG AGGGTCGAG TCTTCGTGA AGGGTCGAG TTGACCACT CCTCTCGGA CCTGTCGGGA GTGACTAT
     CTTTGGACTC TACGCGTTCC TTCGAGCTGC CGCCTCCGG GAGCTCGG GAGTCGCTGG GAGTCGACT AGAGACACT TCCAAGTC AACTCGTGA GGACACTGTA GGGCTTCTA CCATTGATA
     >................................................................................................> ...26S rDNA

1561 GGCTGAGCGG GAGGAAGCCA GAGGAAACTC TGTGCAGGG GAGCCCACAC GAGTTCTATC AAATCGTTCG ACTAGATGC TGAAGGAAT TGTGCCGGAG GAAAGACTAA TGAACTGAC TAGTAGTGG TTCCCCGA
     CGGAGTCGCC CGGTTCGGT ACCACTCGT AGTTCGGTA GGACCCCG CATATCCCG CCTCCACCAT ACCTTCGTA AGCTCGAGC CATATTGCAC CTTTCTCGAT AGCTTCCGTA ATCATCGACC AAGGAGCT
     >................................................................................................> ...26S rDNA

1691 ACTTTCCGTC AGGATACTG GAGCCCCCAA GAGTTCTATC GGGTAAAGCC AATGATTGAA GGAAACAGG AATGCTTCG GGCATCAGGG GCCATCAGCC TCGAACCTG TAAATAGGTA GGAGGGGGG GCTCTTCG
     TCAAGCGAG TCTATCGAC CGTCGGTGTG CTCAAGATAG CCCATTCGG TTACTAAACT CCTAGTCC CGGGTTCGG GAGTGGATA AGAGTTGAA ATTATTCCAT CCTCGGCGC CGCACCAAGC
     >................................................................................................> ...26S rDNA

1821 TGAGCCGTGC CACGGAATCG GTGGGCCAA GTGGCCGGTC CACCCGTTA AGAACTGGG ATGGCGAAGG AAGCGGAAGG AACCGGAAG CGGGTAAGG TCCAAACTG CGGGTAAGG AAGGGTGT
     ACTGGGACGG GTCCGGAGC CCTCCAGTT CACCCGGTAA AAACCATCG TTTGACCGG AAGCATCG TCTTGACCTG GCCAATGC TACGCCTAC TACGCCTAC ACGGGTCGC GCCGAATGGG ATCTTGGGTC TTTCCACAA
     >................................................................................................> ...26S rDNA
```

FIG. 23B

```
1951  GGATCATTAA GACAGGAGGA CGATGCTCAT GGAAGTCGAA ATCCCGTAAG GACTGCTTAA CAACTCACCT GCGGATCCAA AAGGGATTAG CGGTGAACGG CCGCAAGCCG ACCGGCCCAT
      CCAGTAATT CTGTCGTCCT GCTACGACTA CCTTCAGTTA GGGCGAATTC CTGACACGTT AGCGAGTCCA CGCCTAGCT GATCGAGTCC TTACCTACC GCGACTGGCG GCGACTGGCG GCGCTGGGTG TGGGCGGTA
      >.................................. -23S rDNA

2081  CTGGACGGAC GACATGCCCC GATGAGTAGG AGGGGGACAAG GCCCCCGCAA AACCCGGGC GGGAGCGGGC CGCTCGGTCA GATCTGGTG GTAGTAACAA ATATCCAAAT GAGAACTTG
      GACCCCCTG CGTAGGGGA CTACTCATCC TCCCGGGTGC CGGGCGGGTG CCGTCGGGGA GCAGACCAGC GCAAACCACG CTAGAACCGT CATCATCGTT TATAGCTTA CGTTCAAAC
      >.................................. -25S rDNA

2211  AAGGCCGAAG AGAGGAAAGG TCCATGTGA ACGGCACTTG AGCGGATTCT AGGGATCGGG GAAACCCGG CACATCAGCC GATCACGCG GTCACCGGAA AGGGGACCCG GTTAAGCATT
      TTCGGCTTC TCCTCTTTC AAGTACACT TGCCCTAGGA GTGTACCCAT TCCCCGCC GCTTGGCC GTCTATCGCG CTAGTCCGCG CAGTGGCGCT TCCCTTAGGC CAATTCTAA
      >.................................. -23S rDNA

2341  CCCGACCCG GACGGTGCGG CAGACGCCCA CGTTAGGAAC CCCCGGGGG CCTGGACACG AGTATCTTT GGCTCTTAAC CCCTGGCGCA CCCCGGATCC GGTTAGGCG GAGGTAGGGT
      GGGCTCGGC GCTGCGGGCG GCCTACGGGC GGAGCCTTC AGGCTCRCG GGAGCCCC TCAATAGAA AGACGAATTG CCGGGCGGTT GGGACCTTAG CCAAGCCGC CTCATCCCA
      >.................................. -25S rDNA

2471  CCAGGGCCG GAAGAGCACC GCACATCGGG CTTCTCGTGG TGCCCCCGG GCGTCCTTG AAAATCCGGA GGACCAATA CGATCACGC CGGTCGTAC TCAATAACCC GCGTAGGAGG CAAGGTGAAC
      GATCCGGGA CTTCGCGTGG CGCTAGCGC GCCACAGGCC GCGGGGAAC TTTTAGCCT CCTGCCGTAT GGTAAGGTCGG GCCAGCATG AGTATGGGCG TAGTCCAGAG GCTCCACTTG
      >.................................. -23S rDNA

2601  AGACCCTCGG CCAAATGGAAC AATGTAGCCA AGGGAAGTCG GCAAAACGGA TCCCTAACTT CGGGAAAAGG ATTGGCCCTG AGGGTTGGGC TCGGGGTCC CGGCCCCGAA CCCGTCGGCT GCTGGGTGGA
      TCTGGACGAC GGTTACCTTG TTACACCCGT CGTTTGCCT AGGGATTGAA GCCCTTTCC AGGGATTGAA TACCCGACG GGCAGCCGGG GGGCCGGGA TACCAGAGA CAGCTCCC
      >.................................. -25S rDNA

2731  TGCTCGAGCT GCTCCGCTGG GCTCCGGGG CGGAAGCGGGG GGCCTCCGGG GACGCGCCAC CCCGCCCGT GAACCCGGGGG GGAAGCACCGG GGCAACCCGG GTGACCGGGG TTCCCCGGCC GAGGCCCGGG CAAGGCGGAT
      ACGGCCTCGA GGTTACCTGG TTACATCCGT TCACATTGAA GCCCTTTGCCT AGGGATCAA GCCCTTTGCCT AGGGATCAA GAGCCCCGG CAGTCTGGTG CTCAGTCGT TGCTCAGTCT GCTCAGTCT GCTAGTCT
      >.................................. -25S rDNA
```

```
                                                                      < 26S Zea Mays 1R
                                                                      CCTAATAC TGACTTGCGG AG
3771  GATTCACACA ATTGGTCATC GCGACTTGGT GAAAAGCCAG TGGCCGGAAG CTBCCGTGTG CCGGATTATG ACGAACGCC TCTAAGTCAG AATCCAAGCT AGCAACCGGC GCCTTGCTC GCCGCCCGC
      CTAAGTCTGT AACCAGTAG CGGGAACCAA CTTTTGCGTC ACCGCGGTTC GAGGCACAC TGACTTGGGG AGATTACGTC TTAGGTGCGG CGGCGACCAG TGTTGGCTG CGGAGACGAG CGGGGGGCGG
      >..........                                    ........................255 rDNA 3901  CCGACCCACG TTAGGCGTT CAGCGCCCAA GGGCCCGTGC CATTGGGTCA GCCCGGCGCC CCGAGCGCC CGGGGGGCC GCGGGGGGCC TCCCATTCCA ACGGCGGCG TGCTGAAGC TTTGCAGACG
      GGCTGGGTGC AATTCCGCCA GCGCGAGCTT CCCGGAGCTT GCGGCGCAAG GTAACGGAGC CGGCGTGCG AGGGAGGCGG TGCCGGGCTG ACGACTTAGG AACCTGTGC
      >..........                                    ........................25S rDNA < 26S Zea Mays 2R
                                                          CGT AACATTCACC GTCTCACC
4031  ACTAAAACG CGAACGGGCA TGTAAGTGG CAGAGTGGCC TGGTGCGCCC GATTCCACTG AGATCCAGCC CGGGGTCGCA CGGATTGGTC CTCCCCCCA AACAACGCAC CGGCCTAGCC ACCTA
      TGAATTTGGC GCTGCCCGT ACATTCACC GTCTCACCG AACGACGGTG CTAAGGTGG GGGGCAGCGT GCTAAGCCGG GAAGGGGGT GGATCCCTG CCGGATCGC TGGAT
      >..........                                    ........................
```

FIG. 24E attB HindIII PstI (41 bps)

```
1  agcttgaagc ctgcttttt atactaactt gagcgaatgc a
       acttcg gacgaaaaaa tatgattgaa ctcgctt
```

Figure 27:
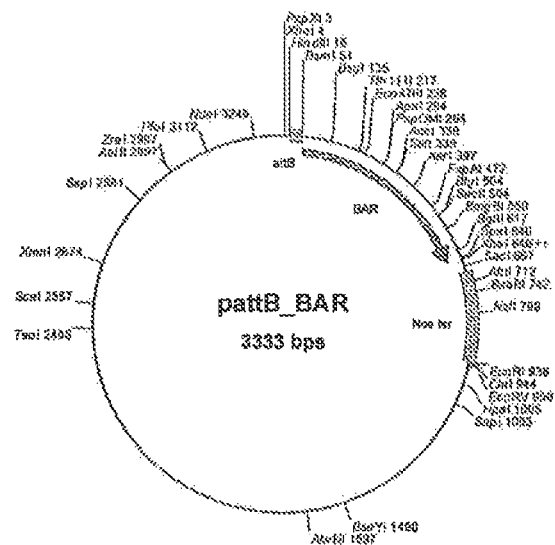
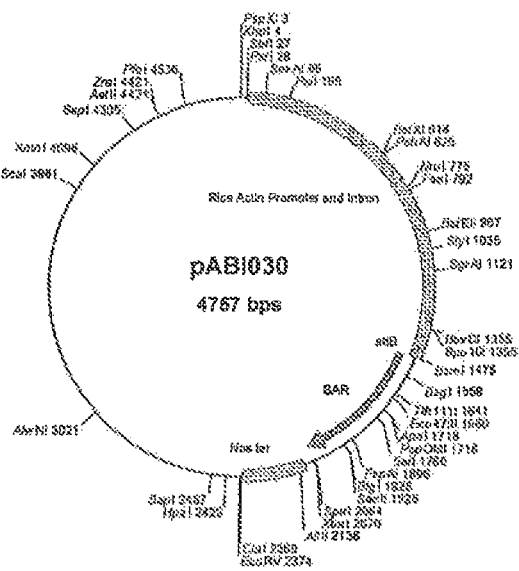

Figure 28:
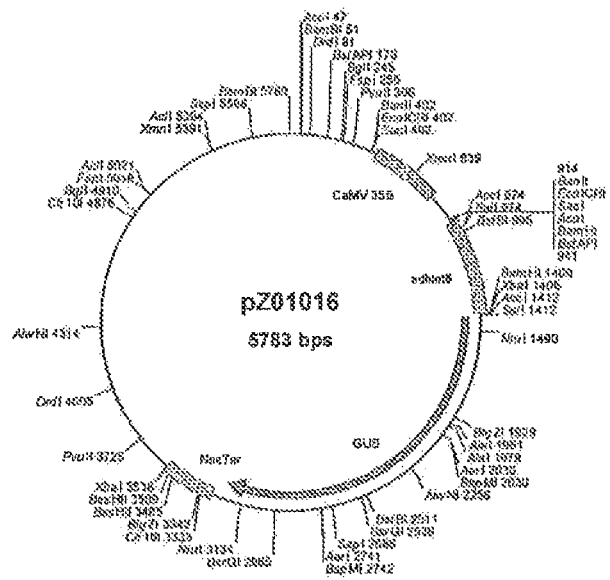
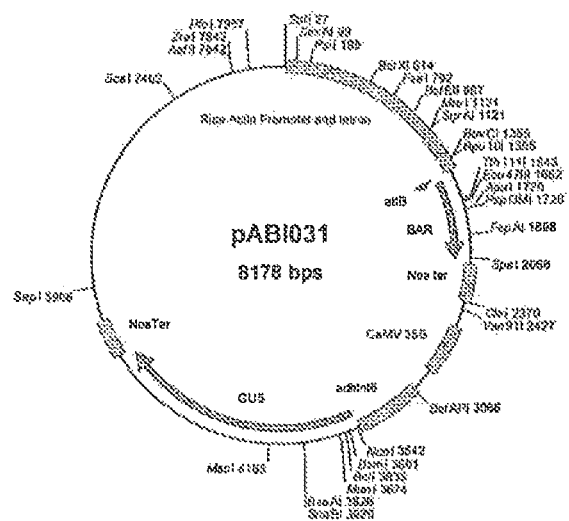

SEQUENCE LISTING

<160> NUMBER OF SEQ ID NOS: 34

<210> SEQ ID NO 1
<211> LENGTH: 39
<212> TYPE: DNA
<213> ORGANISM: Artificial
<220> FEATURE:
<223> OTHER INFORMATION: attB

<400> SEQUENCE: 1
tcgactgaag cctgcttttt tatactaact tgagcgaac                39

<210> SEQ ID NO 2
<211> LENGTH: 39
<212> TYPE: DNA
<213> ORGANISM: Artificial
<220> FEATURE:
<223> OTHER INFORMATION: attB

<400> SEQUENCE: 2
tcgagttcgc tcaagttagt ataaaaaagc aggcttcag                39

<210> SEQ ID NO 3
<211> LENGTH: 287
<212> TYPE: DNA
<213> ORGANISM: Artificial
<220> FEATURE:
<223> OTHER INFORMATION: attP

<400> SEQUENCE: 3
tcgaccttgc gctaatgctc tgttacaggt cactaatacc atctaagtag ttgattcata    60
gtgactgcat atgttgtgtt ttacagtatt atgtagtctg ttttttatgc aaaatctaat   120
ttaatatatt gatatttata tcattttacg tttctcgttc agcttttta tactaagttg    180 gcattataaa aaagcattgc ttatcaattt gttgcaacga acaggtcact atcagtcaaa   240
ataaaatcat tatttgattt caattttgtc ccactccctg cctctgc                 287

<210> SEQ ID NO 4
<211> LENGTH: 287
<212> TYPE: DNA
<213> ORGANISM: lambda phage

<400> SEQUENCE: 4
tcgagcagag gcagggagtg ggacaaaatt gaaatcaaat aatgatttta ttttgactga    60
tagtgacctg ttcgttgcaa caaattgata agcaatgctt ttttataatg ccaacttagt   120
ataaaaaagc tgaacgagaa acgtaaaatg atataaatat caatatatta aattagattt   180
tgcataaaaa acagactaca taatactgta aaacacaaca tatgcagtca ctatgaatca   240
actacttaga tggtattagt gacctgtaac agagcattag cgcaagg               287

<210> SEQ ID NO 5
<211> LENGTH: 1071
<212> TYPE: DNA
<213> ORGANISM: brassica napus
<220> FEATURE:
<221> NAME/KEY: CDS
<222> LOCATION: (1)..(1071)

<400> SEQUENCE: 5 atg agt ctt ctg acc gat ctc gtt aac ctt gac ctc tca gac aac act    48
Met Ser Leu Leu Thr Asp Leu Val Asn Leu Asp Leu Ser Asp Asn Thr
1               5                   10                  15

```
gag aaa atc atc gct gaa tac ata tgg gtt ggt ggt tca gga atg gat        96
Glu Lys Ile Ile Ala Glu Tyr Ile Trp Val Gly Gly Ser Gly Met Asp
             20                  25                  30 atg aga agc aaa gcc agg act ctc cct gga cct gtg acc gat cca tca       144
Met Arg Ser Lys Ala Arg Thr Leu Pro Gly Pro Val Thr Asp Pro Ser
         35                  40                  45 aag ctc cca aaa tgg aat tat gat ggt tca agc act ggc caa gct cct       192
Lys Leu Pro Lys Trp Asn Tyr Asp Gly Ser Ser Thr Gly Gln Ala Pro
     50                  55                  60 ggt gaa gac agc gaa gtg atc tta tac cct caa gcg att ttc aaa gat       240
Gly Glu Asp Ser Glu Val Ile Leu Tyr Pro Gln Ala Ile Phe Lys Asp
65                  70                  75                  80 ccg ttc cgt aga ggc aac aac att ctt gtc atg tgt gat act tac acc       288
Pro Phe Arg Arg Gly Asn Asn Ile Leu Val Met Cys Asp Thr Tyr Thr
                 85                  90                  95 cct gcg ggt gaa cca atc cct acg aac aag aga cat gct gca gct cag       336
Pro Ala Gly Glu Pro Ile Pro Thr Asn Lys Arg His Ala Ala Ala Gln
             100                 105                 110 atc ttt agc aac cct gat gtt gtt gct gaa gtg cca tgg tat gga atc       384
Ile Phe Ser Asn Pro Asp Val Val Ala Glu Val Pro Trp Tyr Gly Ile
         115                 120                 125 gaa caa gaa tac act ctg ttg cag aaa gat gtg aat tgg cct gtc gga       432
Glu Gln Glu Tyr Thr Leu Leu Gln Lys Asp Val Asn Trp Pro Val Gly
     130                 135                 140 tgg ccc att ggt gga ttc ccc ggc cct cag gga cca tac tac tgc agt       480
Trp Pro Ile Gly Gly Phe Pro Gly Pro Gln Gly Pro Tyr Tyr Cys Ser
145                 150                 155                 160 gtt gga gct gac aaa tct ttt gga aga gac att gtt gat gct cac tac       528
Val Gly Ala Asp Lys Ser Phe Gly Arg Asp Ile Val Asp Ala His Tyr
                 165                 170                 175 aag gct tgt ttg tat gct gga att aac atc agt gga atc aat gga gaa       576
Lys Ala Cys Leu Tyr Ala Gly Ile Asn Ile Ser Gly Ile Asn Gly Glu
             180                 185                 190 gtc atg cct ggt cag tgg gag ttc caa gtc gga ccg tcg gtt ggt atc       624
Val Met Pro Gly Gln Trp Glu Phe Gln Val Gly Pro Ser Val Gly Ile
         195                 200                 205 tca gct gct gat gaa gtg tgg att gct cgt ttt att ttg gag agg atc       672
Ser Ala Ala Asp Glu Val Trp Ile Ala Arg Phe Ile Leu Glu Arg Ile
     210                 215                 220 aca gag att gct ggt gtg gtt gta tct ttt gac cca aaa cca att ccg       720
Thr Glu Ile Ala Gly Val Val Val Ser Phe Asp Pro Lys Pro Ile Pro
225                 230                 235                 240 ggt gac tgg aac gga gct ggt gct cac acc aat tac agt act aaa tcg       768
Gly Asp Trp Asn Gly Ala Gly Ala His Thr Asn Tyr Ser Thr Lys Ser
                 245                 250                 255 atg agg gag gaa gga gga tac gag ata atc aag aag gca att gat aag       816
Met Arg Glu Glu Gly Gly Tyr Glu Ile Ile Lys Lys Ala Ile Asp Lys
             260                 265                 270 ctc gga ctg aga cac aag gag cac att tct gct tac ggt gaa ggc aac       864
Leu Gly Leu Arg His Lys Glu His Ile Ser Ala Tyr Gly Glu Gly Asn
         275                 280                 285 gag cgt cgt ctc act gga cac cat gaa act gct gat atc aac act ttc       912
Glu Arg Arg Leu Thr Gly His His Glu Thr Ala Asp Ile Asn Thr Phe
     290                 295                 300 aaa tgg ggt gtt gca aac cgt gga gca tca atc cgt gta gga cgt gac       960
Lys Trp Gly Val Ala Asn Arg Gly Ala Ser Ile Arg Val Gly Arg Asp
305                 310                 315                 320 acg gag aag gaa ggg aaa gga tac ttt gag gat agg agg cca gct tcc      1008
Thr Glu Lys Glu Gly Lys Gly Tyr Phe Glu Asp Arg Arg Pro Ala Ser
                 325                 330                 335
```

```
aac atg gac cct tac act gta act tcc atg att gca gag act aca ctt    1056
Asn Met Asp Pro Tyr Thr Val Thr Ser Met Ile Ala Glu Thr Thr Leu
        340                 345                 350 ctt tgg aat cct tga                                                 1071
Leu Trp Asn Pro
        355
```

<210> SEQ ID NO 6
<211> LENGTH: 356
<212> TYPE: PRT
<213> ORGANISM: brassica napus

<400> SEQUENCE: 6

```
Met Ser Leu Leu Thr Asp Leu Val Asn Leu Asp Leu Ser Asp Asn Thr
1               5                   10                  15

Glu Lys Ile Ile Ala Glu Tyr Ile Trp Val Gly Gly Ser Gly Met Asp
            20                  25                  30

Met Arg Ser Lys Ala Arg Thr Leu Pro Gly Pro Val Thr Asp Pro Ser
        35                  40                  45

Lys Leu Pro Lys Trp Asn Tyr Asp Gly Ser Ser Thr Gly Gln Ala Pro
50                  55                  60

Gly Glu Asp Ser Glu Val Ile Leu Tyr Pro Gln Ala Ile Phe Lys Asp
65                  70                  75                  80

Pro Phe Arg Arg Gly Asn Asn Ile Leu Val Met Cys Asp Thr Tyr Thr
                85                  90                  95

Pro Ala Gly Glu Pro Ile Pro Thr Asn Lys Arg His Ala Ala Ala Gln
            100                 105                 110

Ile Phe Ser Asn Pro Asp Val Val Ala Glu Val Pro Trp Tyr Gly Ile
        115                 120                 125

Glu Gln Glu Tyr Thr Leu Leu Gln Lys Asp Val Asn Trp Pro Val Gly
    130                 135                 140

Trp Pro Ile Gly Gly Phe Pro Gly Pro Gln Gly Pro Tyr Tyr Cys Ser
145                 150                 155                 160

Val Gly Ala Asp Lys Ser Phe Gly Arg Asp Ile Val Asp Ala His Tyr
                165                 170                 175

Lys Ala Cys Leu Tyr Ala Gly Ile Asn Ile Ser Gly Ile Asn Gly Glu
            180                 185                 190

Val Met Pro Gly Gln Trp Glu Phe Gln Val Gly Pro Ser Val Gly Ile
        195                 200                 205

Ser Ala Ala Asp Glu Val Trp Ile Ala Arg Phe Ile Leu Glu Arg Ile
    210                 215                 220

Thr Glu Ile Ala Gly Val Val Val Ser Phe Asp Pro Lys Pro Ile Pro
225                 230                 235                 240

Gly Asp Trp Asn Gly Ala Gly Ala His Thr Asn Tyr Ser Thr Lys Ser
                245                 250                 255

Met Arg Glu Glu Gly Gly Tyr Glu Ile Ile Lys Lys Ala Ile Asp Lys
            260                 265                 270

Leu Gly Leu Arg His Lys Glu His Ile Ser Ala Tyr Gly Glu Gly Asn
        275                 280                 285

Glu Arg Arg Leu Thr Gly His His Glu Thr Ala Asp Ile Asn Thr Phe
    290                 295                 300

Lys Trp Gly Val Ala Asn Arg Gly Ala Ser Ile Arg Val Gly Arg Asp
305                 310                 315                 320

Thr Glu Lys Glu Gly Lys Gly Tyr Phe Glu Asp Arg Arg Pro Ala Ser
                325                 330                 335
```

```
Asn Met Asp Pro Tyr Thr Val Thr Ser Met Ile Ala Glu Thr Thr Leu
            340                 345                 350

Leu Trp Asn Pro
        355

<210> SEQ ID NO 7
<211> LENGTH: 1071
<212> TYPE: DNA
<213> ORGANISM: brassica napus
<220> FEATURE:
<221> NAME/KEY: CDS
<222> LOCATION: (1)..(1071)

<400> SEQUENCE: 7 atg agt ctt ctg acc gat cac gtt aac ctt gac ctc tca gac aac act      48
Met Ser Leu Leu Thr Asp His Val Asn Leu Asp Leu Ser Asp Asn Thr
1               5                   10                  15 gag aaa atc att gct gaa tac ata tgg gtt ggt ggt tca gga atg gat      96
Glu Lys Ile Ile Ala Glu Tyr Ile Trp Val Gly Gly Ser Gly Met Asp
            20                  25                  30 atg aga agc aaa gcc agg act ctc cct gga cct gtg acc gat cca tca     144
Met Arg Ser Lys Ala Arg Thr Leu Pro Gly Pro Val Thr Asp Pro Ser
        35                  40                  45 aag ctc cca aaa tgg aat tat gat ggt tca agc act ggc caa gct cct     192
Lys Leu Pro Lys Trp Asn Tyr Asp Gly Ser Ser Thr Gly Gln Ala Pro
    50                  55                  60 ggt gaa gac agt gaa gtg atc tta tac cct caa gcg att ttc aaa gat     240
Gly Glu Asp Ser Glu Val Ile Leu Tyr Pro Gln Ala Ile Phe Lys Asp
65                  70                  75                  80 ccg ttc cgt aga ggc aac aac att ctt gtc atg tgt gat act tac acc     288
Pro Phe Arg Arg Gly Asn Asn Ile Leu Val Met Cys Asp Thr Tyr Thr
                85                  90                  95 cct gcg ggt gaa cca atc cct acg aac aag aga cat gct gca gct cag     336
Pro Ala Gly Glu Pro Ile Pro Thr Asn Lys Arg His Ala Ala Ala Gln
            100                 105                 110 atc ttt agc aac cct aat gtt gtt gct gaa gtg cca tgg tat gga atc     384
Ile Phe Ser Asn Pro Asn Val Val Ala Glu Val Pro Trp Tyr Gly Ile
        115                 120                 125 gaa caa gaa tac act ctg ttg cag aaa gat gtg aat tgg cct gtc gga     432
Glu Gln Glu Tyr Thr Leu Leu Gln Lys Asp Val Asn Trp Pro Val Gly
    130                 135                 140 tgg ccc att ggt gga ttc ctc ggc cct cag gga cca tac tac tgc agt     480
Trp Pro Ile Gly Gly Phe Leu Gly Pro Gln Gly Pro Tyr Tyr Cys Ser
145                 150                 155                 160 gtt gga gct gac aaa tct ttt gga aga gac att gtt gat gtt cac tac     528
Val Gly Ala Asp Lys Ser Phe Gly Arg Asp Ile Val Asp Val His Tyr
                165                 170                 175 aag gct tgt ttg tat gct gga att aac atc agt gga atc aat gga gaa     576
Lys Ala Cys Leu Tyr Ala Gly Ile Asn Ile Ser Gly Ile Asn Gly Glu
            180                 185                 190 gtc atg cct ggt cag tgg gag ttc caa gtc gga ccg tcg gtt ggt atc     624
Val Met Pro Gly Gln Trp Glu Phe Gln Val Gly Pro Ser Val Gly Ile
        195                 200                 205 tca gct gct gat gaa gtg tgg att gct cgt ttt att ttg gag agg atc     672
Ser Ala Ala Asp Glu Val Trp Ile Ala Arg Phe Ile Leu Glu Arg Ile
    210                 215                 220 aca gag att gct ggt gtg gtt gta tct gtt gac cca aaa cca att ccg     720
Thr Glu Ile Ala Gly Val Val Val Ser Val Asp Pro Lys Pro Ile Pro
225                 230                 235                 240
```

```
ggt gac tgg aac gga gct ggt gct cac acc aat tac agt act aaa tcg      768
Gly Asp Trp Asn Gly Ala Gly Ala His Thr Asn Tyr Ser Thr Lys Ser
            245                 250                 255 atg agg gag gaa gga gga tac gag ata atc aag aag gca att gat aag      816
Met Arg Glu Glu Gly Gly Tyr Glu Ile Ile Lys Lys Ala Ile Asp Lys
        260                 265                 270 ctc gga ctg aga cac aag gag cac att tct gct tac ggt gaa ggc aac      864
Leu Gly Leu Arg His Lys Glu His Ile Ser Ala Tyr Gly Glu Gly Asn
    275                 280                 285 gag cgt cgt ctc act gga cac cat gaa act gct gat atc aac act ttc      912
Glu Arg Arg Leu Thr Gly His His Glu Thr Ala Asp Ile Asn Thr Phe
290                 295                 300 aaa tgg ggt gtt gca aac cgt gga gca tca atc cgt gta gga cgt gac      960
Lys Trp Gly Val Ala Asn Arg Gly Ala Ser Ile Arg Val Gly Arg Asp
305                 310                 315                 320 acg gag aag gaa ggg aaa gga tac ttt gag gat agg agg cca gct tcc     1008
Thr Glu Lys Glu Gly Lys Gly Tyr Phe Glu Asp Arg Arg Pro Ala Ser
                325                 330                 335 aac atg gac cct tac act gta act tcc atg att gca gag act aca ctt     1056
Asn Met Asp Pro Tyr Thr Val Thr Ser Met Ile Ala Glu Thr Thr Leu
            340                 345                 350 ctt tgg aat cct tga                                                  1071
Leu Trp Asn Pro
            355
```

<210> SEQ ID NO 8
<211> LENGTH: 356
<212> TYPE: PRT
<213> ORGANISM: brassica napus

<400> SEQUENCE: 8

Met Ser Leu Leu Thr Asp His Val Asn Leu Asp Leu Ser Asp Asn Thr
1               5                   10                  15

Glu Lys Ile Ile Ala Glu Tyr Ile Trp Val Gly Gly Ser Gly Met Asp
            20                  25                  30

Met Arg Ser Lys Ala Arg Thr Leu Pro Gly Pro Val Thr Asp Pro Ser
        35                  40                  45

Lys Leu Pro Lys Trp Asn Tyr Asp Gly Ser Ser Thr Gly Gln Ala Pro
    50                  55                  60

Gly Glu Asp Ser Glu Val Ile Leu Tyr Pro Gln Ala Ile Phe Lys Asp
65                  70                  75                  80

Pro Phe Arg Arg Gly Asn Asn Ile Leu Val Met Cys Asp Thr Tyr Thr
                85                  90                  95

Pro Ala Gly Glu Pro Ile Pro Thr Asn Lys Arg His Ala Ala Ala Gln
            100                 105                 110

Ile Phe Ser Asn Pro Asn Val Val Ala Glu Val Pro Trp Tyr Gly Ile
        115                 120                 125

Glu Gln Glu Tyr Thr Leu Leu Gln Lys Asp Val Asn Trp Pro Val Gly
    130                 135                 140

Trp Pro Ile Gly Gly Phe Leu Gly Pro Gln Gly Pro Tyr Tyr Cys Ser
145                 150                 155                 160

Val Gly Ala Asp Lys Ser Phe Gly Arg Asp Ile Val Asp Val His Tyr
                165                 170                 175

Lys Ala Cys Leu Tyr Ala Gly Ile Asn Ile Ser Gly Ile Asn Gly Glu
            180                 185                 190

Val Met Pro Gly Gln Trp Glu Phe Gln Val Gly Pro Ser Val Gly Ile
        195                 200                 205

```
Ser Ala Ala Asp Glu Val Trp Ile Ala Arg Phe Ile Leu Glu Arg Ile
    210                 215                 220

Thr Glu Ile Ala Gly Val Val Ser Val Asp Pro Lys Pro Ile Pro
225                 230                 235                 240

Gly Asp Trp Asn Gly Ala Gly Ala His Thr Asn Tyr Ser Thr Lys Ser
                245                 250                 255

Met Arg Glu Glu Gly Tyr Glu Ile Ile Lys Lys Ala Ile Asp Lys
            260                 265                 270

Leu Gly Leu Arg His Lys Glu His Ile Ser Ala Tyr Gly Glu Gly Asn
        275                 280                 285

Glu Arg Arg Leu Thr Gly His His Glu Thr Ala Asp Ile Asn Thr Phe
    290                 295                 300

Lys Trp Gly Val Ala Asn Arg Gly Ala Ser Ile Arg Val Gly Arg Asp
305                 310                 315                 320

Thr Glu Lys Glu Gly Lys Gly Tyr Phe Glu Asp Arg Arg Pro Ala Ser
                325                 330                 335

Asn Met Asp Pro Tyr Thr Val Thr Ser Met Ile Ala Glu Thr Thr Leu
            340                 345                 350

Leu Trp Asn Pro
        355

<210> SEQ ID NO 9
<211> LENGTH: 777
<212> TYPE: DNA
<213> ORGANISM: Arabidopsis

<400> SEQUENCE: 9
cccgtcgtgc ccggaccctg tcgcaccacg aggcgctgtc tacgagtcgg gttgtttggg      60
aatgcagccc caatcgggcg gtaaattccg tccaaggcta atacgggcg agagaccgat      120 agcgaacaag taccgcgagg taaagatgaa aaggactttg aaaagagagt caaagagtgc      180
ttgaaattgt cgggagggaa gcggatgggg ccggcgatg cgtcctggtc ggatgcggaa      240
cggagcaatc cggtccgccg atcgattcgg ggcgtggacc gacgcggatt acggtggcgg      300
cctaagcccg gcttttgat acgcttgtgg agacgtcgct gccgtgatcg tggtctgcag      360
cacgcgccta acggcgtgcc tcggcatcag cgtgctccgg gcgtcggcct gtgggctccc      420
cattcgaccc gtcttgaaac acggaccaag gagtctgaca tgtgtgcgag tcaacgggtg      480
agtaaacccg taaggcgcaa ggaagctgat tggcgggatc ctcgcgggtg caccgccgac      540
cgaccttgat cttctgagaa gggttcgagt gtgagcatgc ctgtcgggac ccgaaagatg      600
gtgaactatg cctgagcggg gtaaagccag aggaaactct ggtggaagcc cgcagcgata      660
ctgacgtgca aatcgttcgt ctgacttggg tataggggcg aaagactaat cgaaccatct      720
agtagctggt tccctccgaa gtttccctca ggatagctgg agctcggacg cgagttc       777

<210> SEQ ID NO 10
<211> LENGTH: 663
<212> TYPE: DNA
<213> ORGANISM: glycine max

<400> SEQUENCE: 10
cgatagcgaa caagtaccgc gagggaaaga tgaaaaggac tttgaaaaga gagtcaaaga      60
gtgcttgaaa ttgtcgggag ggaagcggat ggggccggc gatgtgtccc ggtcggatgt      120
ggaacggtga gagccggtcc gccgatcgac tcgggacatt gaccgacgcg gattgcgatg      180
gtggcccaag cccgggctgt tgatatgctc gtggagacgt catcatcgcg attgtggatg      240
```

```
gcagcgcgcg cccttggcgt gcctcggcac ctgcgcgctc ctggcgtcgg cctgtgggct    300
ccccattcgg cccgtcttga aacacggacc aaggagtctg acatgtgtgc gagtcaacgg    360
gcgagtaaac ccgtaaggcg caaggaagct gattggtggg atcccctgt gggttgcacc     420 gccgaccgac cctgatcttc tgtgaagggt tcgagtgaga gcatacctgt cgggaccccga   480 aagatggtga actatgcctg agcggggcga agccagagga aactctggtg gaggcccgca    540
gcgatactga cgtgcaaatc gttcgtctga cttgggtata ggggcgaaag actaatcgaa    600
ccgtctagta gctggttccc tccgaagttt ccctcaggat agctggagcc cgcgggcgag    660
ttc                                                                  663
```

```
<210> SEQ ID NO 11
<211> LENGTH: 710
<212> TYPE: DNA
<213> ORGANISM: glycine max

<400> SEQUENCE: 11
ccaatcgggc ggtaaattcc gtccaaggct aaatactggc gagagaccga tagcgaacaa     60
gtaccgcgag ggaaagatga aaaggacttt gaaaagagag tcaaagagtg cttgaaattg    120
tcggagggaa gcggatgggg gccggcgat gtgtcccgt cggatgtgga acggtgagag      180
ccggtccgcc gatcgactcg ggacattgac cgacgcggat tgcgatggtg cccaagccc    240 gggctgttga tatgctcgtg agacgtcat catcgcgatt gtggatggca gcgcgcgccc    300
ttggcgtgcc tcggcacctg cgcgctcctg gcgtcggcct gtgggctccc cattcggccc    360
gtcttgaaac acgaccaag gagtctgaca tgtgtgcgag tcaacgggcg agtaaacccg     420
taaggcgcaa ggaagctgat tggtgggatc ccctgtggg ttgcaccgcc gaccgaccct    480
gatcttctgt gaagggttcg agtgagagca tacctgtcgg gacccgaaag atggtgaact    540
atgcctgagc ggggcgaagc cagaggaaac tctggtggag gcccgcagcg atactgacgt    600
gcaaatcgtt cgtctgactt gggtataggg gcgaaagact aatcgaaccg tctagtagct    660
ggttccctcc gaagtttccc tcaggatagc tggagcccgc gggcgagttc               710
```

```
<210> SEQ ID NO 12
<211> LENGTH: 721
<212> TYPE: DNA
<213> ORGANISM: glycine max
<220> FEATURE:
<221> NAME/KEY: misc_feature
<222> LOCATION: (369)..(370)
<223> OTHER INFORMATION: n is a, c, g, or t

<400> SEQUENCE: 12
cccgtcgtgc ccggaccctg tcgcaccacg aggcgctgtc ggcgagtcgg gttgtttggg     60
aatgcagccc caatcgggcg gtaaattccg tccaaggcta aatactggcg agagaccgat    120
agcgaacaag taccgcgagg gaaagatgaa aaggactttg aaaagagagt caaagagtgc    180
ttgaaattgt cggagggaa gcggatgggg gccggcgatg tgtcccggtc ggatgtggaa     240
cggtgagagc cggtccgccg atcgactcgg acattgacc gacgcggatt gcgatggtgg    300
cccaagcccg ggctgttgat atgctcgtgg agacgtcatc atcgcgattg tggatggcag    360
cgcgcgccnn tggcgtgcct cggcacctgc gcgctcctgg cgtcggcctg tgggctcccc    420
attcggcccg tcttgaaaca cggaccaagg agtctgacat gtgtgcgagt caacgggcga    480
gtaaacccgt aaggcgcaag gaagctgatt ggtgggatcc cctgtgggt tgcaccgccg    540 accgaccctg atcttctgtg aagggttcga gtgagagcat acctgtcggg acccgaaaga    600
```

| | |
|---|---|
| tggtgaacta tgcctgagcg gggcgaagcc agaggaaact ctggtggagg cccgcagcga | 660 |
| tactgacgtg caaatcgttc gtctgacttg ggtataggg cgaaagacta atcgaaccgt | 720 |
| c | 721 |

<210> SEQ ID NO 13
<211> LENGTH: 1190
<212> TYPE: DNA
<213> ORGANISM: Arabidopsis

<400> SEQUENCE: 13

| | |
|---|---|
| cctcgtcatc taattagtga cgcgcatgaa tggattaacg agattcccac tgtccctgtc | 60 |
| tactatccag cgaaaccaca gccaagggaa cgggcttggc agaatcagcg gggaaagaag | 120 |
| accctgttga gcttgactct agtccgactt tgtgaaatga cttgagaggt gtaggataag | 180 |
| tgggagcttc ggcgcaagtg aaataccact acttttaacg ttattttact tactccgtga | 240 |
| atcggaggcc ggggtacaac ccctgttttt ggtcccaagg ctcgcttcgg cgggtcgatc | 300 |
| cgggcggagg acattgtcag gtgggagtt tggctgggc ggcacatctg ttaaaagata | 360 |
| acgcaggtgt cctaagatga gctcaacgag aacagaaatc tcgtgtggaa caaaagggta | 420 |
| aaagctcgtt tgattctgat tttcagtacg aatacgaacc gtgaaagcgt ggcctatcga | 480 |
| tcctttagac ttcggaattt gaagctagag gtgtcagaaa agttaccaca gggataactg | 540 |
| gcttgtggca gccaagcgtt catagcgacg ttgcttttg atccttcgat gtcggctctt | 600 |
| cctatcattg tgaagcagaa ttcaccaagt gttggattgt tcacccacca atagggaacg | 660 |
| tgagctgggt ttagaccgtc gtgagacagg ttagttttac cctactgatg cccgcgtcgc | 720 |
| gatagtaatt caacctagta cgagaggaac cgttgattcg cacaattggt catcgcgctt | 780 |
| ggttgaaaag ccagtggcgc gaagctaccg tgcgctggat tatgactgaa cgcctctaag | 840 |
| tcagaatccg ggctagaagc gacgcatgcg cccgccgccc gattgccgac cctcagtagg | 900 |
| agcttaggct ccaaaggcac gtgtcgttgg ctaagtccgt tcggcggaac ggtcgttcgg | 960 |
| accgccttga attataatta ccaccgagcg gcgggtagaa tcctttgcag acgacttaaa | 1020 |
| tacgcgacgg ggtattgtaa gtggcagagt ggccttgctg ccacgatcca ctgagattca | 1080 |
| gcccttttgtc gctaagattc gaccctcccc taaatcactc caaaaaaaac aatcccccaat | 1140 |
| tctacacaag tgtttctaca ctaacaaagc aacagctcct taacgaattc | 1190 |

<210> SEQ ID NO 14
<211> LENGTH: 1034
<212> TYPE: DNA
<213> ORGANISM: glycine max
<220> FEATURE:
<221> NAME/KEY: misc_feature
<222> LOCATION: (1026)..(1026)
<223> OTHER INFORMATION: n is a, c, g, or t
<220> FEATURE:
<221> NAME/KEY: misc_feature
<222> LOCATION: (1030)..(1030)
<223> OTHER INFORMATION: n is a, c, g, or t

<400> SEQUENCE: 14

| | |
|---|---|
| ggaatcagcg gggaaagaag accctgttga gcttgactct agtccgactt tgtgaaatga | 60 |
| cttgagaggt gtaggataag tgrgagctgg aaacagcgaa agtgaaatac cactactttt | 120 |
| aacgttattt tacttattcc gtgaatcgga agcggggcac tgcccctctt tttggaccca | 180 |
| aggtcggctt cggccggtcg atccgggcgg aagacattgt caggtgggga gtttggctgg | 240 |
| ggcggcacat ctgttaaaag ataacgcagg tgtcctaaga tgagctcaac gagaacagaa | 300 |

```
atctcgtgtg gaacaaaagg gtaaaagctc gtttgattct gatttccagt acgaatacga    360
accgtgaaag cgtggcctat cgatccttta gtccttcgga atttgaagct agaggtgtca    420
gaaaagttac cacagggata actggcttgt ggcagccaag cgttcatagc gacgttgctt    480
tttgatcctt cgatgtcggc tcttcctatc attgtgaagc agaattcacc aagtgttgga    540
ttgttcaccc accaataggg aacgtgagct gggtttagac cgtcgtgaga caggttagtt    600
ttaccctact gatgacagtg tcgcaatagt aattcaacct agtacgagag gaaccgttga    660
ttcgcacaat tggtcatcgc gcttggttga aaagccagtg gcgcgaagct accgtgcgtt    720
ggattatgac tgaacgcctc taagtcagaa tccgggctag aagcgacgcg tgcgcccgcc    780
gtccgtttgc cgaccagcag tagggggcct cggccccccca aaggcacgtg ccgttggtga    840
ccctcgtgag gcggattagc cctacgagac gccttgaagc gcaattccca tcgagcggcg    900
ggtagaatcc tttgcagacg acttaaatac gcgacgggaa gggcgaattc cagcacactg    960
gcggccgtta ctagtggatc cgagctcggt accaagcttg atgcatagct tgagtattct   1020
atagtntcan ccct                                                      1034

<210> SEQ ID NO 15
<211> LENGTH: 1137
<212> TYPE: DNA
<213> ORGANISM: glycine max

<400> SEQUENCE: 15
catctatagt gacgsgcatg aatggatkac gagatsccac tgtccctgtc tactatccag     60
cgaaaccaca gccaagggaa cgggcttggc ggaatcagcg rggaaagaag accctgttga    120
gcttgactct agtccgactt tgtgaaatga cttgagaggt gtaggataag tgggagctgg    180
aaacagcgaa agtgaaatac cactactttt aacgttattt tacttattcc gtgaatcgga    240
agcggggcac tgcccctctt tttggaccca aggtcggctt cggccggtcg atccgggcgg    300
aagacattgt caggtgggga gtttggctgg ggcggcacat ctgttaaaag ataacgcagg    360
tgtcctaaga tgagctcaac gagaacagaa atctcgtgtg gaacaaaagg gtaaaagctc    420
gtttgattct gatttccagt acgaatacga accgtgaaag cgtggcctat cgatccttta    480
gtccttcgga atttgaagct agaggtgtca gaaaagttac cacagggata actggcttgt    540
ggcagccaag cgttcatagc gacgttgctt tttgatcctt cgatgtcggc tcttcctatc    600
attgtgaagc agaattcacc aagtgttgga ttgttcaccc accaataggg aacgtgagct    660
gggtttagac cgtcgtgaga caggttagtt ttaccctact gatgacagtg tcgcaatagt    720
aattcaacct agtacgagag gaaccgttga ttcgcacaat tggtcatcgc gcttggttga    780
aaagccagtg gcgcgaagct accgtgcgtt ggattatgac tgaacgcctc taagtcagaa    840
tccgggctag aagcgacgcg tgcgcccgcc gtccgtttgc cgaccagcag tagggggcct    900 cggccccccca aaggcacgtg ccgttggtga ccctcgtgag gcggattagc cctacgagac    960
gccttgaagc gcaattccca tcgagcggcg ggtagaatcc tttgcagacg acttaaatac   1020 gcgacgggt attgtaagtg gcagaagggc gaattccagc acactggcgg ccgttactag   1080
tggatccgag ctcggtacca agcttgatgc atagcttgag tattctatag ttcacct     1137

<210> SEQ ID NO 16
<211> LENGTH: 6555
<212> TYPE: DNA
<213> ORGANISM: Artificial Sequence
<220> FEATURE:
<223> OTHER INFORMATION: plasmid
```

<400> SEQUENCE: 16

```
agcgcccaat acgcaaaccg cctctccccg cgcgttggcc gattcattaa tgcagctggc    60
acgacaggtt tcccgactgg aaagcgggca gtgagcgcaa cgcaattaat gtgagttagc   120
tcactcatta ggcaccccag gctttacact ttatgcttcc ggctcgtatg ttgtgtggaa   180
ttgtgagcgg ataacaattt cacacaggaa acagctatga ccatgattac gccaagctat   240
ttaggtgacg cgttagaata ctcaagctat gcatcaagct tggtaccgag ctcggatcca   300
ctagtaacgg ccgccagtgt gctggaattc gcccttcccg tcgcgtattt aagtcgtctg   360
caaaggattc tacccgccgc tcgatgggaa ttgcgcttca aggcgtctcg tagggctaat   420
ccgcctcacg agggtcacca acggcacgtg cctttggggg gccgaggccc cctactgctg   480
gtcggcaaac ggacggcggg cgcacgcgtc gcttctagcc cggattctga cttagaggcg   540
ttcagtcata atccaacgca cggtagcttc gcgccactgg cttttcaacc aagcgcgatg   600
accaattgtg cgaatcaacg gttcctctcg tactaggttg aattactatt gcgacactgt   660
catcagtagg gtaaaactaa cctgtctcac gacggtctaa acccagctca cgttccctat   720
tggtgggtga acaatccaac acttggtgaa ttctgcttca caatgatagg aagagccgac   780
atcgaaggat caaaaagcaa cgtcgctatg aacgcttggc tgccacaagc cagttatccc   840
tgtggtaact tttctgacac ctctagcttc aaattccgaa ggactaaagg atcgataggc   900
cacgctttca cggttcgtat tcgtactgga aatcagaatc aaacgagctt ttacccttt    960
gttccacacg agatttctgt tctcgttgag ctcatcttag gacacctgcg ttatcttta   1020
acagatgtgc cgcccagcc aaactcccca cctgacaatg tcttccgccc ggatcgaccg   1080
gccgaagccg accttgggtc caaaaagagg ggcagtgccc cgcttccgat tcacggaata   1140
agtaaaataa cgttaaaagt agtggtattt cactttcgct gtttccagct cccacttatc   1200
ctacacctct caagtcattt cmcaaagtcg gactagagtc aagctcaaca gggtcttctt   1260
tccccgctga ttccgccaag cccgttccct tggctgtggt ttcgctggat agtagacagg   1320
gacagtggga atctcgttaa tccattcatg cgcgtcacta attagatgac gaggcatttg   1380
gctaccttaa gagagtcata gttactcccg ccgtttaccc gcgcttggtt gaatttcttc   1440
actttgacat tcagagcact gggcagaaat cacattgcgt caacatccgc agggaccatc   1500
gcaatgcttt gttttaatta aacagtcgga ttcccccttgt ccgtaccagt tctgagttga   1560
ctgttcgacg cccggggaag aggccccgaa gggcccgttc ccaatccgtc ccccgaccgg   1620
cacgcgacga cccgctctcg ccgcggaagc agctcgagca gtccaccgac agccgacggg   1680
ttcgggactg ggaccccggt gcccagccct cagagccaat ccttttcccg aggttacgga   1740
tccattttgc cgacttccct tgcctacatt gttccatcga ccagaggctg ttcaccttgg   1800
agacctgatg cggttatgag tacgaccggg cgtgggaggc actcggtcct ccggattttc   1860
aagggccgcc gggggcgcac cggacaccac gcgacgtgcg gtgctcttcc agccgctgga   1920
ccctacctcc ggctgagccg tttccagggt gggcaggctg ttaaacagaa aagataactc   1980
tttccggggc cccgccgac gtctccggac tccctaacgt tgccgtcagc cgccacgtcc   2040
cggttcagga attttaaccc gattcccttt cggagtacgc gcacagagcg ctatcagacg   2100
ggcttccccc gtcccttagg atcgactaac ccatgtgcaa gtgccgttca catggaacct   2160
ttcccctctt cggccttcaa agttctcatt tgaatatttg ctactaccac caagatctgc   2220
accgacgacc gctccgcccg ggctcgcgcc ctggttttg cagcgaccgc cgcgccctcc   2280
tactcatcgg ggcttggtcc ttgccccgac ggccgggtat aggtcgcgcg ctttagcgcc   2340
```

```
atccattttc ggggctagtt gattcggcag gtgagttgtt acacactcct tagcggattt    2400
sgacttccat gaccaccgtc ctgctgtctt aatcgaccaa caccctttgt ggggtctagg    2460
ttagcgcgca gttgggcacc gtaacccagc ttccggttca tcccgcatcg ccagttctgc    2520
ttaccaaaaa tggcccactt ggagctctcg attccatggc gcggctcaac agagcagccg    2580
caccgtccta cctatttaaa gtttgagaat aggtcgaggg cgttgcgccc ccgatgcctc    2640
taatcattgg ctttacccga tagaactcgc ccgcgggctc cagctatcct gagggaaact    2700
tcggagggaa ccagctacta gacggttcga ttagtctttc gccctatac ccaagtcaga     2760
cgaacgattt gcacgtcagt atcgctgcgg gcctccacca gagtttcctc tggcttcgcc    2820
ccgctcaggc atagttcacc atctttcggg tcccgacagg tatgctctca ctcgaaccct    2880
tcacagaaga tcagggtcgg tcggcggtgc aacccacagg gggatcccac caatcagctt    2940
ccttgcgcct tacgggttta ctcgcccgtt gactcgcaca catgtcagac tccttggtcc    3000
gtgtttcaag acgggccgaa tgggagcccc acaggccgac gccaggagcg cgcaggtgcc    3060
gaggcacgcc aagggcgcgc gctgccatcc acaatcgcga tgatgacgtc tccacgagca    3120
tatcaacagc ccgggcttgg gccaccatcg caatccgcgt cggtcaatgt cccgagtcga    3180
tcggcggacc ggctctcacc gttccacatc cgaccggac acatcgccgg cccccatccg     3240
cttccctccc gacaatttca agcactcttt gactctcttt tcaaagtcct tttcatcttt    3300
ccctcgcggt acttgttcgc tatcggtctc tcgccagtat ttagccttgg acggaattta    3360
ccgcccgatt ggaagggcga attctgcaga tatccatcac actggcggcc gctcgagcat    3420
gcatctagag ggcccaattc gccctatagt gagtcgtatt acaattcact ggccgtcgtt    3480
ttacaacgtc gtgactggga aaaccctggc gttacccaac ttaatcgcct tgcagcacat    3540
ccccctttcg ccagctggcg taatagcgaa gaggcccgca ccgatcgccc ttcccaacag    3600
ttgcgcagcc tatacgtacg gcagtttaag gtttacacct ataaagaga gagccgttat     3660
cgtctgtttg tggatgtaca gagtgatatt attgacacgc cggggcgacg gatggtgatc    3720
cccctggcca gtgcacgtct gctgtcagat aaagtctccc gtgaacttta cccggtggtg    3780
catatcgggg atgaaagctg cgcatgatg accaccgata tggccagtgt gccggtctcc     3840
gttatcgggg aagaagtggc tgatctcagc caccgcgaaa atgacatcaa aaacgccatt    3900
aacctgatgt tctggggaat ataaatgtca ggcatgagat tatcaaaaag gatcttcacc    3960
tagatccttt tcacgtagaa agccagtccg cagaaacggt gctgaccccg gatgaatgtc    4020
agctactggg ctatctggac aagggaaaac gcaagcgcaa agagaaagca ggtagcttgc    4080
agtgggctta catggcgata gctagactgg gcggttttat ggacagcaag cgaaccggaa    4140
ttgccagctg gggcgccctc tggtaaggtt gggaagccct gcaaagtaaa ctggatggct    4200
ttctcgccgc caaggatctg atggcgcagg ggatcaagct ctgatcaaga acaggatga    4260
ggatcgtttc gcatgattga acaagatgga ttgcacgcag gttctccggc cgcttgggtg    4320
gagaggctat tcggctatga ctgggcacaa cagacaatcg gctgctctga tgccgccgtg    4380
ttccggctgt cagcgcaggg gcgcccggtt ctttttgtca agaccgacct gtccggtgcc    4440
ctgaatgaac tgcaagacga ggcagcgcgg ctatcgtggc tggccacgac gggcgttcct    4500
tgcgcagctg tgctcgacgt tgtcactgaa gcgggaaggg actggctgct attgggcgaa    4560
gtgccggggc aggatctcct gtcatctcac cttgctcctg ccgagaaagt atccatcatg    4620
gctgatgcaa tgcggcggct gcatacgctt gatccggcta cctgcccatt cgaccaccaa    4680
gcgaaacatc gcatcgagcg agcacgtact cggatggaag ccggtcttgt cgatcaggat    4740
```

| | |
|---|---:|
| gatctggacg aagagcatca ggggctcgcg ccagccgaac tgttcgccag gctcaaggcg | 4800 |
| agcatgcccg acggcgagga tctcgtcgtg acccatggcg atgcctgctt gccgaatatc | 4860 |
| atggtggaaa atggccgctt ttctggattc atcgactgtg gccggctggg tgtggcggac | 4920 |
| cgctatcagg acatagcgtt ggctacccgt gatattgctg aagagcttgg cggcgaatgg | 4980 |
| gctgaccgct tcctcgtgct ttacggtatc gccgctcccg attcgcagcg catcgccttc | 5040 |
| tatcgccttc ttgacgagtt cttctgaatt attaacgctt acaatttcct gatgcggtat | 5100 |
| tttctcctta cgcatctgtg cggtatttca caccgcatac aggtggcact tttcggggaa | 5160 |
| atgtgcgcgg aaccctatt tgtttatttt tctaaataca ttcaaatatg tatccgctca | 5220 |
| tgagacaata accctgataa atgcttcaat aatagcacgt gaggagggcc accatggcca | 5280 |
| agttgaccag tgccgttccg gtgctcaccg cgcgcgacgt cgccgagcg gtcgagttct | 5340 |
| ggaccgaccg gctcgggttc tcccgggact tcgtggagga cgacttcgcc ggtgtggtcc | 5400 |
| gggacgacgt gaccctgttc atcagcgcgg tccaggacca ggtggtgccg gacaacaccc | 5460 |
| tggcctgggt gtgggtgcgc ggcctggacg agctgtacgc cgagtggtcg gaggtcgtgt | 5520 |
| ccacgaactt ccgggacgcc tccgggccgg ccatgaccga gatcggcgag cagccgtggg | 5580 |
| ggcgggagtt cgccctgcgc gacccggccg gcaactgcgt gcacttcgtg gccgaggagc | 5640 |
| aggactgaca cgtgctaaaa cttcattttt aatttaaaag gatctaggtg aagatccttt | 5700 |
| ttgataatct catgaccaaa atcccttaac gtgagttttc gttccactga gcgtcagacc | 5760 |
| ccgtagaaaa gatcaaagga tcttcttgag atcctttttt tctgcgcgta atctgctgct | 5820 |
| tgcaaacaaa aaaaccaccg ctaccagcgg tggtttgttt gccggatcaa gagctaccaa | 5880 |
| ctcttttcc gaaggtaact ggcttcagca gagcgcagat accaaatact gtccttctag | 5940 |
| tgtagccgta gttaggccac cacttcaaga actctgtagc accgcctaca tacctcgctc | 6000 |
| tgctaatcct gttaccagtg gctgctgcca gtggcgataa gtcgtgtctt accgggttgg | 6060 |
| actcaagacg atagttaccg gataaggcgc agcggtcggg ctgaacgggg ggttcgtgca | 6120 |
| cacagcccag cttggagcga acgacctaca ccgaactgag atacctacag cgtgagctat | 6180 |
| gagaaagcgc cacgcttccc gaagggagaa aggcggacag gtatccggta agcggcaggg | 6240 |
| tcggaacagg agagcgcacg agggagcttc caggggggaaa cgcctggtat ctttatagtc | 6300 |
| ctgtcgggtt tcgccacctc tgacttgagc gtcgattttt gtgatgctcg tcagggggc | 6360 |
| ggagcctatg gaaaaacgcc agcaacgcgg cctttttacg gttcctgggc ttttgctggc | 6420 |
| cttttgctca catgttcttt cctgcgttat cccctgattc tgtggataac cgtattaccg | 6480 |
| cctttgagtg agctgatacc gctcgccgca gccgaacgac cgagcgcagc gagtcagtga | 6540 |
| gcgaggaagc ggaag | 6555 |

<210> SEQ ID NO 17
<211> LENGTH: 4155
<212> TYPE: DNA
<213> ORGANISM: maize

<400> SEQUENCE: 17

| | |
|---|---:|
| ggtccggtga agtgttcgga tcgcggcgac ggggcggttc accgccccg acgtcgcgag | 60 |
| aagtccattg aaccttatca tttagaggaa ggagaagtcg taacaaggtt tccgtaggtg | 120 |
| aacctgtgga aggatcattg ccgtgaccct taaacaaaac agaccgcgaa cgagtcaccc | 180 |
| gtgccgccgg gctccgggcc ggcacgctgc ccccccccc cgaaccttcc cgcggggaag | 240 |
| ggggggccg cgaaaaagaa cccacgcgcc ccgggcgcca aggaacacca gtactacctc | 300 |

-continued

```
ctgcccgcgg agcggtcggc ccgccttccg ctccccgggc agcggttaca ccttaatcga    360
cacgactctc ggcaacggat atctcggtct cgcatcgatg aagaacgtag caaaatgcga    420
tacctggtgt gaatgcagaa tcccgcgaac catcgagttt ttgaacgcaa gttgcgcccg    480
aagccttctg gcggagggca cgtctgcctg ggcgtcacgc caaaagacac tcccaacacc    540
cccccgcggg gcgagggacg tggcgtctgg ccccccgcgc cacagggcga ggtgggccga    600
agcaggggct gccggcgaac cgcgccgggc gcagcacatg gtgggcgaca tcaagttgtt    660
ctcggtgcag cgtcccggcg cgcggccgcc attcggccct aaggacccat cgagcgaccg    720
agcttgccct cggaccgcga ccccaggtca gtcgggacta cccgctgagt ttaagcatat    780
aaataagcgg aggagaagaa acttacgagg attcccctag taacggcgag cgaaccggga    840
gcagcccagc ttgagaatcg gcggccttc gccgcccgaa ttgtaagtct ggagaggcgt    900
cctcagcgac ggaccgggcc caagttctct ggaaagggac gcctgggagg gtgagagccc    960
cgtccggccc ggaccctatc gcaccacgag gcgccatcaa cgagtcgggt tgtttgggaa   1020
tgcagcccaa atcgggcggt aaactccgtc caaggctaaa tacaggcgag agaccgatag   1080
cgaacaagta ccgcgaggga agatgaaaa ggactttgaa aagagagtca aagagtgctt   1140
gaaattgccg ggagggaagc ggatgggggc tggcgacgcg ccccgccgt atgcggaacg   1200 gctcctgctg gtccgccgat cggctcgggg cgtggaccgt tgtcgcccgc gctggcggcc   1260
aaagcccggg ggccctaggc gccccggca gccgtcgtcg gcgcggacgg tatccgcgcg   1320
cctctggcgc ccctcggggc gctacgccgc aacggcctgc gagctcccca tccgacccgt   1380
cttgaaacac ggaccaagga gtctgacatg cgtgcgagtc gacgggttca gaaacctgag   1440
atgcgcaagg aagctgacga gcgggaggcc ctcacgagcc gcaccgctgg ccgaccctga   1500
tcttctgtga agggttcgag ttggagcact cctgtcggga cccgaaagat ggtgaactat   1560
gcctgagcgg ggcgaagcca gaggaaactc tggtggaggc tcgaagcgat actgacgtgc   1620
aaatcgttcg tctgacttgg gtatagggc gaaagactaa tcgaaccatc tagtagctgg   1680
ttccctccga agtttccctc aggatagctg gagcccacac gagttctatc gggtaaagcc   1740
aatgattaga ggcatcaggg gcgcaacgcc ctcgacctat tctcaaactt taaataggta   1800
ggacggcgcg gctgcttcgg tgagccgtgc cacggaatcg ggagctccaa gtgggccatt   1860
tttggtaagc agaactggcg atgcgggatg aaccggaagc cgggttacgg tgccaaactg   1920
cgcgctaacc tagaacccac aaagggtgtt ggtcgattaa gacagcagga cgatggtcat   1980
ggaagtcgaa atccgctaag gagtgtgtaa caactcacct gccgaatcaa ctagccccga   2040
aaatggatgg cgctgaagcg cgcgacccac accggccat ctgggcgagc gacatgcccc   2100
gatgagtagg agggcgcacg gccgccgcaa aacccgggc gcgagcccgg gcggagcggc   2160
cgtcggtgca gatcttggtg gtagtagcaa atattcaaat gagaactttg aaggccgaag   2220
aggagaaagg ttccatgtga acggcacttg cacatgggta agccgatcct aagggacggg   2280
ggaaacccgg cagatagcgc gatcacgcgc gtcacccgaa agggaatcgg gttaagattt   2340
cccgagccgg gacgtggcgg cagacggcga cgttaggaag tccggagacg ccggcggggg   2400
cctcgggaag agttatcttt tctgcttaac ggcccgccaa ccctggaatc ggttcagccg   2460
gaggtagggt ccagcggccg gaagagcacc gcacatcgcg tggtgtccgg tgcgcccccg   2520
gcggcccttg aaaatccgga ggaccgaata ccatccacgc ccggtcgtac tcataaccga   2580
atcaggtctc caaggtgaac agacctctgg ccaatggaac aatgtaggca agggaagtcg   2640
gcaaaacgga tccgtaactt cgggaaaagg attggctctg agggttgggc tcggggggtcc   2700
```

```
cggccccgaa cccgtcggct gctggcggaa tgctcgagct gctcgcgcgg cgagagcggg    2760
ccgccgcgtg ccggccgggg gacggaccgg gaacggcccc ctcggggggcc ttccccgggc   2820 gtcgaacaac cgactcagaa ctggtacgga caagggggaat ccgactgttt aattaaaaca   2880
aagcattgcg acggtcctcg aggatgctga cgcaatgtga tttctgccca gtgctctgaa    2940
tgtcaaagtg aagaaattca accaagcgcg ggtaaacgac gggagtaact atgactctct    3000
taaggtacca aatgcctcgt catctaatta gtgacgcgca tgaatggatt aacgagattc    3060
ccactgtccc tgtctactat ccagcgaaac catagccaag ggaacgggct tggcggaatc    3120
agcggggaaa gaagaccctg ttgagcttga ctctagtccg actttgtgaa atgacttgag    3180
aggtgtagga taagtgggag cctccgggcg caagtgaaat accactactt ttaacgttat    3240
tttacttatt ccgtgggtcg gaagcggggc accgcccctc cttttggctc caaggcccgg    3300
cctcgccggg ccaatccggg cggaagacat tgtcaggtgg ggagtttggc tggggcggca    3360
catctgttaa aagataacgc aggtgtccta agatgagctc aacgagaaca gaaatctcgt    3420
gtggaacaaa gggttaaagc tcgtttgatt ctgatttcca gtacgaatac gaaccatgaa    3480
agcgtggcct atcgatcctt tagaccttcg gagtttgaag ctagaggtgt cataaaagtt    3540
accacaggga taactggctt gtggcagcca agcgttcata gcgacgttgc tttttgatcc    3600
ttcgatgtcg gctcttccta tcattgtgaa gcagaattca ccaagtgttg gattgttcac    3660
ccaccaatag ggaacgtgag ctgggtttag accgtcgtga gacaggttag ttttacccta    3720
ctgatgaccg cgccgcgata gtaattcaac ctagtacgag aggaaccgtt gattcacaca    3780
attggtcatc gcgcttggtt gaaaagccag tggcgcgaag ctaccgtgtg ccggattatg    3840
actgaacgcc tctaagtcag aatccaagct agcaaccggc gcctctgctc gccgcccgcc    3900
ccgacccacg ttagggcgtt cgcgccccaa gggcccgtgc cattggctca gcccgcccgg    3960
ccgacgcgcc gcggcgggcc gcctcgaagc tcccttccca acgggcggcg tgctgaatcc    4020
tttgcagacg acttaaaacg cgacggggca ttgtaagtgg cagagtggcc ttgctgccac    4080
gattccactg agatccagcc ccgcgtcgca cggattcgtc cctcccccca acctacgcac    4140
cggcctagcg accta                                                     4155
```

<210> SEQ ID NO 18
<211> LENGTH: 1512
<212> TYPE: DNA
<213> ORGANISM: maize
<220> FEATURE:
<221> NAME/KEY: misc_feature
<222> LOCATION: (1156)..(1156)
<223> OTHER INFORMATION: n is a, c, g, or t
<220> FEATURE:
<221> NAME/KEY: misc_feature
<222> LOCATION: (1164)..(1164)
<223> OTHER INFORMATION: n is a, c, g, or t
<220> FEATURE:
<221> NAME/KEY: misc_feature
<222> LOCATION: (1224)..(1224)
<223> OTHER INFORMATION: n is a, c, g, or t
<220> FEATURE:
<221> NAME/KEY: misc_feature
<222> LOCATION: (1257)..(1257)
<223> OTHER INFORMATION: n is a, c, g, or t
<220> FEATURE:
<221> NAME/KEY: misc_feature
<222> LOCATION: (1274)..(1274)
<223> OTHER INFORMATION: n is a, c, g, or t
<220> FEATURE:
<221> NAME/KEY: misc_feature
<222> LOCATION: (1284)..(1284)
<223> OTHER INFORMATION: n is a, c, g, or t

```
<220> FEATURE:
<221> NAME/KEY: misc_feature
<222> LOCATION: (1296)..(1296)
<223> OTHER INFORMATION: n is a, c, g, or t
<220> FEATURE:
<221> NAME/KEY: misc_feature
<222> LOCATION: (1302)..(1302)
<223> OTHER INFORMATION: n is a, c, g, or t
<220> FEATURE:
<221> NAME/KEY: misc_feature
<222> LOCATION: (1324)..(1324)
<223> OTHER INFORMATION: n is a, c, g, or t
<220> FEATURE:
<221> NAME/KEY: misc_feature
<222> LOCATION: (1336)..(1336)
<223> OTHER INFORMATION: n is a, c, g, or t
<220> FEATURE:
<221> NAME/KEY: misc_feature
<222> LOCATION: (1356)..(1356)
<223> OTHER INFORMATION: n is a, c, g, or t
<220> FEATURE:
<221> NAME/KEY: misc_feature
<222> LOCATION: (1372)..(1372)
<223> OTHER INFORMATION: n is a, c, g, or t
<220> FEATURE:
<221> NAME/KEY: misc_feature
<222> LOCATION: (1380)..(1380)
<223> OTHER INFORMATION: n is a, c, g, or t
<220> FEATURE:
<221> NAME/KEY: misc_feature
<222> LOCATION: (1385)..(1387)
<223> OTHER INFORMATION: n is a, c, g, or t
<220> FEATURE:
<221> NAME/KEY: misc_feature
<222> LOCATION: (1406)..(1406)
<223> OTHER INFORMATION: n is a, c, g, or t
<220> FEATURE:
<221> NAME/KEY: misc_feature
<222> LOCATION: (1414)..(1414)
<223> OTHER INFORMATION: n is a, c, g, or t
<220> FEATURE:
<221> NAME/KEY: misc_feature
<222> LOCATION: (1437)..(1438)
<223> OTHER INFORMATION: n is a, c, g, or t
<220> FEATURE:
<221> NAME/KEY: misc_feature
<222> LOCATION: (1448)..(1448)
<223> OTHER INFORMATION: n is a, c, g, or t
<220> FEATURE:
<221> NAME/KEY: misc_feature
<222> LOCATION: (1455)..(1455)
<223> OTHER INFORMATION: n is a, c, g, or t
<220> FEATURE:
<221> NAME/KEY: misc_feature
<222> LOCATION: (1462)..(1463)
<223> OTHER INFORMATION: n is a, c, g, or t
<220> FEATURE:
<221> NAME/KEY: misc_feature
<222> LOCATION: (1468)..(1468)
<223> OTHER INFORMATION: n is a, c, g, or t
<220> FEATURE:
<221> NAME/KEY: misc_feature
<222> LOCATION: (1496)..(1496)
<223> OTHER INFORMATION: n is a, c, g, or t

<400> SEQUENCE: 18
ttaaactcct atagggcgaa ttgatttagc ggccgcgaat tcgcccttgc ggaggagaag    60
aaacttacga ggattcccct agtaacggcg agcgaaccgg gagcagccca gcttgagaat   120
cgggcggcct cgccgcccga attgtagtct ggagaggcgt cctcagcgac ggaccgggcc   180
caagttctct ggaaagggac gcctgggagg gtgagagccc cgtccggccc ggaccctgtc   240
gcaccacgag gcgccgtcaa cgagtcgggt tgtttgggaa tgcagcccaa atcgggcggt   300
aaactccgtc caaggctaaa tacaggcgag agaccgatag cgaacaagta ccgcgaggga   360
```

| | |
|---|---|
| aagatgaaaa ggactttgaa aagagagtca aagagtgctt gaaattgccg ggagggaagc | 420 |
| ggatggggc tggcgacgcg caccggccgt atgcggaacg gctcctgctg gtccgccgat | 480 |
| cggctcgggg cgtggaccgt tgtcgcccgc gccggcggcc aaagcccggg ggccctaggc | 540 |
| gcccccggca gccgtcgtcg gcgcggacgg tatccgcgcg cctctggcgc gcccctcggg | 600 |
| gcgctgcgcc gcaacggcct gcgagctccc catccgaccc gtcttgaaac acggaccaag | 660 |
| gagtctgaca tgcgtgcgag tcgacgggtt cagaaacctg agatgcgcaa ggaagctgac | 720 |
| gagcgggagg ccctcacggg ccgcaccgct ggccgaccct gatcttctgt gaagggttcg | 780 |
| agttggagca cgcctgtcgg gacccgaaag atggtgaact atgcctgagc ggggcgaagc | 840 |
| cagaggaaac tctggtggag gctcgaagcg atactgacgt gcaaatcgtt cgtctgactt | 900 |
| gggtataggg gcgaaagact aatcgaacca tctagtagct ggttctctcc gaagtttccc | 960 |
| tcaggatagc tggagcccac acgagttcta tcgggtaaag ccaatgatta gaggcatcgg | 1020 |
| gggcgcaacg ccctcgacct attctcaaac tttaaatagg taggacgcg cggctgcttc | 1080 |
| ggtgagccgt gccacggaat cgggagctcc aagtgggyca tttttggtaa gcagawctgg | 1140 |
| cgatgcggga tgaacncgga agcngggtt acggtgccaa actgcgcgct aayctagawy | 1200 |
| ycacaaaggg tgttggtcga ttangacagc asgacggtgr tcatgcagtc gaaatcngct | 1260 |
| amgagtgtgt acanctcatc tgcngatcac tagccncgaa antggatggc gctgagcgcg | 1320 |
| cgantcacac tcggtnatct gggcgagcga catgcntcga tgagtaggag gncgcggcgn | 1380 |
| gcgcnnnaat cggggcgcga gccggncggr mgmncgtcgg gcgatcttgt gkwgtannca | 1440 |
| atatycantg aaacnttgma gnncgaangg aarktcatgt gacgscctkk ccatgntwrc | 1500 |
| gatctaggac gg | 1512 |

```
<210> SEQ ID NO 19
<211> LENGTH: 1390
<212> TYPE: DNA
<213> ORGANISM: maize
<220> FEATURE:
<221> NAME/KEY: misc_feature
<222> LOCATION: (29)..(31)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (43)..(45)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (133)..(133)
<223> OTHER INFORMATION: n is a, c, g, or t
```

<400> SEQUENCE: 19

```
atgctcgrct gctcgcgcgr cgagagcgnn ngccgcnygc gtnnncgggg acgamcggga      60
cganccctc nggacntycc crggcgtcga caccgactca gnactggtac ggacamgrga     120
atccgactgt ttnattaaac aaagcattgc gacggtcctc gaggatgctg acgcaatgtg    180
atttctgccc agtgctctga atgtcaaagt gaagaaattc aaccaagcgc grgtaaacgg    240
cgggagtaac tatgactctc ttaaggtagc caaatgcctc gtcatctaat tagtgacgcg    300
catgaatgga ttaacgagat tcccactgtc cctgtctact atccagcgaa accacagcca    360
agggaacggg cttggcggaa tcagcgrgga aagaagaccc tgttgagctt gactctagtc    420
cgactttgtg aaatgacttg agaggtgtag gataagtggg agcctccggg cgcaagtgaa    480
ataccactac ttttaacgtt attttactta ttccgtgggt cggaagcggg gcaccgcccc    540
tccttttggc tccaaggccc ggcctcgccg ggccgatccg ggcggaagac attgtcaggt    600
ggggagtttg gctggggcgg cacatctgtt aaaagataac gcaggtgtcc taagatgagc    660
tcaacgagaa cagaaatctc gtgtggaaca aaagggtaaa agctcgtttg attctgattt    720
ccagtacgaa tacgaaccgt gaaagcgtgg cctatcgatc ctttagacct tcggagtttg    780
aagctagagg tgtcagaaaa gttaccacag ggataactgg cttgtggcag ccaagcgttc    840
atagcgacgt tgcttttga tccttcgatg tcggctcttc ctatcattgt gaagcagaat    900
tcaccaagtg ttggattgtt cacccaccaa tagggaacgt gagctgggtt tagaccgtcg    960
tgagacaggt tagttttacc ctactgatga ccgcgccgcg atagtaattc aacctagtac   1020
gagaggaacc gttgattcac acaattggtc atcgcgcttg gttgaaaagc cagtggcgcg   1080
aagctaccgt gtgccggatt atgactgaac gcctctaagt cagaatccaa gctagcaacc   1140
ggcgcctctg ctcgccgccc gccccgaccc acgttagggc gttcgcgccc caagggcccg   1200
tgccattggc tcagcccgcc cggccgacgc gccgcggcgg gccgcctcga agctcccttc   1260
ccaacgggcg gcgtgctgaa tcctttgcag acgacttaaa acgcgacggg gcattgtaag   1320
tggcagagtg gaagggcgaa ttcgtttaaa cctgcaggac tagtcccttt agtgaggbtt   1380
aattckgagg                                                           1390
```

<210> SEQ ID NO 20
<211> LENGTH: 41
<212> TYPE: DNA
<213> ORGANISM: Artificial
<220> FEATURE:
<223> OTHER INFORMATION: attB

<400> SEQUENCE: 20

```
agcttgaagc ctgctttttt atactaactt gagcgaatgc a                         41
```

<210> SEQ ID NO 21
<211> LENGTH: 33
<212> TYPE: DNA
<213> ORGANISM: Artificial
<220> FEATURE:
<223> OTHER INFORMATION: attB

<400> SEQUENCE: 21

```
ttcgctcaag ttagtataaa aaagcaggct tca                                  33
```

<210> SEQ ID NO 22
<211> LENGTH: 14
<212> TYPE: DNA
<213> ORGANISM: Artificial

```
<220> FEATURE:
<223> OTHER INFORMATION: oligo

<400> SEQUENCE: 22
cgcggccgcg gtac                                                        14

<210> SEQ ID NO 23
<211> LENGTH: 24
<212> TYPE: DNA
<213> ORGANISM: Artificial
<220> FEATURE:
<223> OTHER INFORMATION: primer

<400> SEQUENCE: 23
ctcgagatga gtcttctgac cgat                                             24

<210> SEQ ID NO 24
<211> LENGTH: 21
<212> TYPE: DNA
<213> ORGANISM: Artificial
<220> FEATURE:
<223> OTHER INFORMATION: primer

<400> SEQUENCE: 24
ctcgagtcaa ggattccaaa g                                                21

<210> SEQ ID NO 25
<211> LENGTH: 20
<212> TYPE: DNA
<213> ORGANISM: Cauliflower mosaic virus

<400> SEQUENCE: 25
cagcgtgtcc tctccaaatg                                                  20

<210> SEQ ID NO 26
<211> LENGTH: 20
<212> TYPE: DNA
<213> ORGANISM: Cauliflower mosaic virus

<400> SEQUENCE: 26
agcacgacac tctcgtctac                                                  20

<210> SEQ ID NO 27
<211> LENGTH: 18
<212> TYPE: DNA
<213> ORGANISM: glycine max

<400> SEQUENCE: 27
cgatagcgaa caagtacc                                                    18

<210> SEQ ID NO 28
<211> LENGTH: 18
<212> TYPE: DNA
<213> ORGANISM: glycine max

<400> SEQUENCE: 28
ctgccactta caataccc                                                    18

<210> SEQ ID NO 29
<211> LENGTH: 19
<212> TYPE: DNA
<213> ORGANISM: glycine max
```

```
<400> SEQUENCE: 29
ccaatcgggc ggtaaattc                                                      19

<210> SEQ ID NO 30
<211> LENGTH: 19
<212> TYPE: DNA
<213> ORGANISM: glycine max

<400> SEQUENCE: 30
cccgtcgcgt atttaagtc                                                      19

<210> SEQ ID NO 31
<211> LENGTH: 20
<212> TYPE: DNA
<213> ORGANISM: zea mays

<400> SEQUENCE: 31
ccgtccaagg ctaaatacag                                                     20

<210> SEQ ID NO 32
<211> LENGTH: 20
<212> TYPE: DNA
<213> ORGANISM: zea mays

<400> SEQUENCE: 32
gaggcgttca gtcataatcc                                                     20

<210> SEQ ID NO 33
<211> LENGTH: 21
<212> TYPE: DNA
<213> ORGANISM: zea mays

<400> SEQUENCE: 33
gcggaggaga agaaacttac g                                                   21

<210> SEQ ID NO 34
<211> LENGTH: 21
<212> TYPE: DNA
<213> ORGANISM: zea mays

<400> SEQUENCE: 34
ccactctgcc acttacaatg c                                                   21
```

PRODUCTION OF MODIFIED FATTY ACIDS IN PLANTS THROUGH RDNA TARGETED INTEGRATION OF HETEROLOGOUS GENES

CROSS-REFERENCE TO RELATED APPLICATIONS

This application is a continuation of U.S. application Ser. No. 14/024,220, filed Sep. 11, 2013, which is a continuation of U.S. application Ser. No. 12/571,012, filed Sep. 30, 2009, which claims the benefit of Provisional Application No. 61/102,509, filed Oct. 3, 2008, all of which are expressly incorporated herein by reference in their entirety.

STATEMENT REGARDING SEQUENCE LISTING

The sequence listing associated with this application is provided in text format in lieu of a paper copy and is hereby incorporated by reference into the specification. The name of the text file containing the sequence listing is 56818_Sequence_Final_2016-09-01.txt. The text file is 49 KB; was created on Sep. 1, 2016; and is being submitted via EFS-Web with the filing of the specification.

FIELD OF THE INVENTION

The present invention relates generally to the fields of plants and protein production in plants. In particular, the invention relates to the expression of gene products associated with fatty acid metabolism in plants to alter seed oil content and/or composition.

BACKGROUND OF THE INVENTION

Plant lipids play a major role as structural elements in membranes, as cell signalling components and are the basis for petroleum replacement products, such as renewable biofuels. Renewable biofuels require the development of crops and plant species with high yields of appropriate feedstocks, for example those producing very long chain fatty acids (VLCFAs), and especially unsaturated VLCFAs. Alternatively some specifications may call for short chain fatty acids or fatty acids that have specific functional groups such as an epoxy group, an alcohol group or an acetylene bond, to name a few. All of these specialized fatty acids may be produced by introduction of one or more enzymes capable of modifying fatty acid metabolism and/or biosynthesis to produce the desired compounds.

There are few documented cases of using transgenic means to increase the oil content of Very Long Chain Fatty Acids (VLCFA) in plants. Increases in the proportion of some fatty acids for edible oils have been observed by the introduction of various plant fatty acid biosynthesis and acyltransferase genes in oilseeds. Some examples of such processes are reported in Voelker at al., Science, 257: 72-74, 1992; Voelker et al. The Plant Journal, 9: 229-241, 1996; Lassner et al. The Plant Cell, 8:281-292, 1996; and Millar and Kunst. Plant J, 12: 121-131, 1997).

Knutzon et al. (Proc. Nat'l Acad. Sci. USA, 89: 2624-2628, 1992) reported increased stearic acid content in Brassicaceae by expressing an anti-sense construct to the stearoyl-ACP $\Delta 9$ desaturase. Hitz et al. (Proc. 9th International Cambridge Rapeseed Congress UK, pp. 470-472, 1995) reported increased proportions of oleic acid in *B. napus* by co-suppression of plant microsomal FAD2 ($\Delta 12$) desaturase. U.S. Pat. No. 5,824,858 reported increased proportions of 12:0 or 22:1 in the sn-2 position of triacylglycerols (TAGs) in rapeseed by expression of coconut or meadowfoam lyso-phosphatidic acid acyltransferases (LPATs; E.C. 2.3.1.51, respectively). Lassner et al. (The Plant Cell, 8: 281, 1996) and U.S. Pat. No. 5,445,947 reported increased levels of erucic acid in low erucic acid *B. napus* (canola) cultivars expressing a Jojoba "elongase" 3-keto-acyl-CoA synthase gene; however, the effect following elongase expression in high erucic acid cultivars was negligible, suggesting a metabolic limit.

The contributions of fatty acid elongase FAE1 and yeast L-Phosphatidyl Acyl transferase SLC1 on the fatty acid erucic acid have been separately assessed in transgenic plants (Katavic at al. Biochem Soc Trans, 28: 935-938, 2000; Katavic et al. Crop Science, 41: 739-747, 2001). Further, Mietkiewska at al. (Plant Physiology, 136: 2665, 2004; and U.S. Pub. No.: 20070204370) observed modified oil profiles and VLCFA composition in transgenic *Brassica* expressing a Nasturtium FAE1 gene.

The above reports demonstrated single gene transformations that only modified oil profiles by a few percent and no commercially relevant plant variety has resulted. Further the reports relied on plant transformation using *Agrobacterium*, with its inherent limitations, such as low copy number random integration of the transgene into the plant cell genome.

Modification of plant fatty acids or oils is an important goal, as many plant species, including crops, oilseed crops and algae species are considered as important sources of fatty acids for renewable fuels and feedstock sources for the manufacture of goods.

SUMMARY OF THE INVENTION

In one aspect, the invention provides a method for producing a transgenic plant, comprising:
(a) Co-Transforming Plant Cells with:
   i. a first nucleic acid, said first nucleic acid comprising a nucleotide sequence of at least contiguous 100 nucleotides, said nucleotide sequence possessing at least 50% sequence identity over its entire length to a native ribosomal DNA (rDNA) sequence of said plant cells; and
   ii. a second nucleic acid, said second nucleic acid comprising a coding sequence operably linked to one or more regulatory elements for directing expression of said coding sequence in said plant cells;
thereby obtaining transgenic plant cells;
(b) regenerating a plurality of transgenic plants from said transgenic plant cells; and
(c) selecting from said plurality of transgenic plants a transgenic plant wherein said second nucleic acids is stably integrated at or adjacent to rDNA sequences and said second nucleic acid is amplified.

In another aspect, the invention provides a method for producing a transgenic plant or plant cell, comprising:
(a) Co-Transforming Plant Cells with:
   i. a first nucleic acid, said first nucleic acid comprising a nucleotide sequence of at least contiguous 100 nucleotides, said nucleotide sequence possessing at least 50% sequence identity over its entire length to a native ribosomal DNA (rDNA) sequence of said plant cells; and
   ii. a second nucleic acid, said second nucleic acid comprising a coding sequence operably linked to one or more regulatory elements for directing expression of said coding sequence in said plant cells;
thereby obtaining transgenic plant cells;
(b) regenerating a plurality of transgenic plants from said transgenic plant cells; and
(c) selecting from said plurality of transgenic plants a transgenic plant wherein said second nucleic acids is stably integrated at or adjacent to native rDNA of said plant and said second nucleic acid is amplified.

In another aspect, the invention provides a transgenic plant produced by the method described above, or a seed, organ, tissue, part or cell thereof, or a descendant of said plant, seed, organ, tissue, part or cell.

It is noted that a transgenic plant can also comprise a collection of plant cells such as algae.

In another aspect, the invention provides transgenic plant comprising a plurality of nucleic acids heterologous to said plant, each of said nucleic acid comprising a coding sequence operably linked to one or more regulatory elements for directing expression of said coding sequence in said plant, said nucleic acid being stably integrated at or adjacent to native rDNA of said plant, or a seed, organ, tissue, part or cell thereof, or a descendant of said plant, seed, organ, tissue, part or cell.

In another aspect, the invention provides a method for producing oil, said method comprising extracting oil from a transgenic plant as described above.

Other aspects and features of the present invention will become apparent to those of ordinary skill in the art upon review of the following description of specific embodiments of the invention in conjunction with the accompanying figures.

BRIEF DESCRIPTION OF DRAWINGS

FIG. 1: map of plasmid pJHD2-19a

FIG. 2: Upper Panel: map of recombinant plasmid pABI1006. Lower panel: map of recombinant plasmid pABI1007

FIG. 4: Upper panel: map of plasmid pAgIIa. Lower panel: map of pABI1012.

FIG. 6: Napin promoter source: Upper panel: map of pRD400 nFAE1 and lower panel: map of pABI1024

FIG. 7: Upper panel: map of pNap: FAE1/NGKM. Lower panel: map of pABI1020

FIG. 12: Cytology of transformed *Brassica napus* cells comprising multiple copies of heterologous DNA in an rDNA array.

FIG. 13: Seed oil content of *Brassica napus* expressing three heterologous genes for altered fatty acid metabolism (erucic acid content, top panel; fatty acid profile, bottom panel).

FIG. 16: Sequence comparisons of nucleotides and translation products of published and cloned glutamine synthetase genes. [BNGLUTS nucleotide sequence: SEQ ID NO: 5; Contig1.4 nucleotide sequence: SEQ ID NO: 7; BNGLUTS amino acid sequence: SEQ ID NO: 6; GS1.8 amino acid sequence: SEQ ID NO: 8]

FIG. 18: Upper Panel: Callus of transformed *B. napus* containing GS genes (left plate) and control (right plate). Lower Panel: Co-migration of PCR products obtained from transformants and original plasmids.

FIGS. 19A and 19B: FIG. 19A upper panel: Binding positions of both primer pairs within the *Arabidopsis* 26S rDNA gene, and sequence of amplified soy 26S rDNA regions obtained. FIG. 19A lower panel and FIG. 19B: map of plasmid pJHD19a, containing insert of *Arabidopsis* 26S rDNA. [5' end: AT3RRNA: SEQ ID NO: 9; Primer set 1: SEQ ID NO: 10; Primer set 2: SEQ ID NO: 11; AY935814: SEQ ID NO: 12. 3' end: AT3RRNA: SEQ ID NO: 13; Primer set 2: SEQ ID NO: 14; Primer set 1: SEQ ID NO: 15]

FIG. 21: Upper panel: coding sequence for the bacterial Hygromycin resistance (HygR) gene. Middle panel: map of plasmid pABI1012. Lower panel map of pABI1014

FIG. 22: Upper panel: map of plasmid pABI034 and lower panel: map of pABI035

FIGS. 23A-23E: The positions of the primer binding sites within the Maize 26S rDNA sequence (Genbank accession number AJ309824) [SEQ ID NO: 17] are indicated.

FIGS. 24A-24E: Consensus sequences obtained from the 5' and 3' ends of the amplification products compared to the 26S rDNA gene sequence [AJ309824: SEQ ID NO: 17; Maize 26S rD 5' sequences: SEQ ID NO: 18; Maize 26S rD 3' sequences: SEQ ID NO: 19].

FIG. 27: Upper panel: map of intermediate plasmid pattB-BAR and Lower panel: map of plasmid pABI030 containing the actin promoter upstream and in sense orientation with respect to the attB site and HygR gene.

FIG. 28: Upper panel: map of plasmid pZO1016, consisting of a CaMV 35S promoter, alcohol dehydrogenase intron, GUS coding sequence and NOS terminator. Lower panel map of plasmid pABI031 containing the actin promoter upstream and in sense orientation with respect to the attB site and HygR gene.

DETAILED DESCRIPTION OF INVENTION

Figure 1:
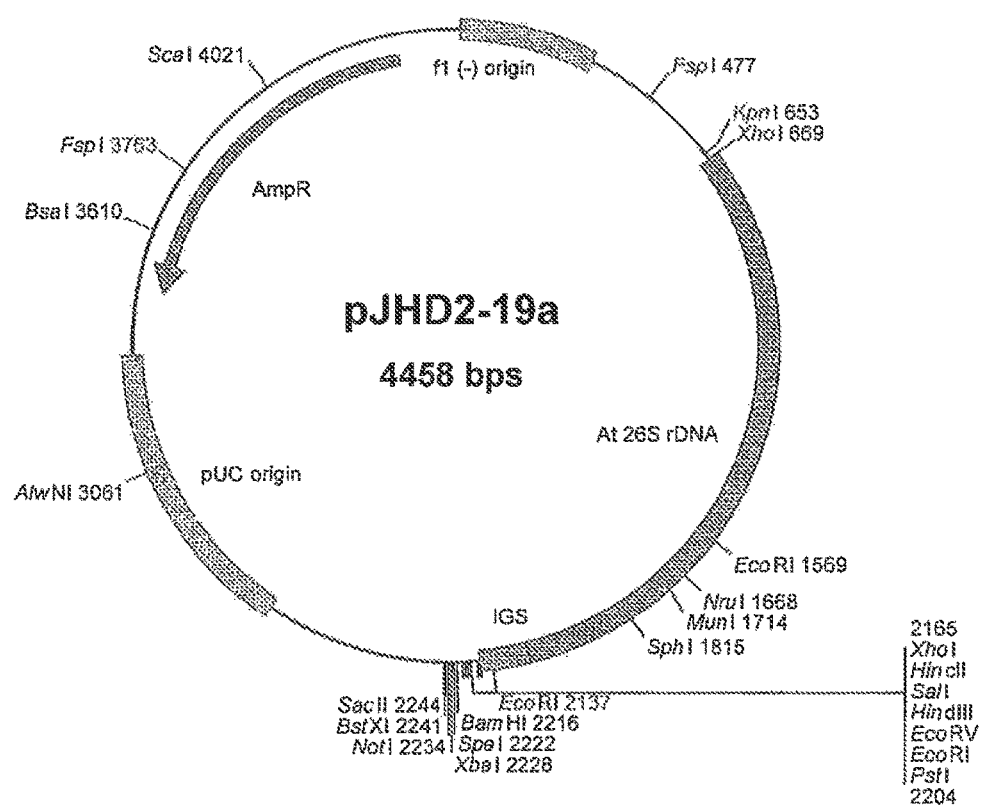

Plant oil biosynthesis involves multiple gene activities that extend beyond the simple synthesis and sequestering of fatty acids. Thus the present invention relates to the introduction of genes encoding products associated with fatty acid metabolism into plant cells to generate plants that produce seed oil with modified fatty acid content. The present invention also relates to modification of any plant cell, including algae cells to produce a modified plant cell with altered fatty acid metabolism and altered fatty acid content.

The present invention also provides methods to introduce nucleic acids into a plant cell in a fashion whereby the placement of said nucleic acids within the chromosomes of a plant is not random, but involves the association of additional nucleic acid sequences. The present invention allows for the introduction of multiple nucleic acids into a plant cell by methods that provide high level gene expression and accommodates multiple copies or sequences of introduced nucleic acids.

The site specific introduction of foreign DNA within a plant genome may be enhanced by homologous recombination (see Offringa et al, U.S. Pat. No. 5,501,967) or by enzyme-mediated site-specific recombination (see Odell et al, U.S. Pat. No. 5,658,772). In Offringa, part of a recombinant DNA containing T-DNA sequences is introduced into a plant by *Agrobacterium* mediated delivery and integrates into the plant genome by homologous recombination. This method requires knowledge of the region of the genome that will be the target for homologous recombination, and requires a selection scheme to identify such rare events. The approach of Odell is based on site specific recombination of new DNA sequences into a region of a plant genome, where recombination sites for recombinase enzymes such as CRE or FLP were previously inserted into a genome to provide a target for recombinase mediated gene delivery, typically by a random *Agrobacteria*-mediated process (see U.S. Pat. Nos. 5,929,301 and 6,445,315, CA 2306053; and WO 9206205). The efficiency of these approaches is generally poor. There is no teaching on how to insert multiple copies of a gene into a pre-determined region of a chromosome. Moreover there is no teaching on how to select a chromosomal location a priori that supports high level gene expression and accommodates multiple copies of a heterologous gene.

While a single transgene may provide a new trait that breeds as a single Mendelian trait, attempts to obtain multiple inserts of a transgene, for example, where a large amount of transgene expression is required, will lead to complexities for plant breeding, such as unstable gene expression (e.g. by gene silencing). Further, multiple gene insertions are typically scattered throughout the plant genome thus making breeding of multigenic insertions difficult, if not impossible. Methods of single gene insertion are routine in the art, however, their limitations are clear. The most significant limitation is that any gene insertion via Agrobacterial or biolistic vehicles is a random event, and cannot reliably target specific regions of a plant genome. Further, when genes are so integrated, their expression levels often vary over time. Thus, there is a need for a method to introduce multiple gene activities into a plant genome in a fashion that enables strong gene expression, precise localization to a preferred genomic region and linkage of said genes in a single locus so that they behave as a single genetic locus upon crossing and breeding.

It is known in the art that introduction of DNA into specific regions of a chromosome may lead to significant alterations to its structure. Hadlazcky (U.S. Pat. No. 6,077, 697) described satellite artificial chromosomes (SATACs) in plants and animals. In particular, the introduction of a "targeting" DNA sequence that "targets" the heterologous DNA to the pericentric heterochromatin caused large-scale amplification resulting in "sausage" chromosomes, "gigachromosomes" and "megachromosomes". As one object of plant breeding is to avoid significant changes to the plant genome, chromosomal alterations are typically not desired for many purposes. For many applications of crop development, the object for introduction of new genes is to select plant lines where the gene introduction process produces crops with inserted genes that do not demonstrate deleterious rearrangements. Further, the target DNA (i.e. rDNA) may be localized to pericentric heterochromatin in some species but not others.

In the context of the present invention, the integration of a heterologous DNA into or adjacent to an rDNA region may lead to novel and beneficial chromosome structures, where DNA is integrated at a single rDNA region or rDNA array in a single plant chromosome, that may include large scale amplification. For example, large scale amplification of integrated sequences may result in 2, 3, 4, 5, 10 or more copies of the core vector, separated by fairly large tracts of intervening rDNA but lying within the confines of one nuclear organization region (NOR) domain.

As used herein, the locus of gene insertion may be considered an "Engineered Trait Loci" or "ETL". It is also found that transformed plant cells of the present invention have a small number of substantially identical copies of heterologous DNA present in a subset of the rDNA arrays. Further multiple copies of the heterologous DNA are localized to a single region of rDNA, and all copies are linked to the rDNA when analyzed for segregation. The novel chromosome structures are not "pericentric" in nature.

The present invention relates to the integration of a suite of fatty acid modifying genes to a chromosomal location that results in high expression of elongase and sn-2 acylation activities which may result in seeds producing high C18, C20, and C22 mono- and unsaturated fatty acids. Thus modified fatty acids are produced in plant cells by the introduction of at least a first nucleic acid that is highly homologous to a native ribosomal DNA (rDNA) and a second nucleic acid that encodes a product associated with fatty acid metabolism.

The second nucleic acid or a plurality of second nucleic acids may comprise coding sequences encoding Nasturtium Fatty Acid Elongase (FAE), *Arabidopsis* FAE1, and yeast SLC 1. Alternatively, the second nucleic acid or a plurality of second nucleic acids may comprise coding sequences encoding a combination of fatty acid elongase and L-Phosphatidyl Acyl transferase enzymes.

Nucleic acids of the invention may encode activities that alter, or when expressed, lead to changes in fatty acid metabolism. Nucleic acids may also comprise activities that enhance the overall yield of a crop or further alter the characteristics of a crop organ or tissue. This may include enhanced growth for example in algae or enhanced accumulation of novel products. As used herein, "activities" may refer to both a protein encoded product as well as a product that would be essentially a RNA molecule that is not translated into a protein. In this regard, the nucleic acid may encode, for example, a RNA molecule that inhibits the expression of another gene.

In the context of the present invention, there is provided a first nucleic acid comprising a sequence that is homologous to native rDNA. Alternatively, the first nucleic acid consists or consists essentially of a sequence that is homologous to native rDNA. rDNA may be organized as arrays and are regions of high transcription that are amenable to the integration of one or more constructs encoding a product associated with fatty acid metabolism into the plant genome. Integration may occur at one or more sites. The present invention comprises the selection of transformed cells in which one or a plurality of the second nucleic acids has integrated at or near one or more rDNA arrays.

The nuclear genes encoding cytosolic ribosomal RNA such as 18S, 5.8S, 26S and 5S subunits are generally organized in arrays in higher eukaryotes, the repeated unit of which contains the transcription unit and a spacer sequence. The genes encoding 18S, 5.8S and 26S ribosomal subunits are transcribed as a single unit of 45S. The 5S rDNA gene is also arranged in clusters of tandemly repeated units. In higher eukaryotes, 5S and 18S-5.8S-26S rRNA genes are organized in separate clusters. rDNA arrays may be localized on either a single or several chromosomes and may be pericentric or non-pericentric. rDNA arrays are highly variable in size and location in plant genomes (Raina and Mukai. Genome, 42: 52-59, 1999). For example, soybean has only one 5S and one 45S rDNA locus whereas common bean has more than two 5S rDNA loci and two 45S rDNA loci (Shi et al. Theoretical and Applied Genetics, 93: 136-141, 1996). rDNA arrays are highly transcribed regions of the genome.

In the context of the present invention, the first nucleic acid comprises rDNA sequences that are homologous to native rDNA. As used herein, "homologous" refers to two sequences that show at least 50%, at least 55%, at least 60%, at least 65%, at least 70%, at least 75%, at least 80%, at least 83%, at least 85%, at least 87%, at least 89%, at least 91%, at least 93%, at least 95%, at least 97%, or at least 99% sequence identity over its entire length to a native ribosomal DNA (rDNA) of the plant cell to be transformed. Typically, homologous sequences have at least 50% sequence identity.

The first and second nucleic acid are typically introduced into cells at a ratio first to second nucleic acid of 300:1, 200:1, 100:1, 50:1, 30:1, 25:1, 20:1, 15:1, 10:1, 9:1, 8:1, 7:1, 6:1, 5:1, 4:1, 3:1, 2:1, or 1:1, and preferably at a ratio of 10:1.

As used herein, a "construct" refers to any recombinant polynucleotide molecule such as a plasmid, cosmid, virus, vector, autonomously replicating polynucleotide molecule, phage, or linear or circular single-stranded or double-stranded DNA or RNA polynucleotide molecule, derived from any source.

The first nucleic acid comprises, consists of, or consists essentially of a nucleotide sequence that has at least 50%, at least 55%, at least 60% at least 65%, at least 70%, at least 75%, at least 80%, at least 83%, at least 85%, at least 87%, at least 89%, at least 91%, at least 93%, at least 95%, at least 97%, at least 99% or has 100% sequence identity over its entire length to a native ribosomal DNA (rDNA) of the plant cell to be introduced.

Typically, the first nucleic acid comprises, consists of or consists essentially of a nucleotide sequence possessing at least 50% sequence identity over its entire length to a native rDNA sequence. As used herein, "consists essentially of" or "consisting essentially of" means that the nucleic acid sequence includes one or more nucleotide bases, including within the sequence or at one or both ends of the sequence, but that the additional nucleotide bases do not materially affect the function of the nucleic acid sequence.

The first nucleic acid comprises, consists of, or consists essentially of a nucleotide sequence that is 5S, 5.8S, 18S or 26S rDNA.

The first nucleic acid typically comprise a nucleotide sequence that is at least 100, at least 125, at least 150, at least 250, at least 500, at least 750, at least 1000, at least 1250, at least 1500, at least 1750, at least 2000, at least 2500, at least 3000, at least 5000, or at least 10000 nucleotides or base pairs in length; and preferably a nucleotide sequence that is 1.7-2.8 kb in length.

The second nucleic acid comprises a coding sequence encoding a product. In one embodiment, the product is associated with fatty acid metabolism.

The first and/or second nucleic acids integrate into or adjacent to rDNA. The nucleic acid may integrate into or adjacent to pericentric and/or non pericentric regions associated with native rDNA. In one embodiment, one or more copies of the second nucleic acid may integrate into one or more regions of pericentric and/or non pericentric rDNA. As used herein, the term "pericentric" means immediately adjacent to or close to the centromere of a chromosome. The term "telocentric" means immediately adjacent to or close to the telomere of a chromosome. The nucleic acid may integrate into rDNA at a position that is closer to the telomere than to the centromere, or that is closer to the centromere than to the telomere, or both.

In one embodiment, the first and second nucleic acids are on the same construct. In another embodiment, the first and second nucleic acids are on separate constructs.

One or more copies of the first and/or second nucleic acid may integrate into or adjacent to native rDNA. First and/or second nucleic acids may be amplified at the site of the insertion to produce multiple copies in low or relatively low copy number (e.g. 2 to 10 copies). Two or more of the inserted and/or amplified first and/or second nucleic acids may be in sufficiently close proximity that they segregate as a single genetic locus.

The integration of the heterologous DNA into or adjacent the rDNA array may result in a continuum of event structures including, but not limited to, a single insert without any duplication, an insert that is duplicated within a very localized duplication region, and an insert that undergoes large scale amplification that provides gross chromosomal changes such as "sausage chromosomes" with many millions of base pairs of DNA comprising amplified and duplicated sequences. In one embodiment, the integrated heterologous DNA is an insert that is duplicated or at low copy number, and without gross cytomorphological chromosomal events.

The present invention relates to methods of producing a transgenic plant comprising a first and a second nucleic acid.

In the context of the present invention, "plant" refers to a eukaryotic species that contains, in addition to a nucleus and mitochondria, chloroplasts capable of carrying out photosynthesis. A plant may be unicellular, multi-cellular or comprised of numerous tissues or organs. Plants may reproduce sexually or asexually and may be perennial or annual in growth habit. Plants may be terrestrial or aquatic. Plants may comprise algae. As used herein, a plant encompasses a plant cell, plant organ or plant tissue, or other parts of a whole plant such as shoot vegetative organs/structures (e.g. leaves, stems and tubers), roots, flowers and floral organs/structures (e.g. bracts, sepals, petals, stamens, carpels, anthers and ovules), seeds (including embryo, endosperm, and seed coat) and fruits (the mature ovary), plant tissues (e.g. vascular tissue, ground tissue, and the like) and cells (e.g. guard cells, egg cells, trichomes and the like), and progeny of the same.

As used herein, "transgenic plant" refers to a plant, plant cell culture, plant cell line, plant tissue culture, or progeny of a transformed plant cell or protoplast wherein foreign genetic material has been introduced into the genome of the plant cell. The terms "transgenic plant" and "transformed plant" are used synonymously to refer to a plant whose genome contains exogenous genetic material.

As used herein, "plant cell culture" refers to plant cells maintained in media and separated from their original tissue source. Plant cell cultures are typically grown as cell suspension cultures in liquid medium or as callus cultures on solid medium.

As used herein, "nucleotide sequence" or "nucleic acid" refers to a polymer of DNA or RNA which can be single or double stranded and optionally containing synthetic, non-natural or altered nucleotide bases capable of incorporation into DNA or RNA polymers. "Nucleic acids" or "Nucleic acid sequences" may encompass genes, cDNA, DNA and RNA encoded by a gene. Nucleic acids or nucleic acid sequences may comprise at least 3, at least 10, at least 100, at least 1000, at least 5000, or at least 10000 nucleotides or base pairs.

Nucleic acids may be modified by any chemical and/or biological means known in the art including, but not limited to, reaction with any known chemicals such as alkylating agents, browning sugars, etc; conjugation to a linking group (e.g. PEG); methylation; oxidation; ionizing radiation; or the action of chemical carcinogens. Such nucleic acid modifications may occur during synthesis or processing or following treatment with chemical reagents known in the art. As used herein, "% sequence identity" is determined by comparing two optimally aligned sequences over a comparison window, where the fragment of the polynucleotide sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid residue occurs in both sequences to yield the number of matched positions, dividing the number of matched positions by the total number of positions in the comparison window and multiplying the result by 100 to provide the percentage of sequence identity. Algorithms to align sequences are known in the art. Exemplary algorithms include, but are not limited to, the local homology algorithm of Smith and Waterman (Add APL Math, 2: 482, 1981); the homology alignment algorithm of Needleman and Wunsch (J Mol Biol, 48: 443, 1970); the search for similarity method of Pearson and Lipman (Proc Natl Acad Sci USA, 85: 2444, 1988); and computerized implementations of these algorithms (GAP, BESTFIT, BLAST, PASTA, and TFASTA in the Wisconsin Genetics Software Package, Genetics Computer Group (GCG), 575 Science Dr., Madison, Wis.). In one aspect, two sequences may be aligned using the "Blast 2 Sequences" tool at the NCBI website at default settings (Tatusova and Madden. FEMS Microbiol Lett, 174: 247-250, 1999). Alternatively, nucleic acids sequences may be aligned by human inspection.

As used herein, "native ribosomal DNA" refers to the ribosomal DNA that naturally occurs in the cell that is to be transformed.

As used herein, "rDNA" means ribosomal DNA and refers to genes encoding ribosomal RNA including, but not limited to, genes encoding the 5S, 5.8S, 18S and 25S/26S ribosomal RNA.

The second nucleic acid typically comprises one or more coding sequences that are operably linked to one or more regulatory elements.

As used herein, "coding sequence" refers to a DNA or RNA sequence that codes for a specific amino acid sequence and may exclude the non-coding sequences such as introns and untranslated regions of a gene. A coding sequence may be any length. The coding sequence may comprise at least 3, at least 10, at least 100, at least 1000, at least 5000, or at least 10000 nucleotides or base pairs.

As used herein, "operably-linked" refers to two nucleic acid sequences that are related physically or functionally. For example, a regulatory element is said to be "operably linked to" to a coding sequence if the two sequences are situated such that the regulatory DNA sequence affects expression of the coding DNA sequence. Coding sequences may be operably-linked to regulatory sequences in sense or antisense orientation.

As used herein, "regulatory element" refers nucleic acid sequences that affect the expression of a coding sequence. Regulatory elements are known in the art and include, but are not limited to, promoters, enhancers, transcription terminators, polyadenylation sites, matrix attachment regions and/or other elements that regulate expression of a coding sequence.

As used herein, a "promoter" refers to a nucleotide sequence that directs the initiation and rate of transcription of a coding sequence (reviewed in Roeder, Trends Biochem Sci, 16: 402, 1991). The promoter contains the site at which RNA polymerase binds and also contains sites for the binding of other regulatory elements (such as transcription factors). Promoters may be naturally occurring or synthetic. Further, promoters may be species specific (for example, active only in *B. napus*); tissue specific (for example, the *Brassica* napin or cruciferin seed specific promoters, the soybean glycinin or conglycinin promoters); developmentally specific (for example, active only during embryogenesis); constitutive (for example, Nopaline synthase, Beta actin, ubiquitin, CsVMV and CaMV 35S promoters); or inducible (for example the stilbene synthase promoter). A promoter includes a minimal promoter that is a short DNA sequence comprised of a TATA box or an Inr element, and other sequences that serve to specify the site of transcription initiation, to which regulatory elements are added for control of expression. A promoter may also refer to a nucleotide sequence that includes a minimal promoter plus DNA elements that regulates the expression of a coding sequence, such as enhancers and silencers. For example, algal cells may be modified by transformation with a nucleic acid construct under the control of a heterologous promoter.

As used herein, "expression" or "expressing" refers to production of any detectable level of a product encoded by the coding sequence Enhancers and silencers are DNA elements that affect transcription of a linked promoter positively or negatively, respectively (reviewed in Blackwood and Kadonaga, Science, 281: 61, 1998). Generally, these DNA elements function independent of distance and orientation relative to the promoter.

Polyadenylation site refers to a DNA sequence that signals the RNA transcription machinery to add a series of the nucleotide A at about 30 bp downstream from the polyadenylation site.

Transcription terminators are DNA sequences that signal the termination of transcription. Transcription terminators are known in the art. The transcription terminator may be derived from the nopaline synthase gene (nos) of *Agrobacterium tumefaciens* or the CaMV terminator sequence and others known in the art.

The second nucleic acid may encode a product associated with plant fatty acid metabolism.

As used herein, a "product associated with plant fatty acid metabolism" refers to an enzyme involved in fatty acid biosynthesis or metabolism, including but not limited to modifying and catabolic activities. The product associated with plant fatty acid metabolism may include proteins, peptides, or fragments thereof. Modifications of the encoded product may include in vivo and in vitro chemical derivatization of polypeptides, e.g., acetylation, carboxylation, phosphorylation, or glycosylation; such modifications may occur during polypeptide synthesis or processing or following treatment with isolated modifying enzymes.

As used herein, the terms "peptide", "oligopeptide", "polypeptide" and "protein" may be used interchangeably. Peptides may contain non-natural amino acids and may be joined to linker elements known to the skilled person. Peptides may also be monomeric or multimeric. Peptide fragments comprise a contiguous span of at least 5, at least 10, at least 25, at least 50, at least 100, at least 250, at least 500, at least 1000, at least 1500, or at least 2500 consecutive amino acids and may retain the desired activity of the full length peptide.

Very Long Chain Fatty Acids (VLCFAs) are synthesized outside the plastid by a membrane bound fatty acid elongation complex (elongase) using acyl-CoA substrates. VLCFAs are incorporated into a variety of plant lipids including, but not limited to, seed oil, wax, cutin and membrane sphingolipids. Seed oil VLCFAs include erucic acid (C22: 1), used in the production of lubricants, nylons, cosmetics, pharmaceuticals and plasticizers. VLCFA have been recognized as structural components in a variety of fat molecules such as sphingolipids, glycerophospholipids, triacylglycerols, sterol- and wax-esters. Other lipids, such as fatty acids of the composition C18:2, C16:0, C18:3(alpha), C18:1, C16:3, C16:1, and C16:4 can be found in many algal species, along with many long chain fatty acids or unusual fatty acids.

Seed lipids of higher plants are mainly composed of C16 and C18 fatty acids. Species of *Brassica* including mustard (*Brassica juncea, B. carinata* and *B. nigra*) and industrial rape (*B. napus*) contain a component of Very Long Chain Fatty Acids (VLCFA) which have more than 18 carbons such as C20:1 (eicosenoic acid) or C22:1 (erucic acid). Erucic acid content in rapeseed oil is limited to 66% partly because the sn-2 acyl transferase cannot incorporate erucic acid at the sn-2 position in triglycerides (Bemerth and Frentzen. Plant Sci, 67: 21-27, 1990; Cao et al. Plant Physiol, 94: 1199-1206, 1990).

VLCFAs are synthesized by a fatty acid elongation (FAE) complex, involving four enzymatic reactions. The first reaction of elongation involves condensation of malonyl-CoA with a long chain substrate producing a 3-ketoacyl-CoA (via 3-ketoacyl-CoA synthase (KCS)). Subsequent reactions are reduction of 3-hydroxyacyl-CoA (via 3-ketoacyl-CoA reductase), dehydration to an enoyl-CoA (via a dehydrase), followed by a second reduction to form the elongated acyl-CoA (via enoyl-CoA reductase). The 3-ketoacyl-CoA synthase (KCS) catalyzing the condensation reaction plays a key role in determining the chain length of fatty acid products found in seed oils and is the rate-limiting enzyme for seed VLCFA production. Hereafter the terms elongase and FAE will signify 3-ketoacyl-CoA synthase condensing enzyme genes/proteins. The composition of the fatty acyl-CoA pool available for elongation and the presence and size of the neutral lipid sink are additional important factors influencing the types and levels of VLCFAs made in particular cells.

In one embodiment, the gene product associated with plant fatty acid metabolism may be a FAE-1 enzyme or a fragment thereof; where FAE1 is selected from *Arabidopsis thaliana, Brassica napus* or Nasturtium (*Tropaeolum*). The genes encoding FAE1 and its homologs have been cloned from *Arabidopsis thaliana* and from *Brassica napus* (two homologous sequences, Bn-FAE 1.1 and Bn-FAE 1.2). US Pub No: 20070204370 described genes encoding *Tropaeolum majus* FAE. The *T. majus* FAE is capable of producing 70-75% erucic acid and accumulates trierucin as the predominant triacylglycerol (TAG) in its seed oil (see Mietkiewska et al. Plant Physiol, 136: 2665, 2004).

In another embodiment, the gene product associated with plant fatty acid metabolism may be a SLC1 enzyme or a fragment thereof; where SLC1 is from *Saccharomyces cerevisiae*. SLC1 (sphingolipid compensation) gene was originally cloned from a yeast mutant without the ability to produce sphingolipids (Lester et al. J Biol Chem, 268: 845-856, 1993). Zou et al. (The Plant Cell, 9: 909-923, 1997) demonstrated that the SLC1-1 gene product is an sn-2 acyltransferase; that it enhanced seed lysophosphatidic acid acyltransferase (LPAT) activity; and that it altered the oil content and oil composition of plant seed lipids.

In a further embodiment, the second nucleic acid may comprise the coding sequences for atFAE1 (FAE1 of *Arabidopsis thaliana*), nFAE1 (FAE1 of Nasturtium) and ySLC1 (SLC1 of the yeast *Saccharomyces cerevisiae*).

Alternatively, the second nucleic acid may comprise a portion of the coding sequences for atFAE1, nFAE1 and/or ySLC1, where the portion of the coding sequence encodes a protein or a peptide that is capable of modifying fatty acid metabolism.

The second nucleic acid may comprise a sequence encoding any fatty acid modifying enzyme, structural gene or other genes that control fatty acid deposition. Other suitable enzymes associated with fatty acid metabolism that may be used in the context of the invention include, but are not limited to, FAE elongases with unique activities such as that of lunaria, *cardamine* or *teesdalia* with a preference for elongating C22.1 to C24.1 (see 08061334), genes such as DGAT1 from *Trapaeolum majus* which can increase the overall levels of seed oils in *brassica rapa* and canola (Xu et al, *Plant Biotechnology Journal* (2008) 6, pp. 1467-1488).

The present invention is not limited to any particular method for transforming plant cells. Methods for introducing nucleic acids into cells (also referred to herein as "transformation") are known in the art and include, but are not limited to: Viral methods (Clapp. Clin Perinatol, 20: 155-168, 1993; Lu et al. J Exp Med, 178: 2089-2096, 1993; Eglitis and Anderson. Biotechniques, 6: 608-614, 1988; Eglitis et al. Avd Exp Med Biol, 241: 19-27, 1988); physical methods such as microinjection (Capecchi. Cell, 22: 479-488, 1980), electroporation (Wong and Neumann. Biochim Biophys Res Commun, 107: 584-587, 1982; Fromm et al, Proc Natl Acad Sci USA, 82: 5824-5828, 1985; U.S. Pat. No. 5,384,253) and the gene gun (Johnston and Tang. Methods Cell Biol, 43: 353-365, 1994; Fynan et al. Proc Natl Acad Sci USA, 90: 11478-11482, 1993); chemical methods (Graham and van der Eb. Virology, 54: 536-539, 1973; Zatloukal et al. Ann NY Acad Sci, 660: 136-153, 1992); and receptor mediated methods (Curiel et al. Proc Natl Acad Sci USA, 88: 8850-8854, 1991; Curiel et al. Hum Gen Ther, 3: 147-154, 1992; Wagner et al. Proc Natl Acad Sci USA, 89: 6099-6103, 1992).

The introduction of DNA into plant cells by *Agrobacterium* mediated transfer is well known to those skilled in the art. Virulent strains of *Agrobacterium* contain a large plasmid DNA known as a Ti-plasmid that contains genes required for DNA transfer (vir genes), replication and a T-DNA region that is transferred to plant cells. The T-DNA region is bordered by T-DNA border sequences that are essential to the DNA transfer process. These T-DNA border sequences are recognized by the vir genes. The two primary types of *Agrobacterium*-based plant transformation systems include binary [see for example U.S. Pat. No. 4,940,838] and co-integrate [see for example Fraley et al. Biotechnology, 3: 629-635, 1985] methods. In both systems, the T-DNA border repeats are maintained and the natural DNA transfer process is used to transfer the DNA fragment located between the T-DNA borders into the plant cell genome.

Another method for introducing DNA into plant cells is by biolistics. This method involves the bombardment of plant cells with microscopic particles (such as gold or tungsten particles) coated with DNA. The particles are rapidly accelerated, typically by gas or electrical discharge, through the cell wall and membranes, whereby the DNA is released into the cell and incorporated into the genome of the cell. This method is used for transformation of many crops, including corn, wheat, barley, rice, woody tree species and others. Biolistic bombardment has been proven effective in transfecting a wide variety of animal tissues as well as in both eukaryotic and prokaryotic microbes, mitochondria, and microbial and plant chloroplasts (Johnston. Nature, 346: 776-777, 1990; Klein et al. Bio/Technol, 10: 286-291, 1992; Pecorino and Lo. Curr Biol, 2:30-32, 1992; Jiao et al, Bio/Technol, 11: 497-502, 1993).

Another method for introducing DNA into plant cells is by electroporation. This method involves a pulse of high voltage applied to protoplasts/cells/tissues resulting in transient pores in the plasma membrane which facilitates the uptake of foreign DNA. The foreign DNA enter through the holes into the cytoplasm and then to the nucleus.

Plant cells may be transformed by liposome mediated gene transfer. This method refers to the use of liposomes, which are circular lipid molecules with an aqueous interior, to deliver nucleic acids into cells. Liposomes encapsulate DNA fragments and then adhere to and fuse with the cell membranes resulting in the transfer of DNA. The DNA enters the cell and then to the nucleus.

Nucleic acid constructs of the present invention may be introduced into plant protoplasts. Plant protoplasts are cells in which its cell wall is completely or partially removed using either mechanical or enzymatic means, and may be transformed with known methods including, calcium phosphate based precipitation, polyethylene glycol treatment and electroporation (see for example Potrykus et al., Mol. Gen. Genet., 199: 183, 1985; Marcotte et al., Nature, 335: 454, 1988). Polyethylene glycol (PEG) is a polymer of ethylene oxide. It is widely used as a polymeric gene carrier to induce DNA uptake into plant protoplasts. PEG may be used in combination with divalent cations to precipitate DNA and effect cellular uptake. Alternatively, PEG may be complexed with other polymers, such as poly(ethylene imine) and poly L lysine.

The introduction of nucleic acids into a sample of plant cells results in a transformation event. A "transformation event" or "event" refers to one instance of plant cell transformation. These terms may also refer to the outcome of one sample of plant cells transformed with one of the transformation methods described herein.

Successful genetic transformation of more than 20 algal species has been demonstrated, comprising at least ten species of green algae, six species of red algae, four diatom species and two dinoflagellates. Common plant selectable markers and promoters function well in algal cells as do various other genes (e.g., see: Armin Hallmann, Algal Transgenics and Biotechnology, Transgenic Plant Journal, 2007 Global Science Books)

In the context of the present invention, the nucleic acids are heterologous DNA that is introduced into the cell. As used herein, "heterologous", "foreign" and "exogenous" DNA and RNA are used interchangeably and refer to DNA or RNA that does not occur naturally as part of the plant genome in which it is present or which is found in a location or locations in the genome that differ from that in which it occurs in nature. Thus, heterologous or foreign DNA or RNA is nucleic acid that is not normally found in the host genome in an identical context. It is DNA or RNA that is not endogenous to the cell and has been exogenously introduced into the cell. In one aspect, heterologous DNA may be the same as the host DNA but modified by methods known in the art, where the modifications include, but are not limited to, insertion in a vector, linked to a foreign promoter and/or other regulatory elements, or repeated at multiple copies. In another aspect, heterologous DNA may be from a different organism, a different species, a different genus or a different kingdom, as the host DNA. Further, the heterologous DNA may be a transgene. As used herein, "transgene" refers to a segment of DNA containing a gene sequence that has been isolated from one organism and introduced into a different organism.

The use of plant cells for producing transgenic plants is known in the art.

Plant species from which cells may be obtained include, but are not limited to, field and row crops, biomass crops, and oilseed crops and algae. Field crop plants include maize, hops, jojoba, Jatropha, Camelina, peanuts, rice, safflower, grains (barley, oats, rye, wheat, sorghum, and others) and fibre plants (cotton, flax, hemp, jute). Row crops include primarily leguminous plants (beans, lentils, peas, soybeans) and others. Biomass crops may include sugarcane, switchgrass, *Miscanthus*, tobacco, maize and others. Algae includes members of the Chlorophyceae.

Examples of crops appropriate for development as biofuel replacement feedstocks include *brassica* (rape) and other mustards, soybean, palm, Jatropha, Camelina, flax, sunflower, jojoba, *crambe*, castor, cassava, peanut, olives, coconut, and others. In the context of the present invention, algal species represent a preferred plant species of particular interest. In particular Chlorophyceae are preferred group of green algae.

A preferred crop is a member of the Euphorbacea, Fabaceae, Brassicaceae, Poaceae, Limnanthaceae, Tropaeolaceae or *Simmondsia*. Plants of the genera Glycine, *Zea, Brassica* and *Linum* are especially preferred.

Plant cell culture techniques are known in the art (see for example Fischer et al. Biotechnol Appl Biochem, 30: 109-112, 1999; Doran. Current Opinions in Biotechnology, 11: 199-204, 2000). The skilled person would appreciate that the composition of the culture media, its pH and the incubating conditions, such as temperatures, aeration, $CO_2$ levels, and light cycles, may vary depending on the type of cells.

After transformation, plant cells may be sub-cloned to obtain clonal populations of cells. Methods of sub-cloning cells are known in the art and include, but are not limited to, limiting dilution of the pool of transformed cells. The transformed cells may also be grown under selective pressure to identify those that contain and/or express the gene product associated with plant fatty acid metabolism. In this regard, the nucleic acid construct encodes a selectable marker. Selectable markers may be used to select for plants or plant cells that contain the exogenous genetic material. The exogenous genetic material may include, but is not limited to, an enzyme that confers resistance to an agent such as a herbicide or an antibiotic, or a protein that reports the presence of the construct.

Examples of a selectable marker include, but are not limited to, a neo gene, which codes for kanamycin resistance and can be selected for using kanamycin, RptII, G418, hpt etc.; an amp resistance gene for selection with the antibiotic ampicillin; an hygromycinR gene for hygromycin resistance; a BAR gene (encoding phosphinothricin acetyl transferase) which codes for bialaphos resistance; a mutant EPSP synthase gene, aadA, which encodes glyphosate resistance; a nitrilase gene, which confers resistance to bromoxynil; a mutant acetolactate synthase gene (ALS), which confers imidazolinone or sulphonylurea resistance, ALS, and a methotrexate resistant DHFR gene. Other non-selectable but screenable markers include: a β-glucuronidase or uidA gene (GUS), which encodes an enzyme for which various chromogenic substrates are known, green fluorescent protein (GFP), and luciferase (LUX).

A nucleic acid construct of the present invention may encode a gene conferring resistance to bialaphos (also known as bilanafos or PPT; commercialized under the trade-marks Basta@, Buster® and Liberty@) which is converted to the phytotoxic agent phosphinothricin in plant cells. In one aspect, the bialaphos resistance gene is a BAR gene. In another aspect, multiple copies of the glutamine synthetase gene confer resistance to bialaphos.

After preparing clonal populations of transgenic plant cells, the cells may be characterized and selected based on analysis at the level of DNA, RNA and protein. Preferably, transgenic plant cells in which the nucleic acid construct is stably integrated into rDNA are selected. As used herein, "stably integrated" refers to the integration of genetic material into the genome of the transgenic plant cell and remains part of the plant cell genome over time and passage number. Thus a cell comprising a stably integrated nucleic acid construct of the present invention would continue to produce the gene product associated with plant fatty acid metabolism.

Stable integration of nucleic acid constructs may be influenced by a number of factors including, but not limited to, the transformation method used and the vector containing the gene of interest. The transformation method determines which cell type can be targeted for stable integration. The type of vector used for stable integration defines the integration mechanism, the regulation of transgene expression and the selection conditions for stably expressing cells. After integration, the level and time of expression of the gene of interest may depend on the linked promoter and on the particular integration site.

The site of integration may affect the transcription rate of the gene of interest. Usually an expression plasmid is integrated into the genome of the target cell randomly. Integration into inactive heterochromatin results in little or no transgene expression, whereas integration into active euchromatin often allows transgene expression.

In the context of the present invention, the first and/or second nucleic acids target rDNA arrays of the plant cell to be transformed. Thus the first nucleic acid comprising rDNA sequences homologous to native rDNA may be integrated at or adjacent to the native rDNA array. Further, the second nucleic acid comprising a coding sequence operably linked to one or more regulatory sequences may be integrated at or adjacent to the native rDNA array.

It is also contemplated, within the scope of the present invention, that introduction of a first and second nucleic acid, wherein said first nucleic acid comprises an rDNA sequence and the second nucleic acid comprises a coding sequence operably linked to a regulatory region, may lead to the formation of a novel chromosomal region that comprises an integration of both the first and second nucleic acids to provide a chromosomal structure that shares similarity with native rDNA regions by virtue of the incorporation of the first rDNA sequence and subsequent formation of a new genetic locus that comprises both the introduced first nucleic acid rDNA and adjacent to this first nucleic acid the second nucleic acid.

Following transformation, cells in which the nucleic acid construct is integrated into rDNA are selected. As noted herein, rDNA arrays typically comprise regions of active transcription thus the selected gene encoding the product associated with plant fatty acid metabolism is expressed.

The integrated first and/or second nucleic acids may be present in the transgenic plant cell in 2 copies, 3 copies, 4 copies, 5 copies, 6 copies, 7 copies, 8 copies, 9 copies, 10 copies, 11 copies, 12 copies, 13 copies, 14 copies, 15 copies, 16 copies, 17 copies, 18 copies, 19 copies, 20 copies, 21 copies, 22 copies, 23 copies, 24 copies, 25 copies, 26 copies, 27 copies, 28 copies, 29 copies, 30 copies, 31 copies, 32 copies, 33 copies, 34 copies, 35 copies, 36 copies, 37 copies, 38 copies, 39 copies, 40 copies, 41 copies, 42 copies, 43 copies, 44 copies, 45 copies, 46 copies, 47 copies, 48 copies, 49 copies, 50 copies, 51 copies, 52 copies, 53 copies, 54 copies, 55 copies, 56 copies, 57 copies, 58 copies, 59 copies, 60 copies or more.

Targeted introduction of DNA into the genome may be accomplished by a number of methods including, but not limited to, targeted recombination, homologous recombination and site-specific recombination. Homologous recombination and gene targeting in plants (reviewed in Reiss. International Review of Cytology, 228: 85-139, 2003) and mammalian cells (reviewed in Sorrell and Kolb. Biotechnology Advances, 23: 431-469, 2005) are known in the art.

As used herein, "targeted recombination" refers to integration of a heterologous nucleic acid construct into a rDNA array, where the integration is facilitated by heterologous rDNA that is homologous to the native rDNA of the cell to be transformed.

Homologous recombination relies on sequence identity between a piece of DNA that is introduced into a cell and the cell's genome. Homologous recombination is an extremely rare event. However, the frequency of homologous recombination may be increased with strategies involving the introduction of DNA double-strand breaks, triplex forming oligonucleotides or adeno-associated virus.

As used herein, "site-specific recombination" refers to the enzymatic recombination that occurs when at least two discrete DNA sequences interact to combine into a single nucleic acid sequence in the presence of the enzyme. Site-specific recombination relies on enzymes such as recombinases, transposases and integrases, which catalyse DNA strand exchange between DNA molecules that have only limited sequence homology. Mechanisms of site specific recombination are known in the art (reviewed in Grindley et al. Annu Rev Biochem, 75: 567-605, 2006). The recognition sites of site-specific recombinases (for example Cre and att sites) are usually 30-50 bp. The pairs of sites between which the recombination occurs are usually identical, but there are exceptions e.g. attP and attB of λ integrase (Landy. Ann Rev Biochem, 58: 913-949, 1989).

The nucleic acid construct of the present invention may comprise a site-specific recombination sequence. Site-specific recombination sequences may be useful for the directed integration of subsequently introduced genetic material into the transformed cell.

Preferably, the site-specific recombination sequence is an att sequence, for example from λ phage. λ phage is a virus that infects bacteria. The integration of λ phage takes place at an attachment site in the bacterial genome, called att$^λ$. The sequence of the att site in the bacterial genome is called attB and consists of the parts B—O—B', whereas the complementary sequence in the circular phage genome is called attP and consists of the parts P—O—P'. Integration proceeds via a Holliday structure and requires both the phage protein int and the bacterial protein IHF (integration host factor). Both int and IHF bind to attP and form an intrasome (a DNA-protein-complex) for site-specific recombination of the phage and host DNA. The integrated host and phage sequences become B—O—P'-phage DNA-P—O—B'. Accordingly, att sites may be used for targeted integration of heterologous DNA. Other site specific recombination systems sequences that may be employed in the context of the invention include, but are not limited to, cre-lox and flp-frt.

Methods for localizing the integrated nucleic acid construct within the transformed plant cell genome are known in the art and include, but are not limited to, fluorescence in situ hybridization (FISH) and PCR amplification followed by Southern blot analysis. In addition, the gene transcripts may be examined, for example, by Northern blot analysis or RT-PCR, while the gene product associated with plant fatty acid metabolism may be assessed, for example, by Western blot, LC-MSMS, ELISA and gas liquid chromatography.

Fluorescence in situ hybridization (FISH) is a molecular cytogenetic technique in which fluorescently labeled DNA probes are hybridized to metaphase spread or interphase nuclei. The sample DNA (metaphase chromosomes or interphase nuclei) is first denatured to separate the complementary strands within the DNA double helix structure. The fluorescently labeled probe of interest is then added to the denatured sample mixture and hybridized with the sample DNA at the target site as it re-anneals back into a double helix. The probe signal is assessed with a fluorescent microscope. A plurality of probes may be used to simultaneously co-localize distinct targets. In the context of the present invention, FISH may be used to co-localize the integrated nucleic acid constructs and the native rDNA array, thus identify transgenic plant cell lines that have a plurality of second nucleic acids integrated at or adjacent to the native rDNA.

Another method of identifying site of integration of the nucleic acid constructs of the present invention is by PCR followed by Southern blot analysis. The skilled person would appreciate that there are a number of PCR approaches to identifying the integrated nucleic acid construct. In one approach, one of the two primers corresponds to a sequence within the nucleic acid construct, and the other corresponds to a sequence adjacent to the nucleic acid (for example, a primer having 26s rDNA sequences). In another approach, one primer corresponds to a genomic DNA sequence that is upstream of a putative nucleic acid integration site and the other primer corresponds to a genomic DNA sequence that is downstream of the putative nucleic acid integration site. Subsequently, the PCR product is probed with a nucleic acid probe by Southern blot analysis. Polymerase chain reaction (PCR) (U.S. Pat. Nos. 4,683,195; 4,683,202; and 4,965,188) is used to increase the concentration of a target nucleic acid sequence in a sample without cloning, and requires the availability of target sequence information to design suitable forward and reverse oligonucleotide primers which are typically 10 to 30 base pairs in length. Southern blotting combines agarose gel electrophoresis for size separation of the amplified DNA with methods to transfer the size-separated DNA to a filter membrane for nucleic acid probe hybridization. The probe may be conjugated to a label, such as a radiolabel or a fluorescent label, so that the DNA/probe hybrid may be visualized, for example, on film or by a phosphoimager. Southern blots are a standard tool of molecular biologists (J. Sambrook et al. (1989) Molecular Cloning: A Laboratory Manual (Cold Spring Harbor Press, NY), pp 9.31-9.58). Southern blot analysis may also be used to determine the copy number of the nucleic acid construct that has integrated into the plant cell genome by comparing the quantity of the integrated nucleic acid construct with known quantities of DNA probed on the same blot. Methods of quantitating the detected DNA are known in the art, and include for example, densitometry.

As used herein, a "nucleic acid probe" is a DNA or RNA fragment that includes a sufficient number of nucleotides to specifically hybridize to a DNA or RNA target that includes identical or closely related sequences of nucleotides. A probe may contain any number of nucleotides, from as few as about 10 and as many as hundreds of thousands of nucleotides. The conditions and protocols for such hybridization reactions are well known to those of skill in the art, as are the effects of probe size, temperature, degree of mismatch, salt concentration and other parameters on the hybridization reaction. For example, the lower the temperature and higher the salt concentration at which the hybridization reaction is carried out, the greater the degree of mismatch that may be present in the hybrid molecules.

To be used as a hybridization probe, the nucleic acid is generally rendered detectable by labeling it with a detectable moiety or label, such as $^{32}P$, $^{3}H$ and $^{14}C$, or by other means, including chemical labelling, such as by nick-translation of DNA in the presence of deoxyuridylate biotinylated at the 5'-position of the uracil moiety. The resulting probe includes the biotinylated uridylate in place of thymidylate residues and can be detected [via the biotin moieties] by any of a number of commercially available detection systems based on binding of streptavidin to the biotin. Such commercially available detection systems can be obtained, for example, from Enzo Biochemicals, Inc. [New York, N.Y.]. Any other label known to those of skill in the art, including non-radioactive labels, may be used as long as it renders the probes sufficiently detectable, which is a function of the sensitivity of the assay, the time available [for culturing cells, extracting DNA, and hybridization assays], the quantity of DNA or RNA available as a source of the probe, the particular label and the means used to detect the label.

As used herein, stringency conditions under which DNA molecules form stable hybrids may include:
1) high stringency: 0.1×SSPE, 0.1% SDS, 65° C.
2) medium stringency: 0.2×SSPE, 0.1% SDS, 50° C.
3) low stringency: 1.0×SSPE, 0.1% SDS, 50° C.
or any combination of salt and temperature and other reagents that result in selection of the same degree of mismatch or matching. See, for example Britten et al. *Methods Enzymol.* 29E: 363-406, 1974.

Following selection of plant cells based on localization of the gene insert at or adjacent to rDNA and expression of a gene product associated with fatty acid metabolism, the product may be recovered from the plants. Further, the product associated with fatty acid metabolism may be purified once recovered.

The gene product associated with fatty acid metabolism may be recovered from cultured plant cells by disrupting cells according to methods known in the art including, but not limited to, mechanical, chemical and enzymatic approaches.

The use of enzymatic methods to remove cell walls is well-established for preparing cells for disruption or for preparation of protoplasts (cells without cell walls) for other uses such as introducing cloned DNA or subcellular organelle isolation. The enzymes are generally commercially available and, in most cases, were originally isolated from biological sources (e.g. lysozyme from hen egg white). Exemplary enzymes include lysozyme, lysostaphin, zymolase, cellulase, muthanolysin, glycanases, proteases, and mannase.

Another method of cell disruption is detergent-based cell lysis. This method may be used in conjunction with homogenization or mechanical grinding. Detergents disrupt the lipid barrier surrounding cells by disrupting lipid:lipid, lipid:protein and protein:protein interactions. The appropriate detergent for cell lysis depends on cell type and source and on the downstream applications following cell lysis. Suitable detergents would be known to the skilled person. Animal, bacterial and plant cells all have differing requirements for optimal lysis due to the presence or absence, or chemical makeup of a cell wall.

In comparison with ionic detergents, nonionic and zwitterionic detergents are milder, resulting in less protein denaturation upon cell lysis and are often used to disrupt cells when it is critical to maintain protein function or interactions. CHAPS, a zwitterionic detergent, and the Triton™ X series of nonionic detergents are commonly used for cell disruption. Ionic detergents are strong solubilizing agents and tend to denature proteins. SDS is an ionic detergent that is used extensively in studies assessing protein levels by gel electrophoresis and western blotting.

Another method for cell disruption uses small glass, ceramic or steel beads and a high level of agitation by stirring or shaking of the mix. This method is often referred to as beadbeating. In one aspect, beads are added to the cell or tissue suspension in a test-tube and the sample is mixed on vortex mixer. In another aspect, beadbeating is done in closed vials. The sample and the beads are vigorously agitated at about 2000 oscillations per minute in a specially designed shaker driven by an electric motor.

Another method for cell disruption is known as sonication and refers to the application of ultrasound (typically 20-50 kHz) to the sample. In this method, a high-frequency is generated electronically and the mechanical energy is transmitted to the sample via a metal probe that oscillates with high frequency. The probe is placed into the cell-containing sample and the high-frequency oscillation causes a localized low pressure region resulting in cavitation and impaction, ultimately breaking open the cells.

A further method of cell disruption relies on high-shear force. High shear mechanical methods for cell disruption fall into three major classes: rotor-stator disruptors, valve-type processors, and fixed-geometry processors. These processors all work by placing the bulk aqueous media under shear forces that pull the cells apart. These systems are especially useful for larger scale laboratory experiments (over 20 ml) and offer the option for large-scale production.

The gene product associated with plant fatty acid metabolism may further comprise a protein tag. Protein tags find many uses in a number of applications for example, protein purification, specific enzymatic modification and chemical modification tag. Protein tags are known in the art and include, but are not limited to, affinity tags, solubilization tags, chromatography tags, epitope tags and fluorescent tags. In some instances, these tags are removable by chemical agents or by enzymatic means.

Affinity tags are attached to proteins so that they can be purified using an affinity technique. Exemplary affinity tags include chitin binding protein (CBP), maltose binding protein (MBP), and glutathione-s-transferase (GST). The poly (His) tag binds to metal matrices and is widely-used in protein purification.

Solubilization tags are used to assist in the proper folding in proteins and to prevent protein precipitation. Exemplary solubilization tags include thioredoxin (TRX) and poly (NANP). Some affinity tags may also serve as a solubilization agent, including MBP and GST.

Chromatography tags are used to alter chromatographic properties of the protein to provide different resolution across a particular separation technique. Exemplary chromatography tags include FLAG, consisting of polyanionic amino acids.

Epitope tags are short peptide sequences chosen because of their immunoreactivity with high-affinity antibodies. Exemplary epitope tags include V5-tag, c-myc-tag, and HA-tag. These tags are useful for western blotting, immunoprecipitation and for antibody purification.

Fluorescence tags are used to visualize a protein. GFP and its variants are the most commonly used fluorescence tags.

The recovered gene product associated with plant fatty acid metabolism may be purified. Methods of protein purification are known in the art and include, but are not limited to, centrifugation to separate mixtures of particles of varying masses or densities suspended in a liquid; SDS PAGE to separate proteins according to their size or molecular weight; or by various chromatography approaches including, but not limited to, size exclusion chromatography, ion exchange chromatography, affinity chromatography, metal binding, immunoaffinity chromatography, and high performance liquid chromatography.

Following introduction and expression of a first and second nucleic acids into a plant cell, a transgenic plant cell may be regenerated into a transgenic plant.

Plant regeneration by tissue culture techniques is well established. For example, plant regeneration from cultured protoplasts is described in Evans et al, Handbook of Plant Cell Cultures, Vol. 1: (MacMillan Publishing Co. New York, 1983); and Vasil I. R. (ed), Cell Culture and Somatic Cell Genetics of Plants, Acad. Press, Oriando, Vol. I, 1984, and Vol. III, 1986. Plants have been successfully micropropagated in vitro by organogenesis or somatic embryogenesis including, but not limited to, all major species of sugarcane, sugar beet, cotton, fruit and other trees, legumes and vegetables. The methods for regeneration vary from species to species of plants, but generally a suspension of transformed protoplasts containing copies of the heterologous gene is first provided. Callus tissue is formed and shoots may be induced from callus and subsequently rooted. Alternatively, embryo formation may be induced from a protoplast suspension. These embryos germinate to form mature plants. The culture media will generally contain various amino acids and hormones, such as auxin and cytokinins. Shoots and roots normally develop simultaneously. Efficient regeneration will depend on the type of explant, the physiological condition of the explant and physical and chemical media of the explant during culture, and on the history of the culture.

Once a plant is regenerated, the plant may be cultured to set seed. Subsequently, seed oil may be extracted. Methods for extracting seed oil are known in the art and include, but are not limited to, mechanical methods, solvent based methods or combinations thereof. Exemplary mechanical methods of oil extraction include the use of oil presses, an expeller, and a mortar and pestle. Exemplary solvent based methods of oil extraction include use of the solvents hexane or petroleum ether. The extracted seed oil may be further purified and/or refined by known methods.

In the instance where members of the green algae from Chlorophyceae are modified for altered fatty acid content, extraction of the harvested algae may be the most obvious method to recover oil. In this case the oil would not be "seed oil", but represent a similar source of oil for industrial purposes, such as biofuel.

Uses of the extracted seed oil are known in the art and include, but are not limited to, the production of edible oils and non edible oils. Exemplary uses of non edible seed oil are known in the art and include, but are not limited to, the production of biofuels, cosmetics, lubricants, plastics, nylon, pharmaceuticals and plasticizers. In one aspect of the present invention, the gene product associated with fatty acid metabolism alters the seed oil content and/or composition. Further, seed oil produced using a method of the invention, may be useful as biofuel and in particular, biodiesel.

As used herein, "seed oil content" refers to the amounts or weight of oil obtained by standard extraction methods from seed or plant tissues or structures rich in oil.

As used herein, "seed oil composition" refers to the chemical makeup of the oil, preferably in terms of fatty acid chain length and degree of saturation. Saturation refers to the extent to which C:C bonds are replaced by C:H bonds.

As used herein, "biofuel" refers to fuels derived from biological materials. Biofuel may be derived by harvesting plants high in sugar content and subsequently fermenting the sugar into ethyl alcohol; or by harvesting the cellulose content of a plant and converting the cellulose into simple alcohols by fermentation or other compounds that can be used for fuels; or by harvesting the biological material of a plant and chemical or enzymatic conversion of said material into a diesel fuel substitute; or by harvesting plants oil or animal oil and processing it into biodiesel. As used herein, "biodiesel" typically refers to mono alkyl esters of fatty acids derived from renewable lipid feedstocks, such as vegetable oils or animal fats, for use in compression ignition (diesel) engines or other lipids from biological sources modified for use in diesel and similar engines. Sources of biodiesel include animal fats, vegetable oils, soy, rapeseed, jatropha, mahua, mustard, flax, sunflower, palm oil, hemp, field pennycress, and algae.

Seed oil content and composition of transformed plants comprising a gene product associated with plant fatty acid metabolism may be identified by Gas liquid chromatography (or gas chromatography). This method refers to an approach to separate volatile components of a mixture. A gas chromatograph uses a flow-through narrow tube known as the column, through which different chemical constituents of a sample pass in a gas stream (carrier gas, mobile phase) at different rates depending on their various chemical and physical properties and their interaction with a specific column filling, known as the stationary phase. As the chemicals exit the end of the column, they are detected and identified electronically. The function of the stationary phase in the column is to separate different components, causing each one to exit the column at a different time (retention time). Other parameters that can be used to alter the order or time of retention are the carrier gas flow rate, and the temperature. Generally, substances are identified qualitatively by the order in which they are eluted from the column and by the retention time of the analyte in the column.

Other assays to assess seed oil content I composition that may be suitable for use in the context of the present invention include, but are not limited to, analytical supercritical fluid extraction (SFE) with carbon dioxide as the extraction solvent (S. L. Taylor et al. (1993) Journal of the American Oil Chemists' Society, vol. 70, pp 437-439.

EXAMPLES

Unless otherwise stated, all DNA manipulations (restriction digests, fragment purification ligation, bacterial transformation and plasmid screening were carried out using standard methods.

Purified fragments of the first and second nucleic acids that are free of vector backbone may be used in the context of the invention. In general, plasmid backbones may be removed as they may complicate fluorescent in-situ hybridization analysis (FISH) screening downstream and would introduce antibiotic markers. First nucleic acid to Second nucleic acid ratio may be 10:1 (Mole:Mole). About 30 μg of mixture used per million protoplasts, or 1 μg of DNA mixture used per microprojectile preparation.

Common selection agents may be used such as hygromycin and Phosphinothricin, and the degree of reporter gene activity (or resistance to selection agents) may be correlated to the gene copy number. The selectable marker is linked to the gene(s) of interest.

Transformed callus or explants are placed under selective conditions for a period of 2-6 months with frequent subculturing. Following (or during) selection, regeneration is initiated. Standard methods are used to recover events. Molecular biology techniques may be used to verify the presence of the vector DNA (and copy number). Typically, 100-400 calli are obtained per transformation event.

Example 1: Isolation of a First Nucleic Acid

In this example an *Arabidopsis* 26S rDNA sequence was isolated. The plasmid pJHD2-19a, containing a portion of the *Arabidopsis* 26S rDNA gene (see FIG. 1) has been described previously (US Publication No: 20060143732). For use as a first nucleic acid, the plasmid was digested with XhoI and a 1.5 kb fragment containing the rDNA segment was gel purified away from plasmid sequences.

Example 2: Assembly of a Second Nucleic Acid

In this example a nucleic acid construct is generated comprising three fatty acid biosynthesis genes.

Figure 3:
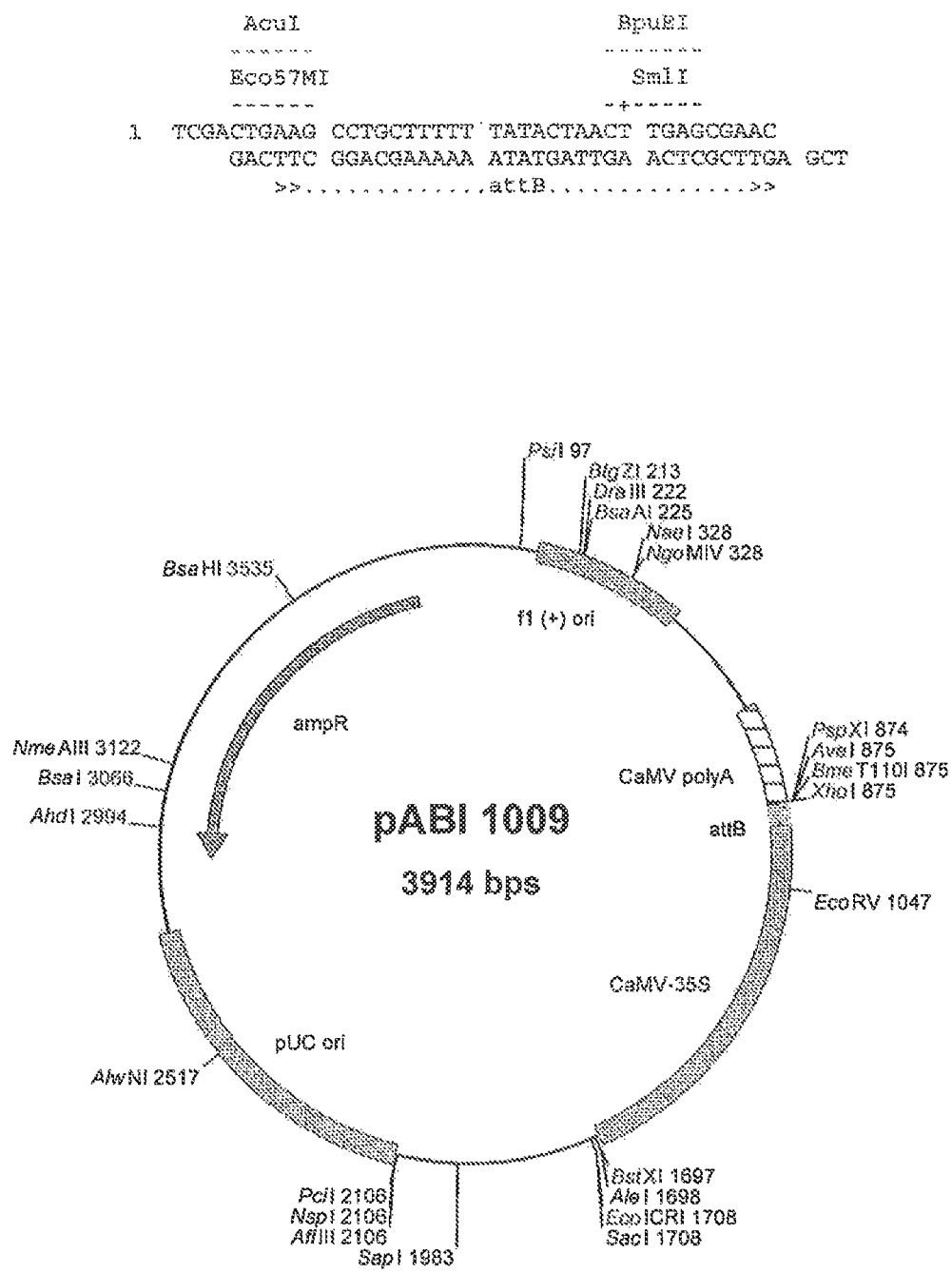
FIG. 3: Upper panel: A double stranded oligo containing an attB site with Xho1 and SalI compatible single-stranded extensions at the 5' and 3' ends respectively [top strand: SEQ ID NO: 1; bottom strand: SEQ ID NO: 2]. Lower panel: map of recombinant plasmid pABI1009

Generation of High Erucic Acid (HEA) vector backbone: A 14 base oligo, 5'-CGCGGCCGCGGTAC-3' [SEQ ID NO: 22] was self annealed to generate a double stranded NotI linker with KpnI compatible single-strand extensions at either end. This was then ligated to KpnI digested plasmid pABI1006 (FIG. 2, upper panel) to yield the recombinant plasmid pABI1007 (FIG. 2, lower panel). A double stranded oligonucleotide containing an attB site with XhoI compatible single-stranded extensions at the 5' and 3' ends respectively (FIG. 3, upper panel) was ligated to XhoI digested pABI1007 and recombinant plasmid pABI1009 was obtained (FIG. 3, lower panel) with the attB site inserted in the sense orientation with respect to the CaMV 35S promoter and terminator sequences. Subsequently a 564 bp XhoI fragment containing the BAR gene coding sequence was excised from plasmid pAgIIa (FIG. 4, upper panel) and inserted into XhoI digested pABI1009 in the sense orientation with respect to the 35S promoter, attB and terminator sequences to yield the plasmid pABI1012 (FIG. 4, lower panel). Prior to use in transformation, pABI1012 was linearized by digestion with ScaI.

Figure 5:
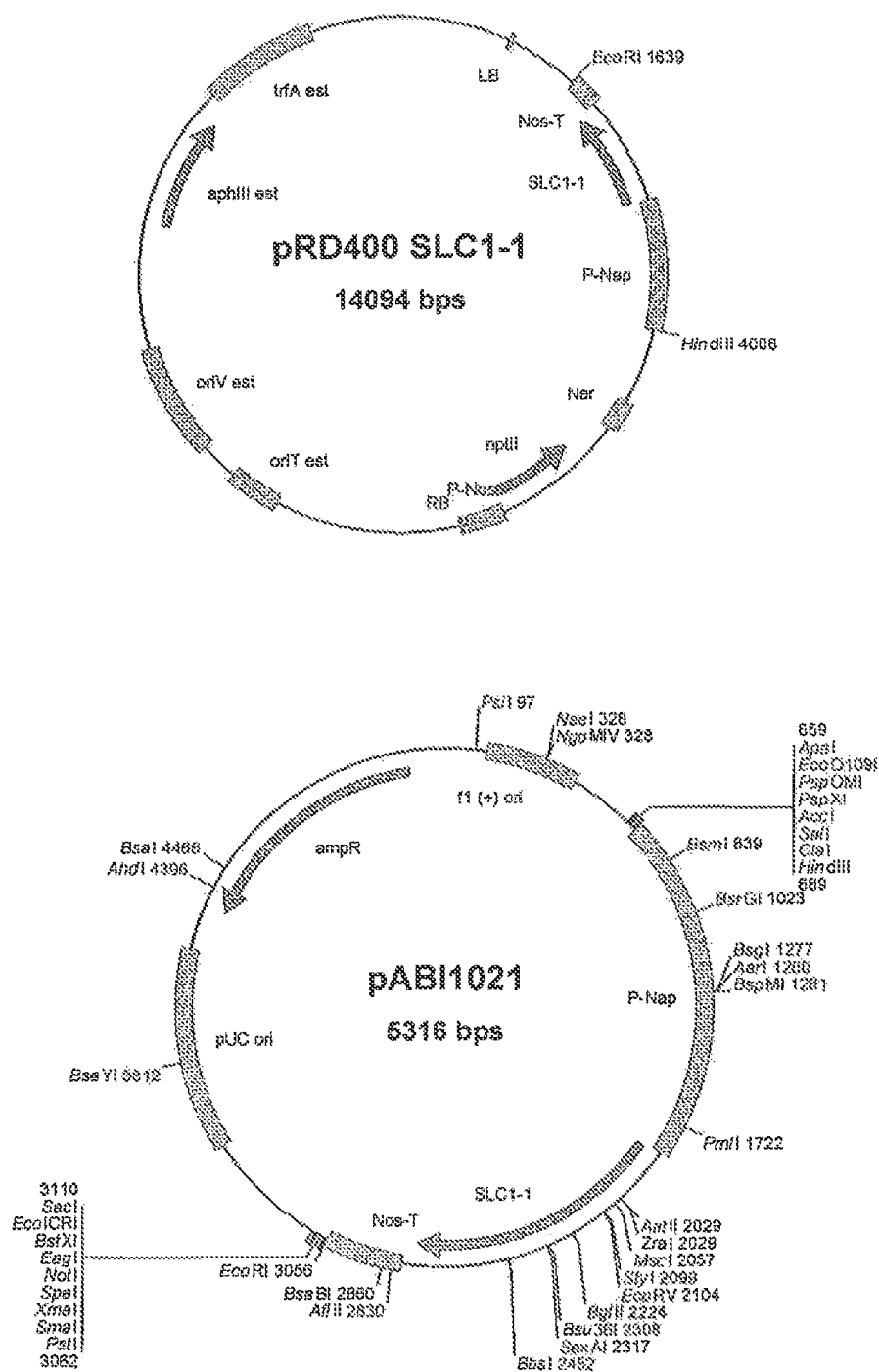
FIG. 5: Upper panel: map of pBS35S-attB-BAR construct pRD400 ySLC1-1. Lower panel: map of plasmid pABI1021

Assembly of the 3-enzyme expression cassette: To facilitate subsequent cloning steps, the y-Slc1-1, n-FAE1 and at-FAE1 expression cassettes were each individually subcloned into pBluescript SK+ as follows:

SLC1-1: A 2367 bp EcoRI/HindIII fragment containing the napin promoter-ySlc1-1 gene-Nos terminator was excised from pRD400 ySlc1-1 (FIG. 5, upper panel) and ligated into the EcoRI/HindII sites of pBluescript to yield the plasmid pABI1021 (FIG. 5, lower panel).

n-FAE1: A 3203 bp PvuII fragment containing the napin promoter-nFAE1 gene-Nos terminator was excised from pRD400 nFAE1 (FIG. 6, upper panel) and ligated into the SmaI site of pBluescript SK+ to yield the plasmid pABI1024 (FIG. 6, lower panel).

at-FAE1: A 3255 bp PvuI/EcoRI fragment containing the napin promoter-atFAE1 gene-Nos terminator (FIG. 7, upper panel) was excised from pNapin-FAE1 and ligated into the EcoRI/SmaI sites of pBluescript SK+ to yield the plasmid pABI1020 (FIG. 7, lower panel).

Figure 8:
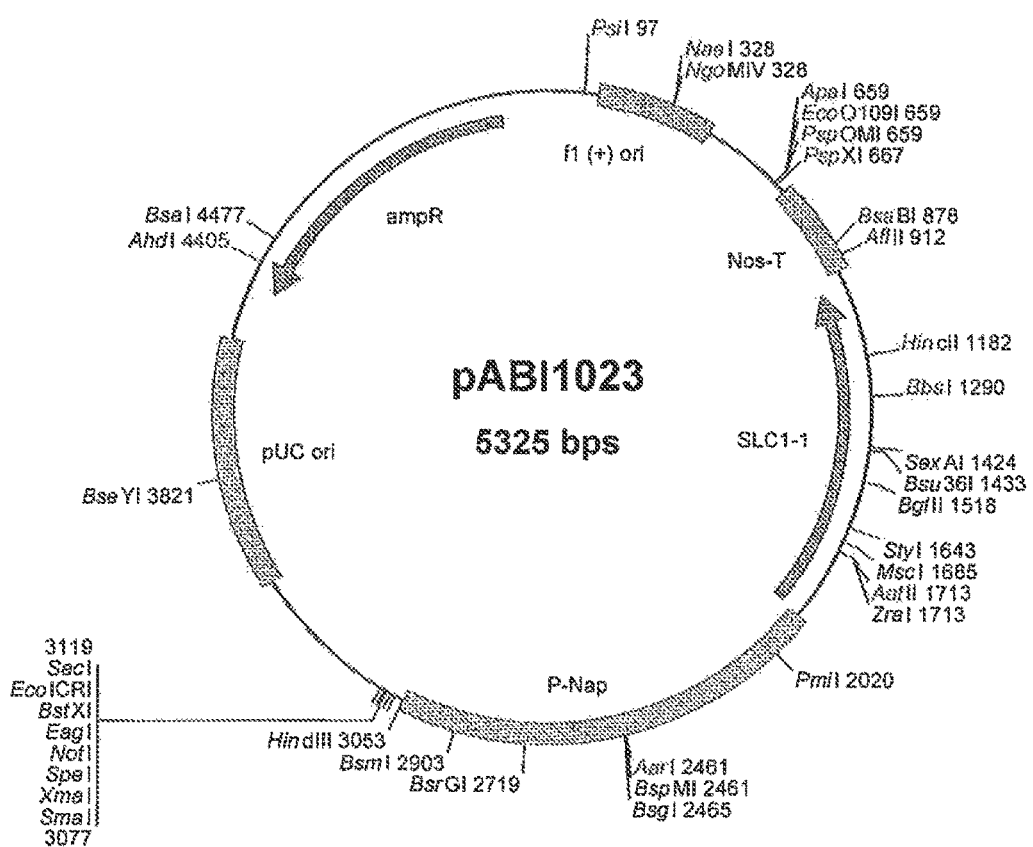
FIG. 8: map of intermediate plasmid pABI1023
Figure 9:
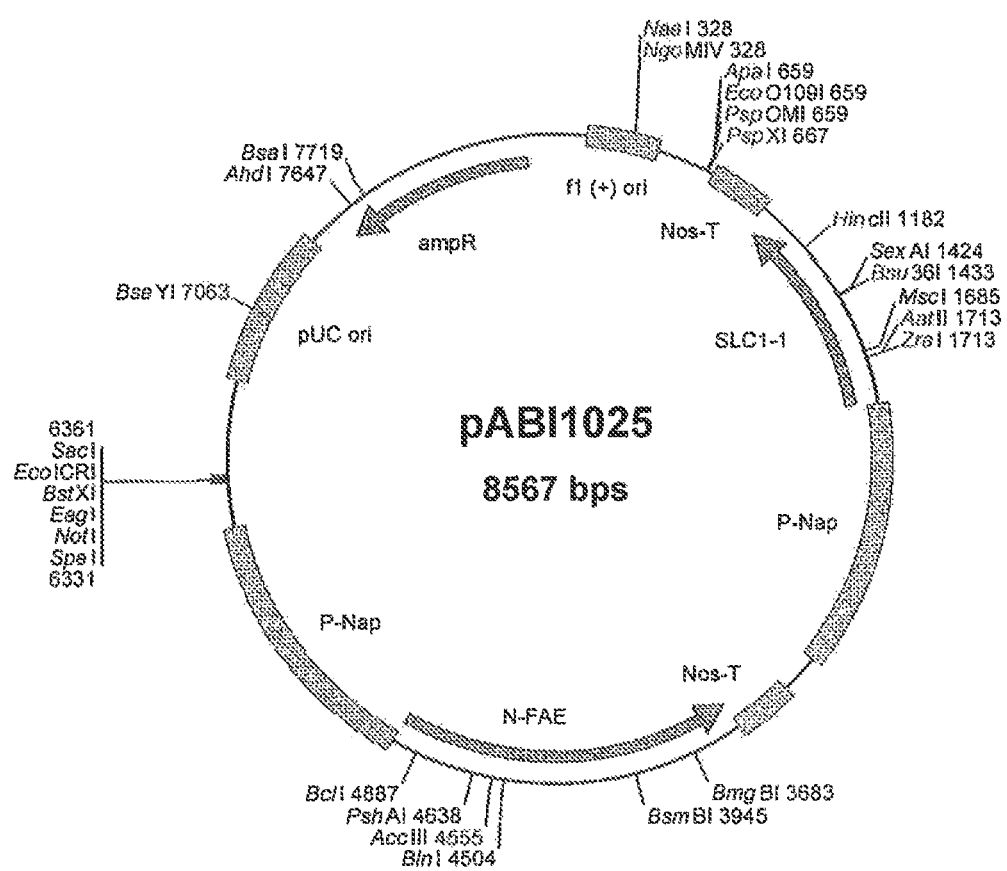
FIG. 9: map of intermediate plasmid pABI1025
Figure 10:
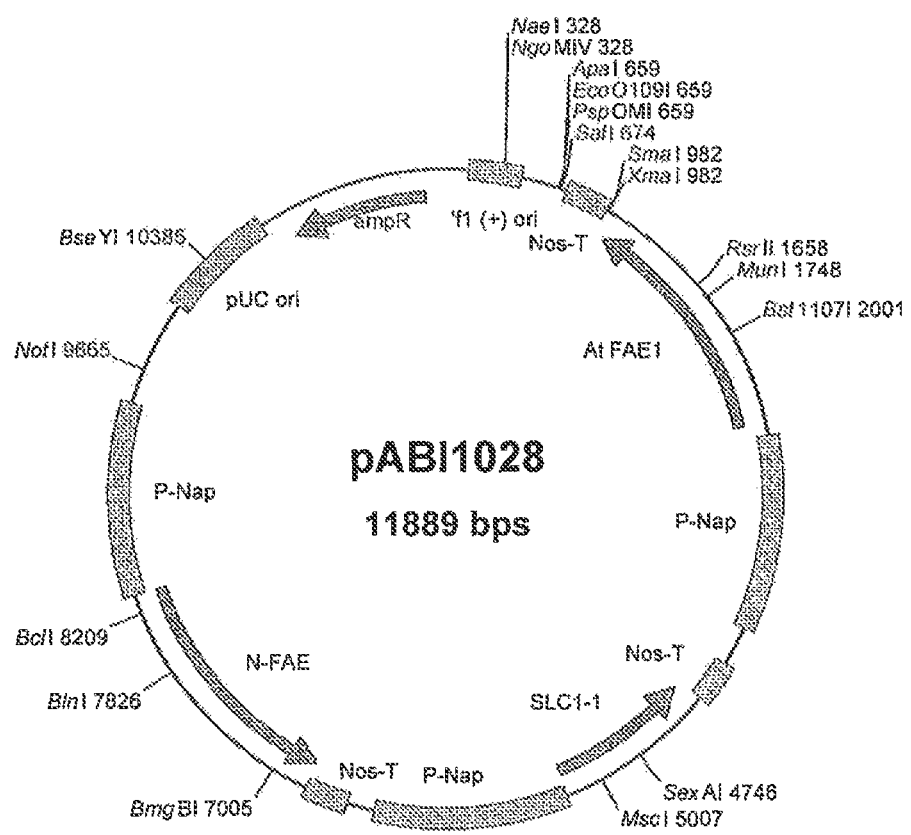
FIG. 10: map of intermediate plasmid pABI1028

The individual expression cassettes were then sequentially cloned onto a single plasmid backbone pBluescriptII SK+. Firstly, a HindIII/SmaI fragment containing the ySLC1-1 expression cassette of pABI1021 (FIG. 5, lower panel) was ligated into the HindIII/HincII sites of pBluescript SK+ to yield intermediate plasmid pABI1023 (FIG. 8). Next, a HincII/SacI fragment containing the nFAE1 expression cassette (FIG. 6, lower panel) was excised from pABI1024 and ligated into the SacI/SmaI sites of intermediate plasmid pABI1023 to generate intermediate plasmid pABI1025 (FIG. 9). Finally, a NaeI/NotI fragment containing the atFAE1 expression cassette (FIG. 7, lower panel) was excised from pABI1020 and ligated into the PspOMI/NaeI sites of intermediate plasmid pABI1025 to yield intermediate plasmid pABI1028 (FIG. 10) containing all three expression cassettes in the same orientation with respect to one another.

Figure 11:
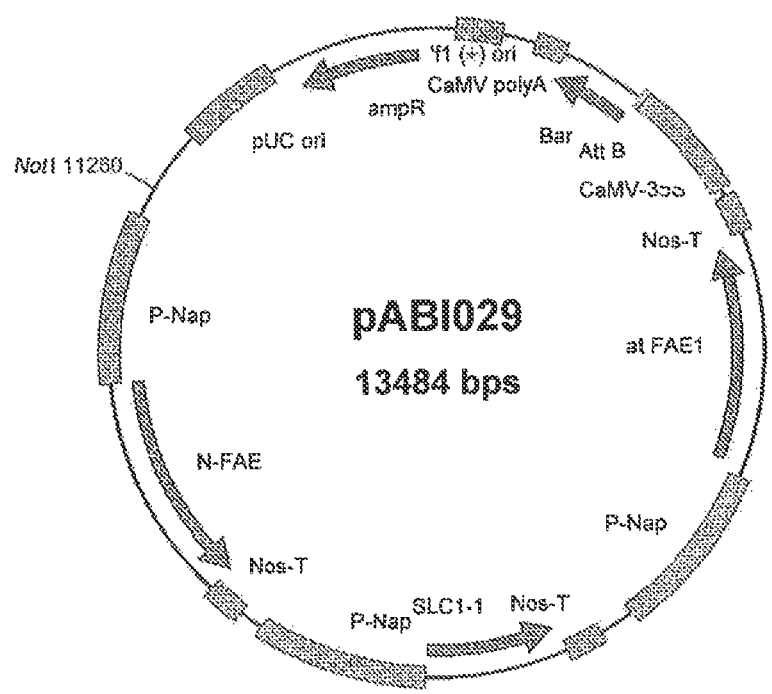
FIG. 11: map of the HEA plasmid pABI1029

Final assembly of HEA vector: To assemble the final HEA vector, a NotI fragment containing the CaMV 35S promoter-attB-BAR-CaMV terminator cassette was excised from pABI1012 (FIG. 4, lower panel) and cloned into the compatible PspOMI site of pABI1028 such that the BAR cassette was in the same orientation as the ySLC1, nFAE1 and atFAE1 cassettes, yielding the second nucleic acid (HEA vector; pABI1029; FIG. 11). Prior to use in transformation, the plasmid was linearized by digestion with Not1 and the linear double stranded DNA fragment was purified.

Example 3: Transformation of *Brassica napus* with First and Second Nucleic Acids In this example, protoplasts were used as starting material and a composition comprising of a first and second nucleic acids were introduced into the protoplasts. The first nucleic acid comprised the rDNA fragment from Example 1, whereas the second nucleic acid comprised the Not1 fragment from Example 2. These two nucleic acids constructs were introduced into freshly isolated protoplasts. In general, to obtain *Brassica* protoplasts, 60-80 newly expanding leaves of plantlet cultures (2-3 per plantlet) were harvested under sterile conditions and placed in a Petri plate (see Table 1 for media and buffer formulations). Bottom leaf surfaces were gently scored. The leaves were then placed bottom side down in 100×25 mm Petri plates containing 15 to 20 ml of Enzyme B2 solution (about 20 to 30 leaves per 100×25 mm Petri plate). Petri plates were then sealed with Parafilm™ and leaves incubated overnight (15 to 20 h) at 22° C. to 25° C. in the dark without shaking. After overnight treatment the plates were agitated gently by hand and incubations continued for about another 30 min. The digested material, consisting of a crude protoplast suspension, was then filtered by passage through a 63µ nylon screen and the filtrate collected. The debris was washed by addition of an equal volume of 17% B5 wash solution and the filtrate was combined with previous filtrate. The filtered protoplast suspension was dispensed into 50 ml conical centrifuge tubes and centrifuged at 100 g (800 rpm) for 8 minutes (no brake). The protoplast enriched fraction (5-10 ml) was carefully removed and transferred to fresh 50 ml conical tubes and 40 ml of WW5-2 wash solution was added per tube. The resulting suspensions were gently mixed by inversion then centrifuged at 100 g for 5 minutes. After centrifugation the supernatants were carefully decanted and discarded, while the pellets consisting of an enriched protoplast fraction were retained. Protoplasts were resuspended and pooled in a small volume of WW5-2 solution, then allowed to settle at which point the packed cell volume (PCV) was noted. Subsequently the protoplast pellet was gently resuspended and the suspension stored at 4° C. for 30-60 min.

The density of the protoplast suspension was determined by counting a small aliquot with a haemocytometer. Protoplasts were then pelleted by centrifugation (100 g for 3 minutes) then resuspended in WMMM solution to a density of $2 \times 10^6$ protoplasts per ml. 0.3-0.5 ml of protoplast suspension was then dispensed into 15 ml falcon tubes and 30 µl of DNA mixture (consisting of a 10:1 molar ratio of linear rDNA fragment to linear HEA Not1 vector fragment in sterile dH$_2$O) was added to protoplast suspension and mixed by shaking. PEGB2 solution (10× volume of DNA, i.e. 300 µl) was then added drop by drop to protoplast/DNA mixture, while tube was continuously shaken. The protoplast/DNA/PEG mixture was incubated for 20-25 min with periodic gentle shaking. Subsequently WW5-2 solution was gradually added in two stages; first a 5 ml aliquot of WW5-2 was added to the protoplast/DNA/PEG mixture which was then allowed to incubate for 30 minutes, after which time a second 5 ml aliquot of WW5-2 was added followed by an additional 10 min incubation. After the second addition of WW5-2 and subsequent incubation, the protoplasts were carefully resuspended and then pelleted by centrifugation at 100 g for 5 min. The protoplast pellet was resuspended in 10 ml of WW5-2 solution then pelleted by centrifugation at 100 g for 5 min. The pellet was washed once more in 10 ml of WW5-2 then pelleted by centrifugation at 100 g for 3 min. The washed protoplast pellet was resuspended in K3P4 culture medium at a density of $1 \times 10^5$ protoplasts per ml, as determined using a haemocytometer; and 1.5 to 2 ml of the suspension was dispensed per 60×15 mm petri plate (Falcon 1007). The sealed plates were maintained in plastic boxes with cardboard lids at about 22-25° C., 16 h photoperiod, in dim fluorescent light ($25 \ \mu Em^{-2} \ s^{-1}$).

After 4-5 days the protoplast cultures were supplied with 1-1.5 ml of medium consisting of a 1:1 mixture of K3P4 medium and EmBedB1 medium (If volume in plate exceeded 2.5 ml after feeding then excess volume transferred to additional 60 ml plates). The plates were then resealed and placed under dim light (in plastic box with cardboard lid for 1-2 days then under medium light (by removal of cardboard lid).

After about another 4-5 days, the protoplasts were embedded as follows: a 3:1 mixture of K3P4: EmbedB1 medium was added to each plate, bringing the total volume to 7 ml. The plate contents were then transferred to a 100×75 mm plate. Finally 3 ml of lukewarm Agarose medium (2.1% SeaPlaque™ agarose in EmbedB1 medium, autoclaved for 20 min then allowed to cool) was added, the plate was swirled to mix and then allowed to solidify. Plates were then sealed and cultured under dim light conditions for 1-2 days followed by culture in medium light conditions. After 7 days, embedded protoplast cultures were transferred onto proliferation plates (Proliferation B1 plates; one embedded culture distributed onto 2-3 proliferation plates) with selection (60 mg/L-PPT). Proliferation plates were incubated under dim light for first 1-2 days and then moved to bright light. Green surviving colonies could be observed after 3 to 4 weeks at which point they were transferred to fresh Proliferation B1 plates (for an additional 2 to 3 weeks).

Large calli (minimum about 5 mm) were transferred to Regeneration B2 plates with selection (10 mg/L L-PPT) or without selection. Thereafter calli were transferred to fresh Regeneration B2 plates every 3 to 4 weeks. Shoots typically emerged 5 to 12 weeks after transfer to regeneration plates and once apparent were maintained under bright light conditions. Shoots with normal morphology were then transferred to rooting medium (OB5+0.1NAA) and incubated under dim light conditions (25 $\mu Em^{-2} s^{-1}$). Plantlets were potted in a soilless mix (Sunshine Mix 4; Sun Gro Horticulture) in 6" pots containing fertilizer (5 ml Nutricote 14-14-14 type 100; Sun Gro Horticulture). Pots were maintained in growth room (20° C./15° C., 16 hour photoperiod, with 100-140 $\mu Em^{-2} s^{-1}$ fluorescent and incandescent light at soil level). Plantlets were covered with transparent plastic cups for about one week to allow for acclimatization.

Example 4: Transformation of *Brassica napus* with Another First and Second Nucleic Acids (Plasmid pABI1012)

In this example a second vector comprising heterologous DNA sequences including a BAR herbicide tolerance gene and att recombination site was introduced according to the method to illustrate the utility of the method with a broad range of heterologous DNA. Protoplasts from 2 Canola varieties, *Brassica Napus* Excel or Topaz, were prepared as described above and transformed by PEG mediated direct DNA uptake with a mixture of DNA molecules consisting of a 1:10 molar ratio of linearized pABI1012 core vector to 1.4 kb *Arabidopsis* derived 26S rDNA fragment (XhoI fragment of pJHD2-19a plasmid). Cultured protoplasts were then selected for L-PPT resistance and large resistant calli were subsequently placed under conditions to stimulate plantlet regeneration while at the same time a portion of the callus was reserved for genomic DNA isolation for subsequent Southern analysis. Southern analysis was also performed on DNA isolated from leaves of regenerated TO plantlets.

To identify plants that comprise multiple copies of inserted heterologous genes, a Southern blot screen was carried out on genomic DNA isolated from L-PPT resistant calli and leaves. Purified DNA was quantified by OD 260/280 determination using a Nanodrop fiber-optic spectrophotometer (Model ND-1000; Nanodrop Corp) and then 5-10 µg was digested using the restriction enzyme AseI (New England Biolabs). Digested samples were fractionated on 0.7% agarose 0.5×TBE (45 mM Tris-borate, 1 mM EDTA, pH 8.0) gels, run overnight at 70 volts (constant voltage). The gel was stained with ethidium bromide and photographed on UV light-box and then treated for 20 min in 0.25 M HCL to depurinate the DNA, followed by a 30 min incubation in 0.4M NaOH to denature the DNA. DNA was transferred to a TM-XL (Amersham Biosciences) membrane using a Turboblotter apparatus (Schleicher & Schuell Bioscience) and 0.4 M NaOH as the blotting buffer. Blots were hybridized as follows: membranes were pre-incubated in 20 ml of QuikHyb hybridization buffer (Stratagene) plus 100 µg/ml denatured salmon sperm DNA (Invitrogen) overnight at 65° C. in a hybridization oven (Tyler Research Instruments). The pre-hybridization liquid was then discarded and replaced with 20 ml of QuikHyb solution supplemented with 100 µg/ml denatured salmon sperm DNA as well as the appropriate heat-denatured probe labeled with $^{32}$P-dCTP (alpha-32 dCTP, Redivue Amersham Bioscience) using random primer labeling (Random Primers DNA labeling System, Invitrogen).

Blots were hybridized overnight at 65° C. in a hybridization oven then washed twice for 15 min per wash in 2×SSC, 0.1% SDS at 65° C. then washed twice for 15 min per wash in 0.1×SSC, 1% SDS at 65° C. Blots were exposed to x-ray film (Hyperfilm ECL, Amersham Biosciences) for periods ranging from 1-3 days. Copy number of integrated transgenes was estimated by comparing the signal intensities of the labeled bands to those of standards consisting of known amounts of core vector DNA diluted in wildtype genomic DNA that was digested, fractionated and transferred onto the same blots. Data from Southern blot analysis indicated that a significant number of plants, upwards of greater than 30% of the total events recovered, comprised multiple copies of integrated heterologous DNA, which consisted of substantially identical copies of the inserted heterologous DNA. Further restriction mapping of the inserted DNA in various lines confirmed the substantial similarity of the multiple copies of the heterologous DNA. Copy numbers are typically 2-5 copies, 6-10 copies, or in some cases up to 30-60 copies of introduced vector sequences.

Example 5: Determination of Genomic Location of Multiple Copies of Heterologous DNA by Fluorescent In-Situ Hybridization (FISH) of *Brassica napus*

In this example, transformed plants comprising multiple substantially identical copies of the heterologous genes were analyzed at the chromosome level for localization of the heterologous genes to rDNA arrays. To accomplish this, regenerated plants were allowed to set seed. The seed was germinated and the root tips analyzed by FISH using a probe to 18S rDNA and a probe to the heterologous gene.

As a first step, mitotic blocking of the *Brassica* root tips was carried out as follows: *B. napus* Excel seeds were allowed to germinate between 2 layers of Whatman filter paper #2 moistened with water at 22° C. in the dark for 36 hrs. Root tips of 1-1.5 cm in length were excised and placed in 0.02% 8-Hydroxyquinoline for 8 hours at 15° C. to arrest cells in metaphase. The root tips were then fixed in a cold 3:1 mixture of 95% ethanol and glacial acetic acid and stored at −20° C. After 2 days of fixation, the root tips were washed 3 times in 0.01 M Citric buffer (pH 4.5) then incubated in a cellulytic enzyme solution containing 1.0% Cellulase RS (Karlan, 9286341429), 0.1% Pectolyase Y-23 (ICN 320952) and 0.01M Citric buffer at 28° C. for 2.5 hr. Digested root tips were washed twice in 0.01M citric buffer before placing in dH2O for 30 min. Finally to remove cytoplasm and debris, the root tips were placed in several changes of 60% acetic acid for 20-25 min prior to squashing.

The root tips were squashed onto microscope slides and processed according to methods known in the art: 100 µL 100 µg/ml RNase A (Invitrogen, 12091-021) was dispensed onto a slide containing digested and incubated for 1 hour at 37° C. Slides were washed twice in 2×SSC for 5 min, dehydrated through an ethanol series (70%, 80%, 90% and 100%), 2 min each at R/T (J. T. Baker 9229-01 and Commercial Alcohols Inc, 432526) and then air dried for 10 min. Slides were then incubated in a solution consisting of 70% formamide and 30% 2×SSC for 2 min at 70° C., quenched in cold 70% ethanol and dehydrated through ice-cold ethanol series (80%, 90% and 100%) for 2 min per ethanol concentration. Finally slides were air dried.

For preparation of metaphase spreads, protoplasts could be used as well. Protoplasts were isolated and fixed as described herein. Typically a drop of the fixed protoplast suspension in fixative was dispensed from a Pasteur pipette onto a pre-cleaned microscope slide as described above from a distance of approximately 10 cm. After air-drying, the slides were aged at room temperature for at least 24 hrs prior to hybridization.

For use as FISH probes, purified double-stranded DNA fragments were labeled by nick translation using either biotin-16-dUTP (Enzo Life Sciences) or digoxigenin-11-dUTP (Roche), according to manufacturer's instructions. In some instances, probes were also labeled by PCR reactions in which dTTP was partially replaced by biotin-16-dUTP (1.0 mM, Roche) or digoxigenin-11-dUTP (1.0 mM, Roche).

For hybridization, a probe mix was prepared comprising 2 µl biotinylated probe (FITC green), 2 µl digoxigenin-labeled probe (Rhodamine red), and 26 µl hybridization buffer. The probes were denatured at 70° C. for 10 min, then quenched on ice. The probe mix was then applied onto a slide which was then covered with a 50×22 mm coverslip and sealed with rubber cement. The sealed slides were placed in a hybridization box to maintain humidity and hybridized for 12-20 hours at 37° C.

Following hybridization, the slides were washed in 2×SSC, 42° C. to soak off coverslips. Then slides were washed twice in 50% formamide (EMD FX0420-8) in 50% 2×SSC at 42° C. for 8 min with shaking followed by two washes in 2×SSC at 42° C. for 8 min and finally one wash in 1×PBD at R/T for about 5 minutes. After the PBD wash the slides were drained.

To each slide 60 µl of ice cold mixture 1 was added [Mixture 1 (per slide) 30 µl of 1/500 dilution of Avidin-FITC (Vector Laboratories, A3101, 1:500 dilution) and 30 µl of 1/500 dilution of monoclonal anti-Dig (Sigma, D8156, 1:500 dilution)]. Slides were incubated at 37° C. for 30 min in a humidified chamber. Afterwards, slides were washed in 3 changes of PBD, two min per change with shaking.

To each slide 60 µl of ice cold mixture 2 was added [Mixture 2 (per slide) 30 µl of 1/250 dilution of Biotinylated anti-avidin (Vector Laboratories, BA0300, 1:250 dilution) and 30 µl of 1/250 dilution of anti-mouse Ig-Dig (Chemicon, AQ300D, 1:250 dilution)]. Slides were incubated at 37° C. for 2 hr in a humidified chamber. Afterwards, slides were washed as before in 3 changes of PBD, two min per change with shaking.

To each slide 60 µl of ice cold mixture 3 was added [Mixture 2 (per slide) 30 µl of 1/500 dilution of Avidin-FITC (Vector Laboratories, A3101, 1:500 dilution) and 30 µl of 1/100 dilution of anti-Dig Rhodamine (Roche 1 207 750, 1:100 dilution)]. Slides were incubated at 37° C. for 2 hr in a humidified chamber. Afterwards, slides were washed as before in 3 changes of PBD, two min per change with shaking. Finally the slides were drained, mounted in DAPI/Vectorshield mounting media with DAPI (Vector Laboratories Inc, H-1500) and coverslips sealed to the slides (Fisher Scientific, 12-548-5C) with nail varnish.

The slides were then viewed under a fluorescent microscope and the images recorded.

In general, plant lines that demonstrated multiple copies of the heterologous DNAs also demonstrated that the heterologous DNAs were found in a singular rDNA array, and the chromosome morphology was unchanged from control. This is shown in FIG. 12 (BT12-9). Accordingly, the plants obtained contained multiple copies of heterologous genes of substantial similarity to each other, all located with a singular rDNA array of a plant chromosome.

Typically 10-25% of the transformation events analyzed demonstrate the localization and multicopy features of inserted heterologous DNA to rDNA arrays at the chromosome level.

Example 6: Oil Analysis of *Brassica* Seed Comprising Multiple Copies of the Second Nucleic Acid Comprising Three Fatty Acid Biosynthesis Genes (nFAE1, atFAE1 and ySLC1)

In this example, the seed oil content and composition from transgenic plants comprising multiple copies of three fatty acid biosynthesis genes (nFAE1, atFAE1 and ySLC1) integrated into rDNA arrays were evaluated. Using standard techniques for extraction of seed and Gas Chromatography, seed oil content was and composition was determined (FIG. 13). Plant line BT19-11 demonstrated a significant increase in VLCFA relative to control plants. The level of accumulation of C22:1 and C20:1 is substantially higher than that generally observed in the art, with long chain fatty acid content approaching 50% of the total fatty acid content in seeds of primary transformants.

Example 7: Consistency of Expression of VLCFA Phenotype

Figure 14:
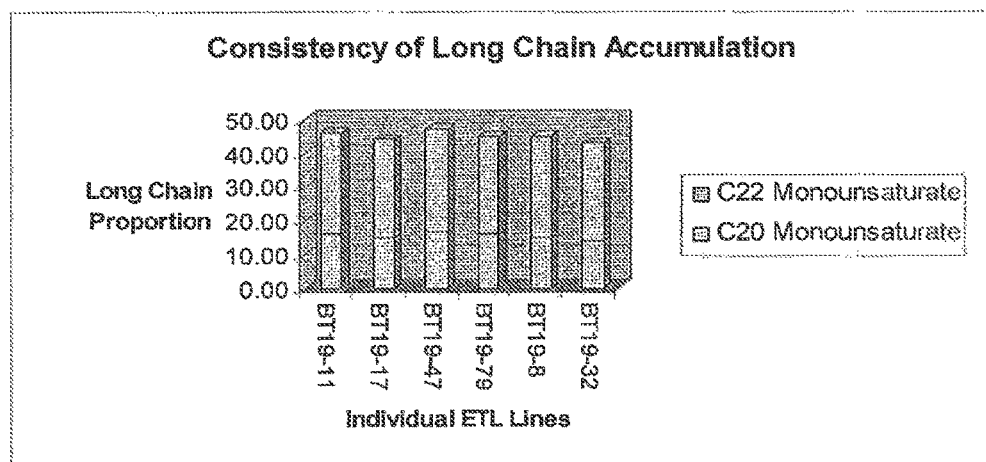
FIG. 14: Proportion of long chain fatty acids in multiple independent transformation events of *Brassica napus* expressing three heterologous genes for altered fatty acid metabolism.

In this example, the consistency of expression seen from heterologous genes inserted into rDNA arrays is illustrated. Multiple independent transformation events of *Brassica napus* showed similar accumulations of C22:1 and C20:1 fatty acids, thus demonstrating a predictable pattern of expression. FIG. 14 shows the accumulation of long chain fatty acids from 6 independent transformation events wherein multiple copies of the nFAE1, atFAE1 and ySLC1 genes are localized to rDNA.

Example 8: Preparation of a Second Nucleic Acid Comprising a Gene Capable of Providing Resistance to Bialaphos In this example, a glutamine synthetase (GS) gene is isolated from *B. napus*. Nucleic acid construct comprising GS is introduced into plant cells. Transformed plant cells with multiple copies of the GS gene in rDNA are selected for use in the regeneration of bialaphos resistant plants. Single copies of the introduced GS gene will not provide a detectable level of bialaphos resistance.

To isolate the native GS gene, total RNA was extracted from *B. napus* 7 day old seedlings that were grown in the dark. Poly A mRNA was isolated from total RNA using a PolyAT Tract™ kit (Promega), and then cDNA was synthesized using a SuperScript Choice™ System for cDNA synthesis (Gibco-BRL). Directional cDNA libraries were constructed by ligation to Lambda ZipLox™ (Gibco-BRL). Ligation products were packaged using Gigapack Gold™ (Stratagene) and libraries obtained using an *E. coli* Y1090 host strain.

To obtain GS cDNA, PCR was performed on pools of clones using the following primer pairs, which contained XhoI restriction site extensions for subsequent manipulation.

Forward Primer (GSFW1):
[SEQ ID NO: 23]
5'-<u>CTCGAG</u>ATGAGTCTTCTGACCGAT-3'

Reverse Primer (GSRV1):
[SEQ ID NO: 24]
5'-<u>CTCGAG</u>TCAAGGATTCCAAAG-3'

Figure 15:
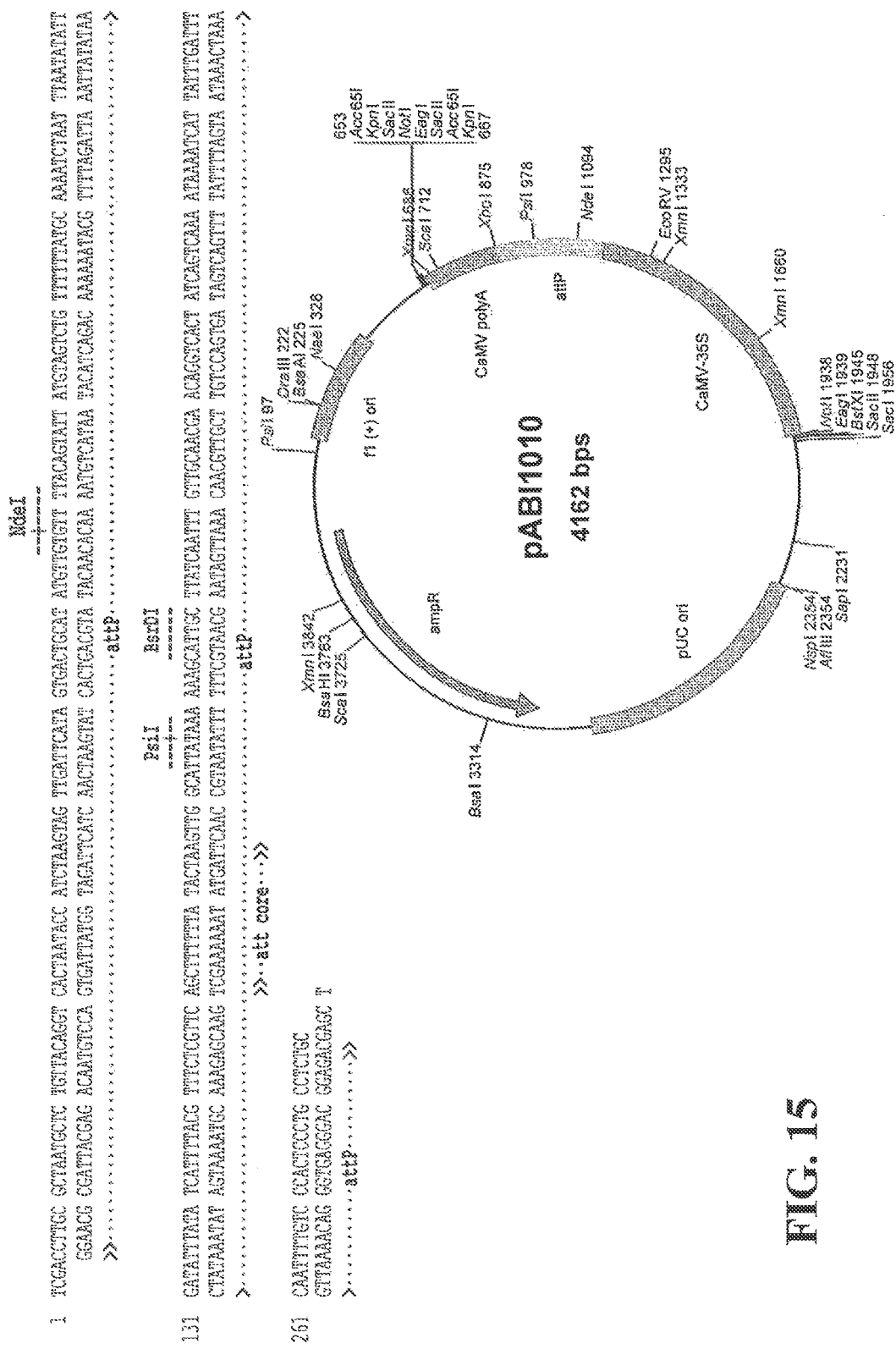
FIG. 15: Sequence of lambda attP regions obtained (upper panel) [Top strand: SEQ ID NO: 3; bottom strand: SEQ ID NO: 4] and attP containing vector pABI 1010 (lower panel).
Figure 17:
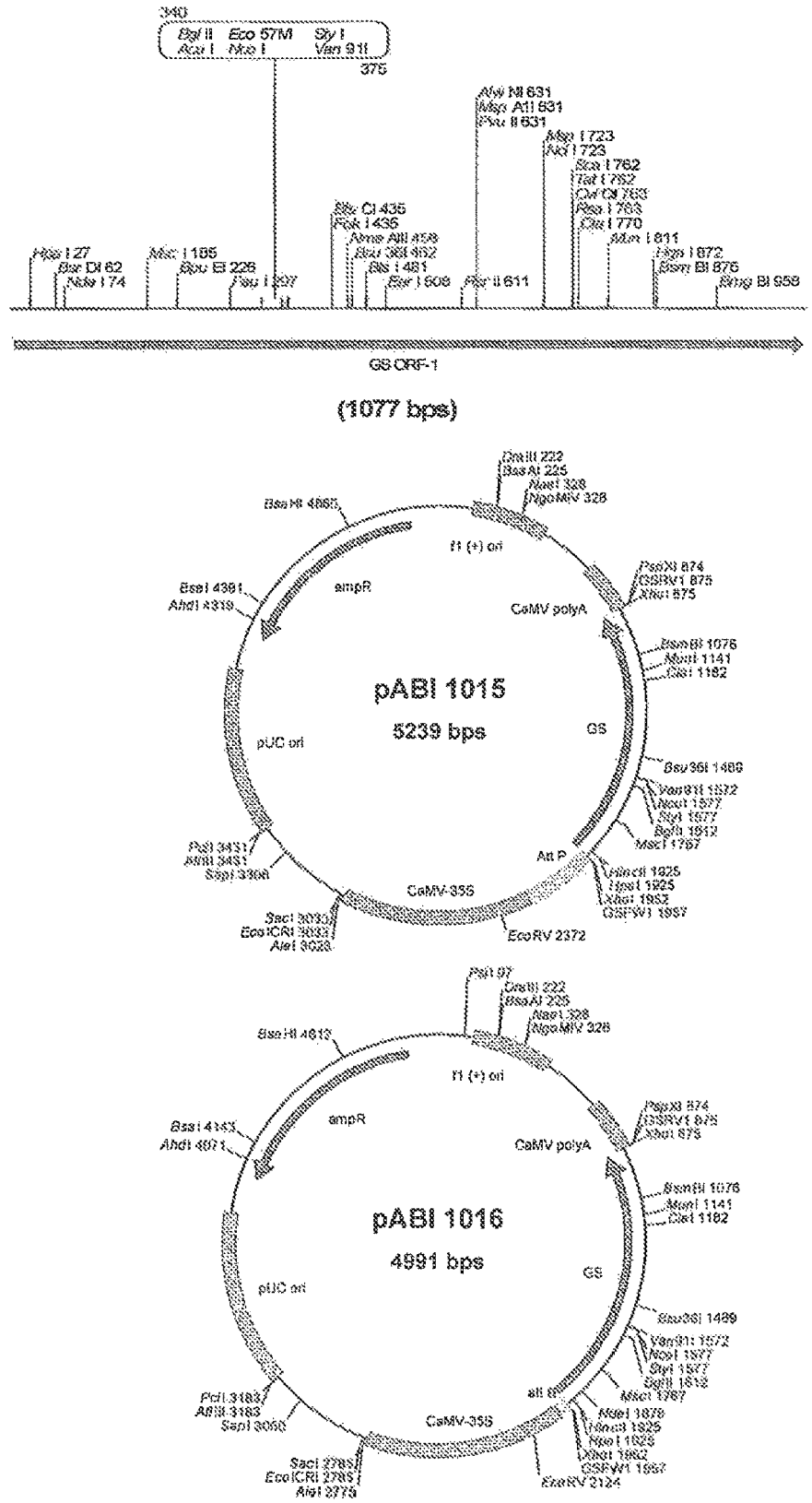
FIG. 17: Map of glutamine synthetase core vectors pABI1015 and pABI 1016.

The resulting PCR products were analyzed by agarose gel electrophoresis. Amplicons in the desired size range (about 1.1 kb) were excised from the gel, purified and then cloned into a pCR4Topo vector. Plasmid inserts were then sequenced and compared to published Genbank sequences for cytoplasmic GS genes. One clone containing an intact GS gene sequence for the cytoplasmic isoform GS1.1 (see sequence comparison with Genbank accession X76736, FIG. 16; Schock et al. Plant Physiol, 105: 757, 1994) was chosen for further studies. The DNA fragment comprising the GS coding sequence was excised from the pCR4Topo vector using the flanking XhoI sites, then cloned into XhoI linearized pABI1009 (FIG. 3) or pABI1010 (FIG. 15) vectors to yield the pABI core vectors pABI1015 and pABI1016 (FIG. 17). The vector pABI1016 comprises the CaMV 35S promoter controlling the expression of the GS gene.

Example 9: Transformation of *Brassica* with pABI016 (Comprising the GS Gene)

In this example a first nucleic acid comprising rDNA as described in example 1 and the vector pABI1016 as described in example 8 were used to transform *Brassica* as described herein. Briefly, *Brassica napus* Excel protoplasts were prepared and transformed with a DNA mixture consisting of a 1:10 ratio of linearized pABI016 and rDNA sequence. After recovery phase, protoplasts were selected in L-PPT containing medium according to the following schedule: 28 days post transformation: 0-5 mg/l L-PPT, followed by 1-2 weeks at 20 mg/L L-PPT, followed by 3 weeks at 60 mg/L L-PPT. At this latter stage, healthy green calli were observed on plates of transformed material while control mock transfected material was dead and or browning [figure difficult to interpret when in grayscale] (see FIG. 18, upper panel).

DNA was purified from CaMV 35S-GS transformed *brassica* that are L-PPT resistant and analyzed for the presence of the transgene by PCR. Since the GS gene is highly conserved between *brassica* and *Arabidopsis* the presence of the CaMV 35S promoter sequences was probed. 100 ng of DNA was subjected to PCR using the PCR primers shown below which amplify a 400 bp portion of the CaMV 35S promoter.

[SEQ ID NO: 25]
35S-FW1: CAGCGTGTCCTCTCCAAATG

[SEQ ID NO: 26]
35S-RV1: AGCACGACACTCTCGTCTAC

All the transformed plant cells that are bialaphos resistant contained the expected 400 bp PCR amplicon (see FIG. 18, lower panel) which co-migrated with the amplicon obtained from amplification of pABI1016 (lane labeled PL). As control, DNA from three different isolates of *B. napus* Excel cells were tested in parallel. No amplification products were observed.

Single copies of the endogenous GS gene are not capable of conferring resistance to 60 mg/L L-PPT, as demonstrated by the inability of the mock transfected *brassica* to survive bialaphos challenge endogenous GS. Accordingly, plant lines were recovered that were resistant to a selective agent based on the ability to produce plant lines with multiple copies of an inserted gene.

Example 10: Isolation of a First Nucleic Acid from Soybean

In this example a soybean 26S rDNA nucleotide sequence was isolated by PCR. Two PCR primer pairs were designed based on 26S rDNA nucleotide sequence conservation across plant species (see FIG. 19A, upper panel).
*Glycine MAX* rDNA Primer Set 1

[SEQ ID NO: 27]
Primer 1F: 5'CGATAGCGAACAAGTACC3'

[SEQ ID NO: 28]
Primer 1R: 5'CTGCCACTTACAATACCC3'

Expected amplicon size: 2984 bp
*Glycine MAX* rDNA Primer set 2

[SEQ ID NO: 29]
Primer 2F: 5'CCAATCGGGCGGTAAATTC3'

[SEQ ID NO: 30]
Primer 2R: 5'CCCGTCGCGTATTTAAGTC3'

Expected amplicon size: 3015 bp

Figure 19A:
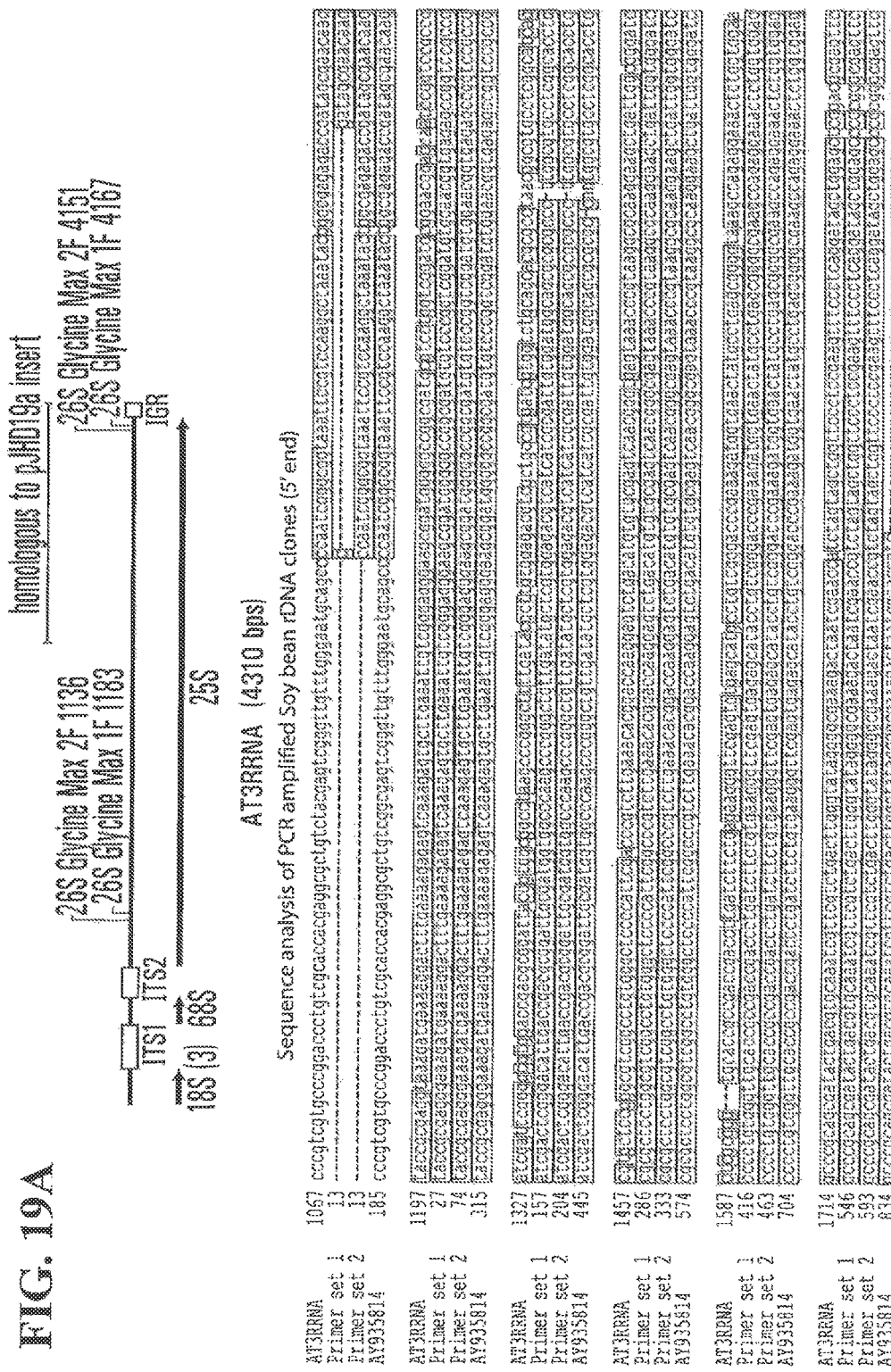
Figure 19B:
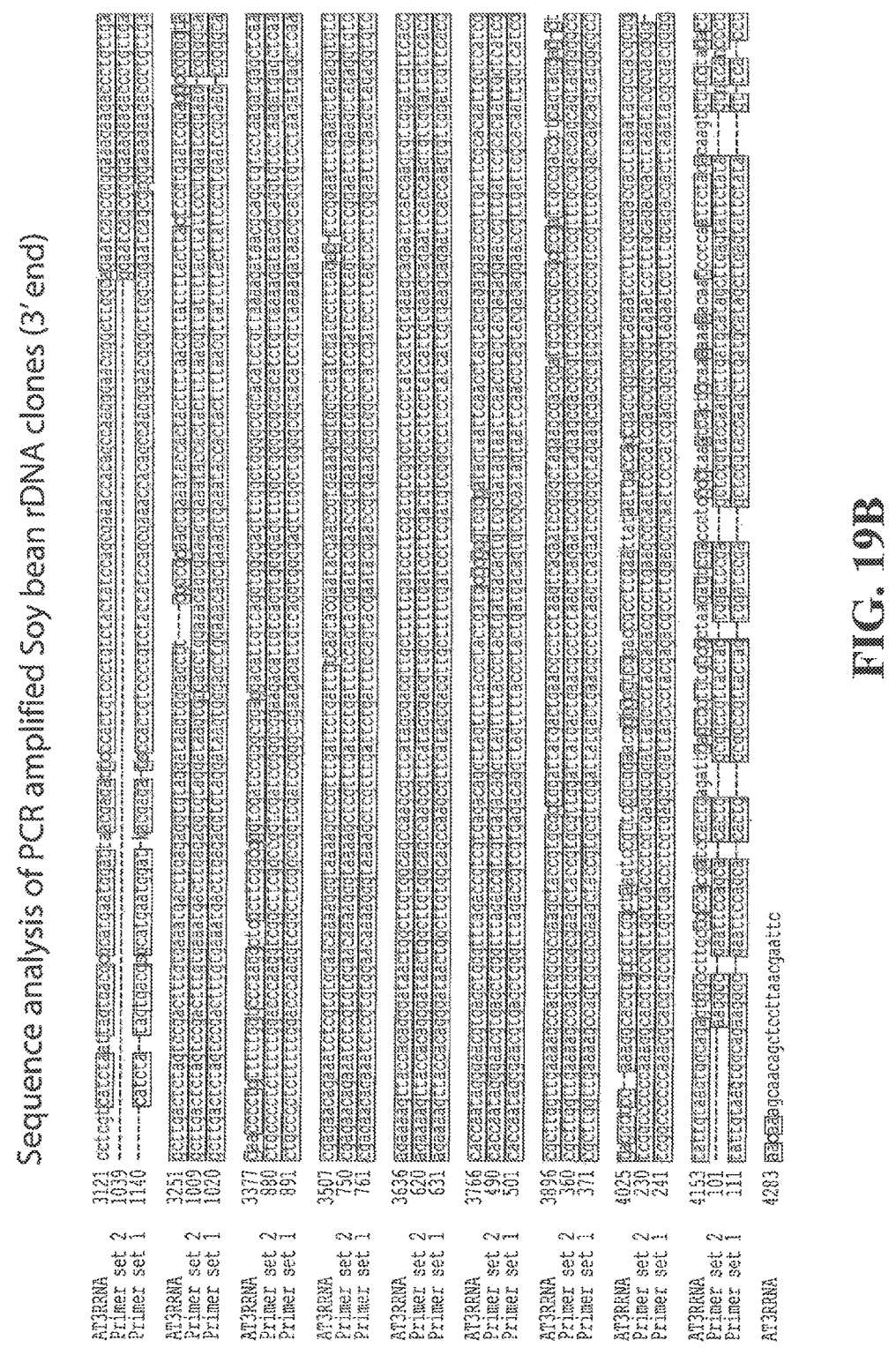
Figure 20:
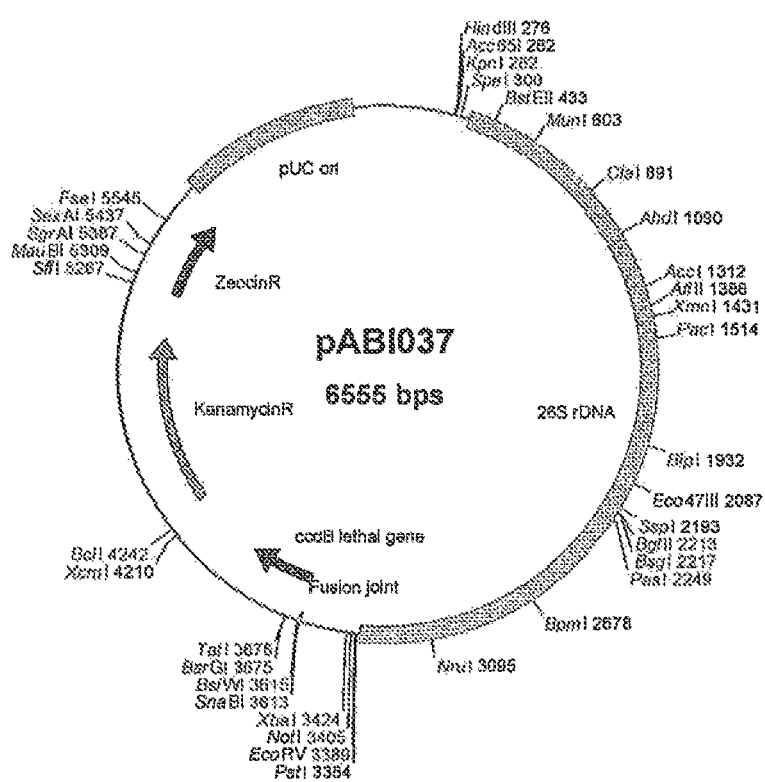
FIG. 20: Map of plasmid pABI037 [See SEQ ID NO: 16 for the nucleotide sequence of the plasmid]

PCR was carried out on soybean genomic DNA according to standard protocols. Amplification products were first analyzed by agarose gel electrophoresis to confirm that the molecular weights of the amplicons were as expected. Subsequently the amplicons were excised from the agarose gel, purified and sub-cloned into the vector pCR-BluntII-TOPO (InVitrogen; according to manufacturer's protocols). Subclones were end-sequenced via automated di-deoxy sequencing, using a variety of primers (m13F, m13R, T7 and T3). The resulting sequence information were compared to a 913 bp portion of the Soybean 26S rDNA gene (Genbank accession number AY935814) as well as the known *Arabidopsis* full length 26S rDNA sequence (Genbank accession number X52320). As shown in FIG. 19A, lower panel and FIG. 19B, both primer pairs amplified DNA fragments of expected size and demonstrated identity to the published 913 bp soybean 26s rDNA sequence at the 5' end sequenced portion of the amplicon; thus confirming that the subclones were bona fide soybean 26 rDNA segments. As only limited Genbank sequence data is available for soybean 26S rDNA, the end-sequenced soybean sequences to the known *Arabidopsis* 26S rDNA (AT3rRNA) genes was also compared. Extensive homology in all sequenced portions of the PCR amplicons was observed. The end sequence data further confirmed that the PCR cloned regions are indeed bona fide soybean 26S rDNA gene segments. Plasmid pABI037 (see FIG. 20, SEQ ID NO: 16) containing the 26S rDNA insert amplified by *Glycine Max* primer set 2 was digested with EcoRI and a 2.6 kB fragment containing most of the 26S rDNA insert was gel purified away from other plasmid derived sequences.

Example 11: Nucleic Acid Construct Comprising a Hygromycin Selectable Marker and a Site-Specific Recombination Sequence for Use in Soybean Assembly of the 35S-attB-HygR cassette: A 1077 bp SmaI fragment containing the coding sequence for the bacterial Hygromycin resistance (HygR) gene was excised from the plasmid pHyg (FIG. 21, upper panel) and gel purified. Subsequently, plasmid pABI1012 (FIG. 21, middle panel) was digested Xho1 to excise the BAR gene sequence, end filled with Klenow and ligated with the SmaI HygR gene fragment, resulting in plasmid pABI034 (FIG. 22, upper panel). The HygR gene was inserted downstream of and in the sense orientation with respect to the CaMV 35S promoter and attB site. For use in the transformation of soybean, the plasmid was digested with NotI and a 2.1 kb fragment containing the CaMV 35S promoter-attB-HygR cassette was gel purified.

Assembly of the 35S-attP-HygR cassette: Plasmid pABI1014 (FIG. 21, lower panel) was digested with Xho1 to excise the BAR gene sequence, end filled with Klenow and ligated to the SmaI HygR gene fragment, resulting in plasmid pABI035 (FIG. 22, lower panel). The HygR gene was inserted downstream of and in the sense orientation with respect to the CaMV 35S promoter and attP site. For use in the transformation of soybean, the plasmid was digested with NotI and a 2.36 kb fragment containing the CaMV 35S promoter-attP-HygR cassette was gel purified.

Example 12: Transformation of Soybean

In this example soybean was used as an exemplary plant species in which to practice the invention. Soybean only has one rDNA array in its genome and it is not pericentric in location. Soybean culture, transformation and selection was carried out essentially as described by Simmonds In: Molecular Methods of Plant Analysis. Jackson and Linskens eds. Springer Verlag, Berlin, Heidelburg, Germany. 2: 159-174, 2002), and as described herein.

Induction and Maintenance of Proliferative Embryogenic Cultures: Immature pods, containing embryos 3-5 mm long, were harvested from host plants cv. Westag 97 and AAFC breeding line X2650-7-2. Pods were sterilized, the embryonic axis excised and explants cultured with the abaxial surface in contact with the induction medium FN Lite (Samoylov et al. 1998) containing 5 mM asparagine, 2.6% sucrose, 20 mg/l 2,4-D, pH 5.0. The explants were maintained at 20° C. at a 20 hr photoperiod under cool white fluorescent lights (35-75 µmol $m^{-2}$ $s^{-1}$), and were subcultured four times at 2-week intervals. Embryogenic clusters were observed after 3-8 weeks of culture and were transferred to 125-ml Erlenmeyer flasks containing 30 ml of embryo proliferation medium, FN Lite containing 5 mM asparagine, 2.4% sucrose, 10 mg/l 2,4-D, pH 5.0 and cultured as above at 35-60 µmol $m^{-2}$ $s^{-1}$ on a rotary shaker at 125 rpm. Embryogenic tissue (30-60 mg) was subcultured every 4-5 weeks.

Transformation:

Cultures were bombarded 3-4 days after subculture. Embryogenic clusters from twelve flasks were used per transformation experiment. All the embryogenic clusters from each flask were blotted dry, placed inside a 10×30-mm Petri dish on a 2×2-$cm^2$ tissue holder (PeCap 1005 µm pore size, B and SH Thompson and Co. Ltd. Scarborough ON, Canada) and covered with a second tissue holder to hold the clusters in place. Immediately before the first bombardment the tissue was air dried in the laminar air flow hood with the Petri dish cover off for 3 min. The tissue, sandwiched between the two holders, was turned over, dried for 1 min, bombarded on the second side and returned to the same culture flask.

Bombardment Parameters:

The bombardment conditions used for the Biolistic PDS-1000/He Particle Delivery System were as follows: 29 in Hg (737 mm Hg) chamber vacuum pressure, 13 mm distance between rupture disc (Bio-Rad Laboratories Ltd., Mississauga ON, Canada) and macrocarrier; the first bombardment used 900 psi rupture discs and a microcarrier flight distance of 8.2 cm, and the second bombardment used 1100 psi rupture discs and 11.4 cm microcarrier flight distance.

Preparation of DNA:

Core vector and rDNA targeting vector fragments were prepared as follows: core vector pABI034 was digested and a 2.36 kb insert containing the 35S promoter, attB site and hygromycin resistance gene was gel purified, ethanol precipitated and resuspended at 100 ng/µl in sterile $dH_2O$; rDNA vector pABI037 was digested with EcoRI and a 2.6 kb fragment containing a portion of the soybean 26S rDNA gene sequence gel purified, ethanol precipitated and resuspended at 100 ng/µl in sterile distilled $dH_2O$. The precipitation onto 1.0-µm-diameter gold particles was carried out as follows: 11.1 µl of 100 ng/µl rDNA and 0.9 µl of 100 ng/µl core vector fragment DNA (10:1 molar ratio of rDNA to core vector fragment) were added to 3 mg gold suspended in 50 µl sterile $dH_2O$ in 0.5 ml microfuge tube and vortexed for 10 s; 50 µl of 2.5 M $CaCl_2$, was added, vortexed for 5 s, followed by the addition of 20 µl of 0.1 M spermidine which was also vortexed for 5 s. The mixture was kept suspended by gently flicking the tube as necessary for 5 min. The gold was then allowed to settle and the supernatant is removed. The gold/DNA was washed twice in 200 µl of 100% ethanol, resuspended in 120 µl of 100% ethanol and aliquots of 8 µl were added to each macrocarrier. The macrocarriers were placed under vacuum to ensure complete evaporation of ethanol and were used within 40 min.

Selection:

The bombarded tissue was cultured on FN Lite medium for 12 days prior to subculture to selection medium (FN Lite, as above, containing 55 mg/l hygromycin added to autoclaved media). The tissue was subcultured 5 days later and weekly for the following 8 weeks. Green colonies generally began to appear between week 3 and 4 on selection medium. Each colony (putative transgenic event) was transferred to a well containing 1 ml of selection media in a 24-well multi-well plate that was maintained on a shaker as above. Colonies continued to appear in the selection medium and were transferred to multi-well plates weekly for the following 4-5 weeks. The media in multi-well dishes was replaced with fresh media every 2 weeks until the colonies were approx. 2-4 mm in diameter and had proliferative embryos, at which time they were transferred to 125 ml Erlenmeyer flasks containing 30 ml of selection medium. The embryogenic colonies were proliferated until sufficient material was available for embryo maturation.

Plant Regeneration:

Maturation of embryo was carried out without selection at environmental conditions described for embryo induction. Embryogenic clusters were cultured on 20×60-mm Petri dishes containing maturation medium similar to that described by Finer and McMullen (1991) and Bailey et al. (1993; MS salts, B5 vitamins, 6% maltose, 0.2% gelrite gellan gum (Sigma), 750 mg/l $MgCl_2$, pH 5.7) with 0.5% activated charcoal for 5-7 days and without activated charcoal for the following 3 weeks. Embryos (10-15 per event) with apical meristems were selected and cultured on a similar medium containing 0.6% phytagar (Gibco, Burlington, ON, Canada) as the solidifying agent, without the additional $MgCl_2$, for another 2-3 weeks or until the embryos, initially green, became pale yellow or partly yellow in color. Mature embryos were desiccated by transferring embryos from each event to empty 15×60-mm Petri dish bottoms placed inside Magenta boxes (Sigma) containing several layers of sterile $H_2O$ saturated Whatman filter paper. The Magenta boxes were covered and maintained in darkness at 20° C. for 5-7 days. The embryos were germinated on solid B5 medium containing 2% sucrose, 0.2% gelrite and 0.075% $MgCl_2$ in 25×100-mm Petri plates (ten embryos or fewer per plate), in a chamber at 20° C., 20-h photoperiod under cool white fluorescent lights (35-75 µmol $m^{-2}$ $s^{-1}$). Within a few days the roots emerged followed by shoots. Germinated embryos with unifoliate or trifoliate leaves were planted in artificial soil (Sunshine Mix No. 3, SunGro Horticulture Inc., Bellevue, Wash., USA), one plantlet per cell of a 72-cell greenhouse flat (100-K, Kord products, Bramalea ON, Canada) that was covered with a transparent plastic lid to maintain high humidity. The flats were placed in a controlled growth cabinet at 26/24° C. (day/night), 18 h photoperiod provided by cool white fluorescent lights and incandescent bulbs at a light intensity of 150 µmol $m^{-2}$ $s^{-1}$. At the 2-3 trifoliate stage (2-3 weeks) the plantlets had strong roots and were transplanted to 12.5-cm fiber pots containing a 3:1:1:1 mix of ASB Original Grower Mix (Greenworld, ON, Canada): soil: sand: perlite and grown at 18-h photoperiod provided by cool white fluorescent lights and incandescent bulbs at a light intensity of 300-400 µnol $m^{-2}$ $s^{-1}$. The photoperiod was reduced to 13 h for flower induction when the plants were at the V 5-6 stage and approx 20-25 cm high (approx. 2 weeks after potting).

Example 13: Fluorescent In-Situ Hybridization (FISH) of Soybean

Embryo Root Tip Germination:

FISH was used to localize the presence of the copies of the heterologous DNAs in the transformed soybean. Desiccated soy embryos were germinated using Whatman filter paper #2 moistened with water and then immersed in B5 liquid medium (Sigma, cat no. G5893) containing 20% sucrose, pH 5.5. Embryo germination was carried out under low light at 20° C. for 8-10 days. The germinated embryos were transferred onto B5 medium containing 0.8 g/l $MgCl_2.6H_2O$, 2% sucrose, pH 5.5 and 0.2% gelrite (Sigma, cat no. G1910) for 2-3 weeks, after which the seedlings were transferred into Sunshine soil mix 3 (Sun Gro Horticulture Canada Ltd) for additional 2 weeks under 28/23° C. and 12 hr photoperiod.

Mitotic Blocking:

For mitotic blocking 1-1.5 cm of root tip was cut and treated with $N_2.0$ at 10.9 ATM (147 p.s.i.) for 1 hr then fixed root tips in ice cold 90% acetic acid for 10 min. Fixed rot tips were washed twice in $H_2O$ for 10 min per wash, change 2 times in and the actively dividing region was transferred to a tube containing 20 µl ice cold enzyme solution (Pectolase Y-23 (1% w/w), Cellulase Onozuka R-10 (2% w/w), 10 mN Sodium Citrate, 10 mM EDTA, pH5.5) and incubated at 37° C. for 30-60 min after which digestion was quenchd by plunge tube into ice. The tube was then filled with ice cold TE and the pellet was genty triturated to wash the root sections. The washed root tips were allowed to settle, the TE was removed and replaced with 100% ethanol and then the root tips were resuspended by gently mixed by inverting the tube. The 100% Ethanol wash was repeated three times. After the final ethanol wash the ethanol was replaced with 30 µl of freshly prepared 90% acetic acid-10% methanol. The root tips were then macerated with a rounded off dissecting needle to release the cells after which they cells were gently resuspended by tapping the tube.

Slide Preparation:

6-8 µl of the cell suspension was dropped on a microscope slide in a humid chamber. Chromatin was crosslinked to slides by exposure to UV light using a crosslinker set to deliver a total energy of 120-125 mJ per square cm. Slides were then used immediately for hybridization or stored at −20° C.

Probe Preparation:

Probes were directly labeled by the method described (Kato A, Albert P S, Vega J M and Birchler J A (2006) Sensitive FISH signal detection using directly labeled probes produced by high concentration DNA polymerase nick translation in maize. Biotech. Histochem. 81: 71-78,). Briefly, a ~3 kB PCR fragment consisting of the 18S rDNA fragment was directly labeled via nick translation with Texas Red-5-dATP (Perkin Elmer, Cat. No. NEL 471) and similarly, a ~3 kb fragment comprising the core vector inserts used for transformation were labeled with Alexa Fluor 488-5-dUTP, (Invitrogen/Molecular Probes, Cat. No. C11397). Both probes were subsequently purified by gel filtration, ethanol precipitated and resuspended in 2×SSC, 1×TE at a concentration of 200 ng/µl.

FISH Hybridization:

5 µl of denatured salmon sperm DNA (140 ng/µl in 2×SSC, 1×TE) was pipetted onto the center of each cell spread. And covered with 22×22 mm plastic cover slip. Root tip DNA (on slide) and probe DNA cocktail were simultaneously denatured by floating in a boiling water bath for 5 min. The probe(s) were then quick-cooled by placing in ice slush and the slides by placing on a pre-chilled metal tray for one to two minutes. The coverslip was then removed, 5 µl of probe mix was pipetted onto the cells and cover slip replaced Slides were then placed in a humid storage container and incubated for 4 hr to overnight at 55'C. Subsequently slide(s) were placed in coplin jar containing room-temperature 2×SSC for up to 5 min to remove the cover slip and excess probe then transferred to a coplin jar containing 55° C. 2×SSC and washed for 2 hr at 55° C. Slides were then removed from coplin jars and excess wash buffer removed by gentle blotting. One drop of pre-mixed Vectashield mounting medium with DAPI was placed on the preads and a 24×50 mm glass cover slip applied. Microscopic observation was carried out using and Olympus BX51 equipped with epifluorescent illumination and images acquired using digital camera (Applied Digital Imaging).

Results:

In general, plant lines of soybean that demonstrated multiple copies of the heterologous DNAs also demonstrated that the heterologous DNAs were found within the singular rDNA array, found on chromosome 13 in soybean. Typically more than 25% of the transformation events analyzed demonstrate the localization and multicopy features of inserted heterologous DNA to rDNA array on chromosome 13.

Example 14: Production of a First Nucleic Acid from Maize

Two primer pairs, located in regions of the 26S rDNA gene that are highly conserved in all plant species and to which TOPO® possesses optimal specificity and priming properties according to standard primer selection algorithms were used to PCR amplify and clone a maize 26S rDNA gene segment.

*Zea Mays* rDNA Primer Set 1:

```
                                        [SEQ ID NO: 31]
    26S Zea Mays 1F: 5' CCGTCCAAGGCTAAATACAG 3'

[SEQ ID NO: 32]
    26S Zea Mays 1R: 5' GAGGCGTTCAGTCATAATCC 3'
```

Predicted amplicon size: 2806 bp

*Zea Mays* rDNA Primer Set 2:

```
                                        [SEQ ID NO: 33]
    26S Zea Mays 2F: 5' GCGGAGGAGAAGAAACTTACG 3'

[SEQ ID NO: 34]
    26S Zea Mays 2R: 5' CCACTCTGCCACTTACAATGC 3'
```

Predicted amplicon size: 3281 bp

Figure 24A:
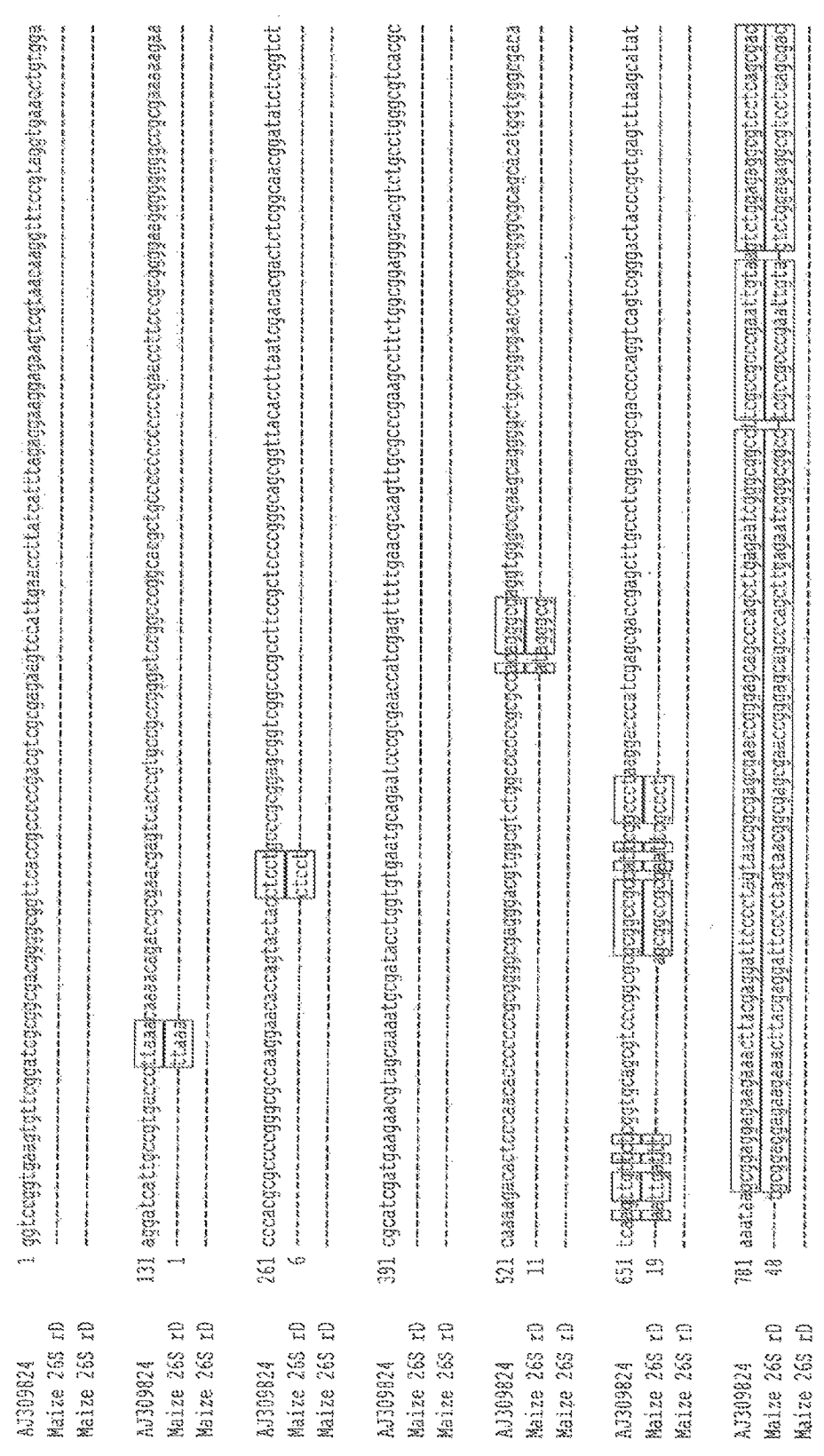
Figure 24B:
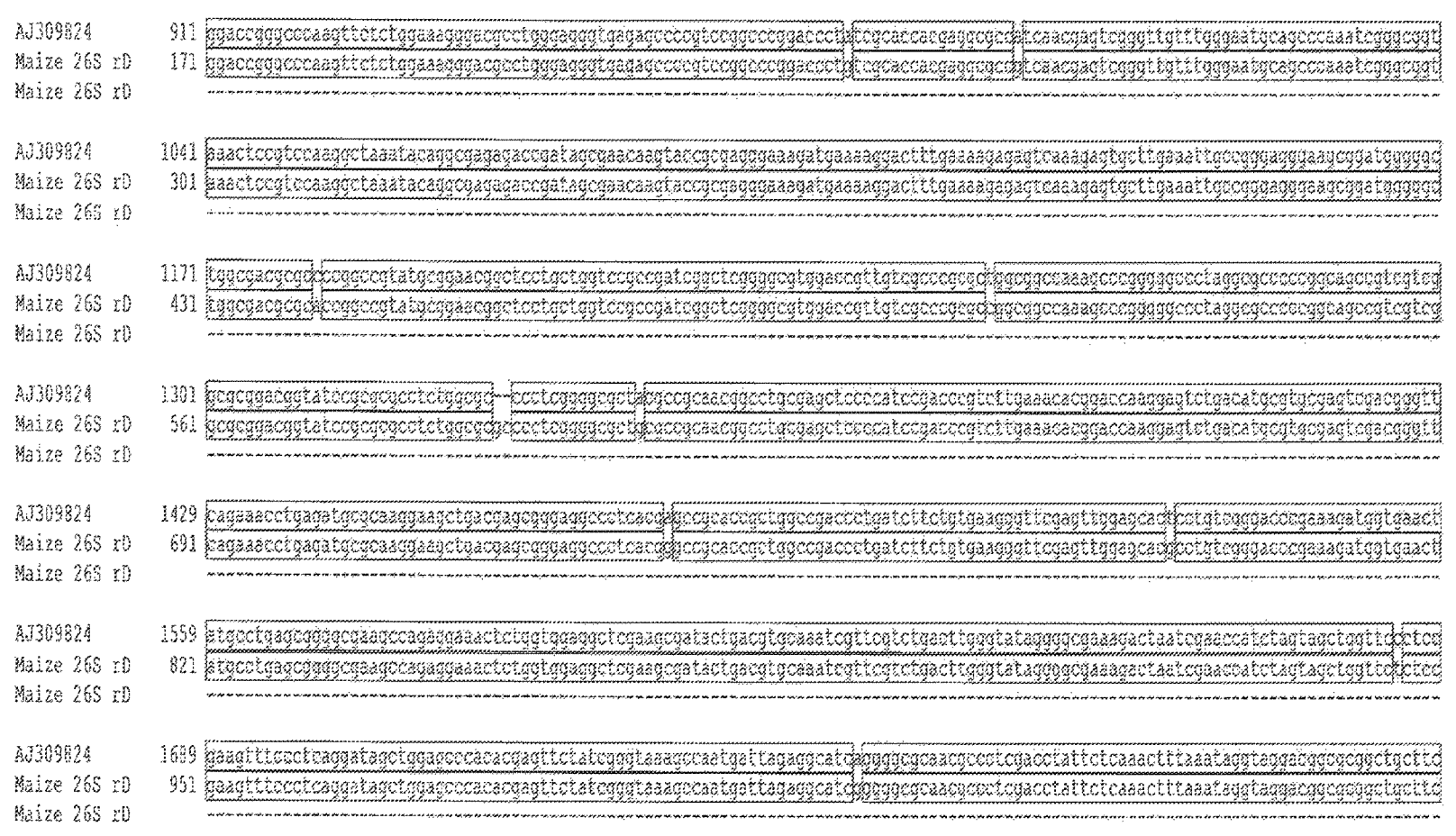
Figure 24C:
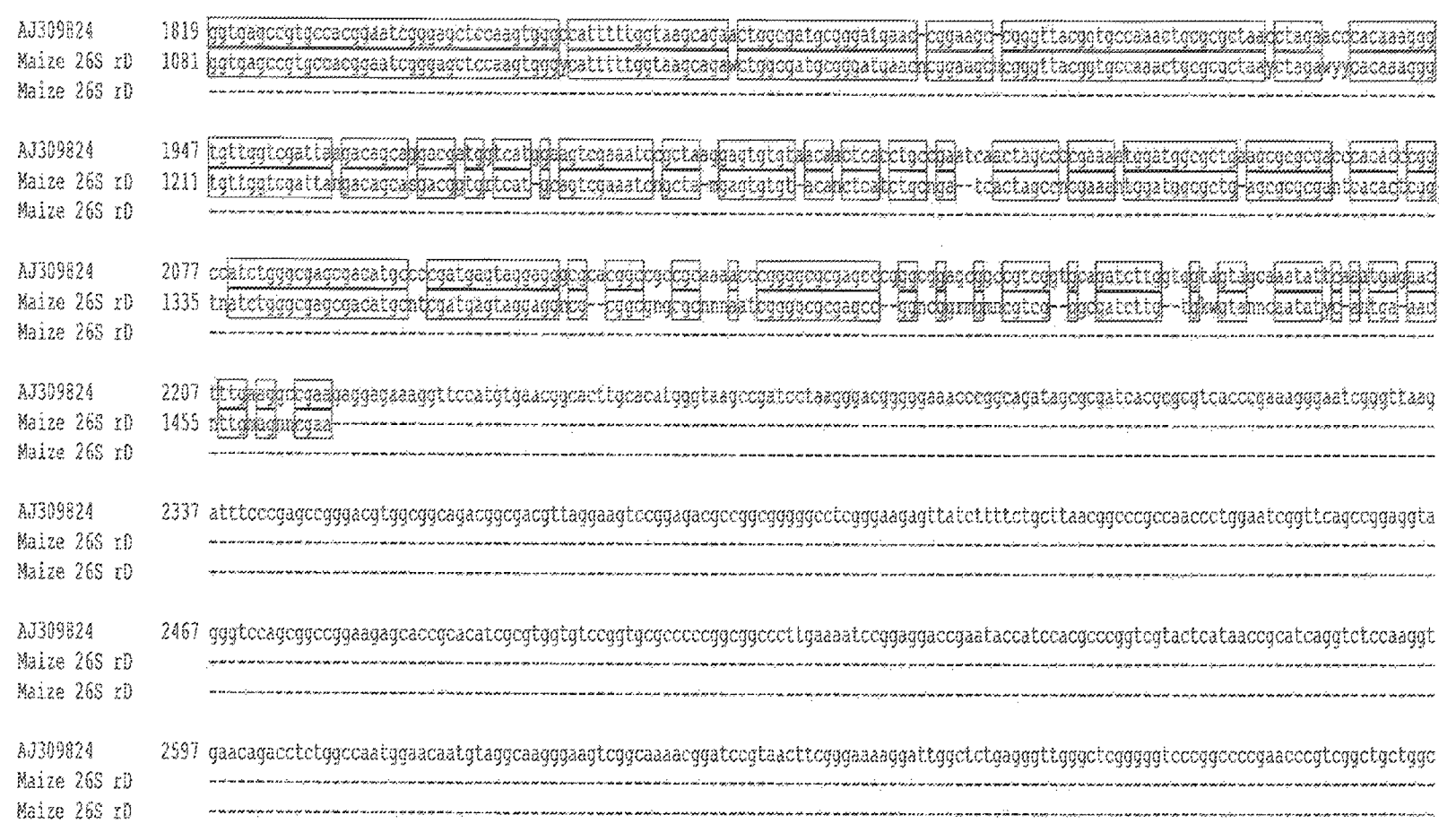
Figure 24D:
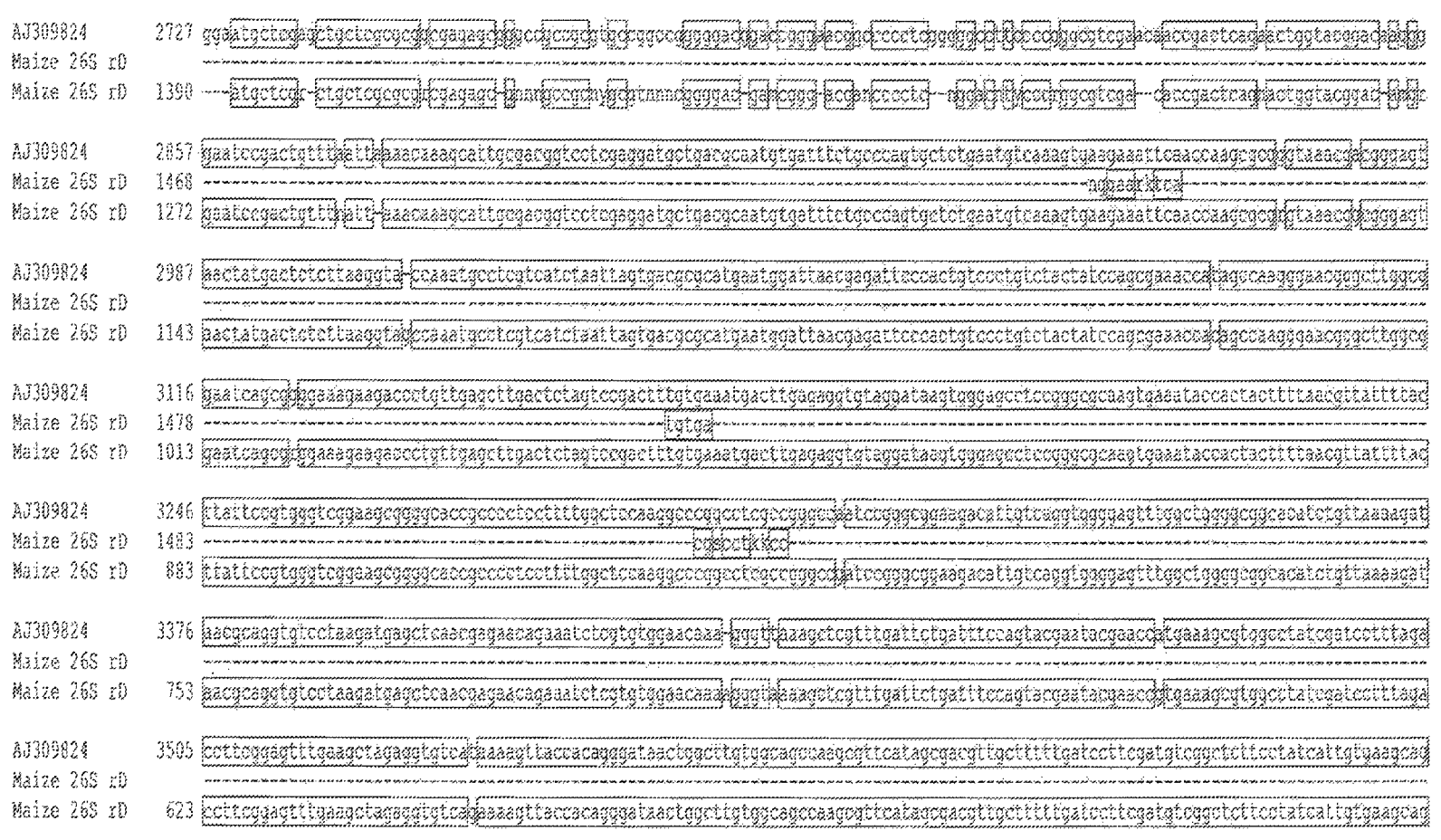
Figure 24E:
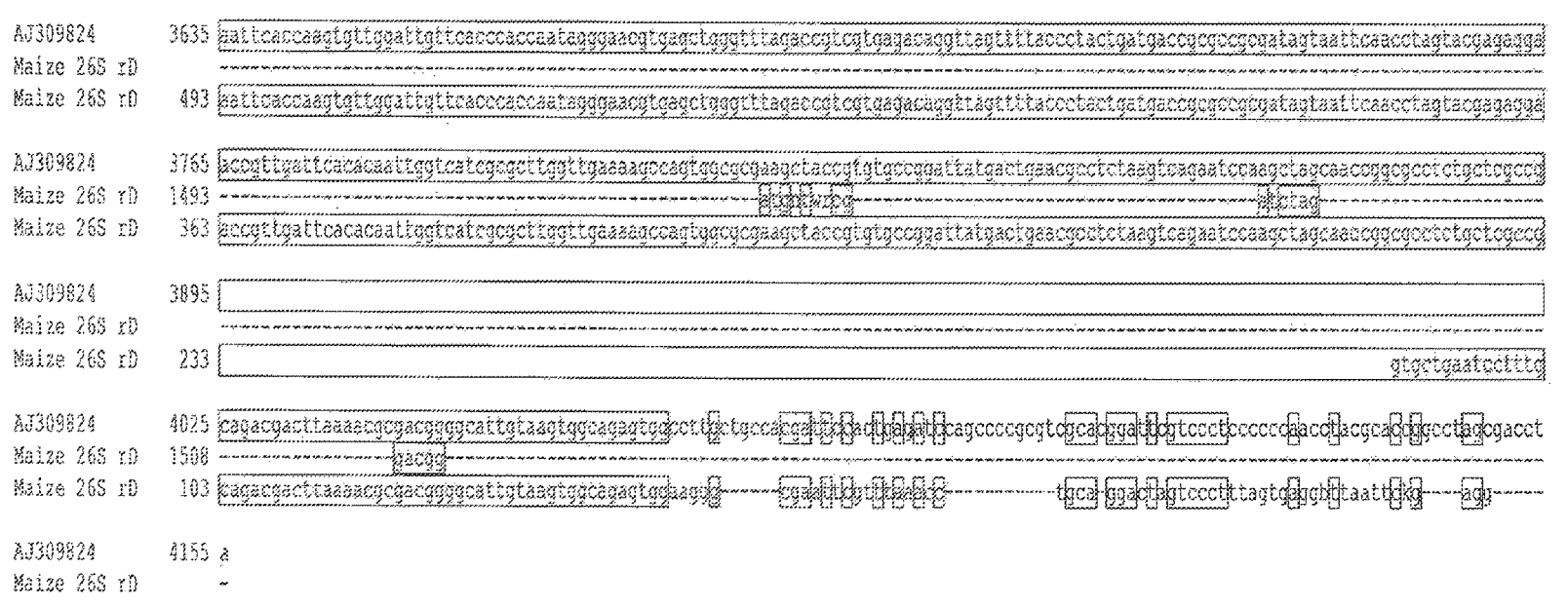
Figure 25:
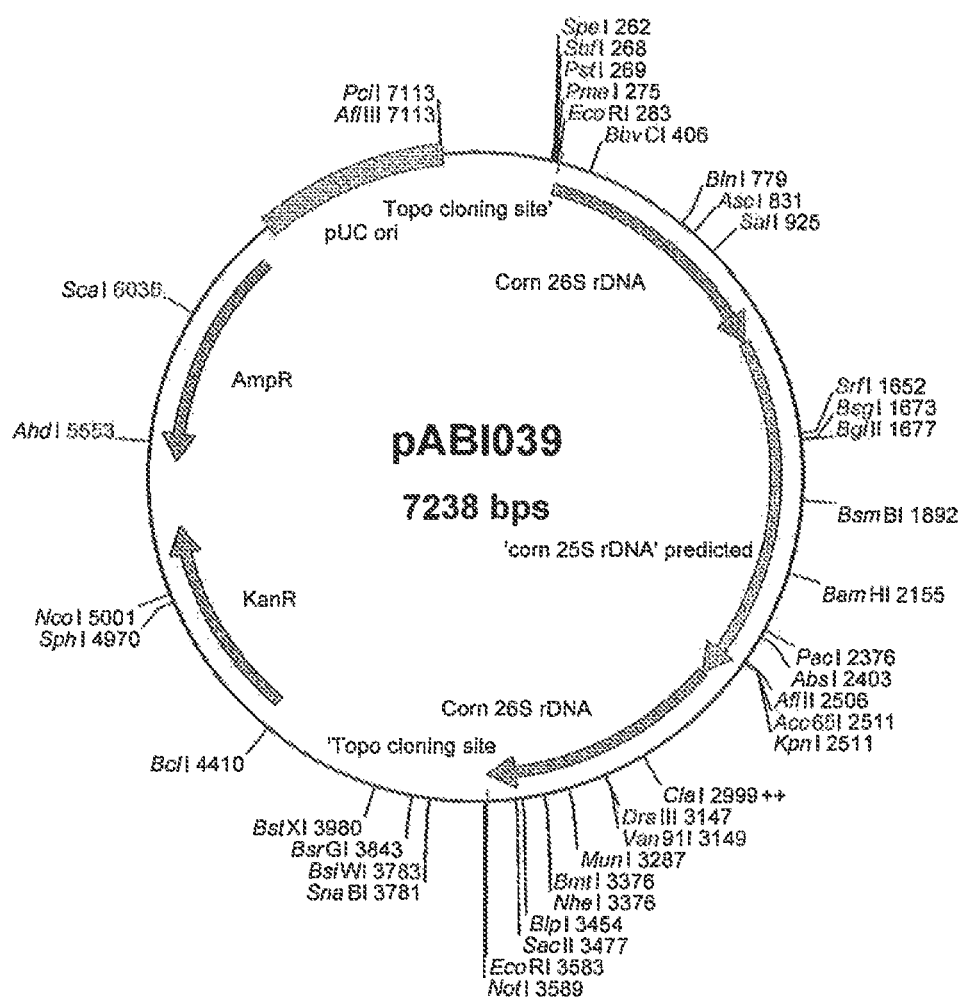
FIG. 25: Map of plasmid pABI039

The positions of the primer binding sites within the Maize 26S rDNA sequence (Genbank accession number AJ309824) are indicated in FIG. 23. Both primer pairs produced amplification products of the expected size. These were excised from the gel and cloned into plasmid pCR4-Blunt-TOPO (InVitrogen; according to manufacturer's protocols). Plasmid inserts were end sequenced via automated di-deoxy sequencing, using a variety of primers (m13F, m13R, T7 and T3) and the sequences obtained were compared to the known maize 26S rDNA gene sequence. As shown in FIG. 24, the consensus sequences obtained from the 5' and 3' ends of the amplification products were highly homologous to and collinear with the 26S rDNA gene sequence, confirming their identity as putative Maize 26S rDNA clones. Plasmid pABI039 (see FIG. 25) containing a 26S rDNA insert (C1) amplified by *Zea Mays* rDNA primer set 2 was digested with EcoRI and a 2.85 kB fragment containing most of the 26S rDNA insert was gel purified for use in maize transformation.

Figure 26:
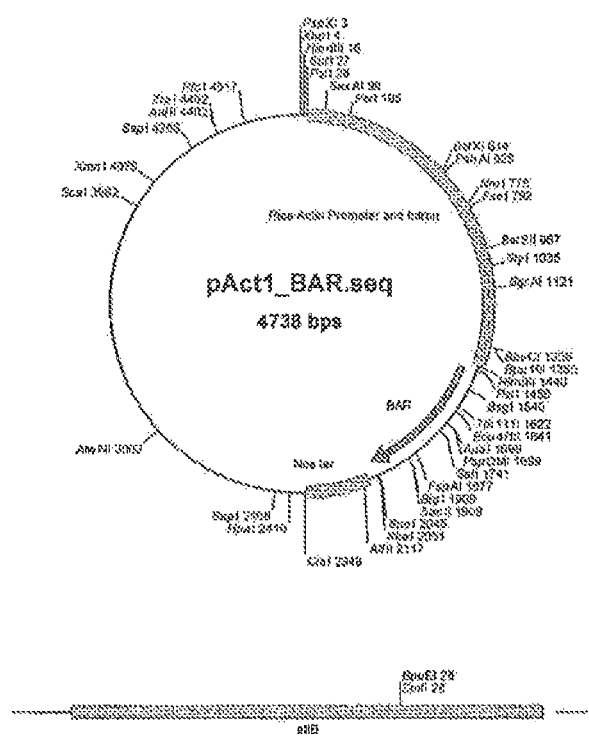
FIG. 26: Upper panel: map of pACT1-BAR. Lower panel: oligo containing an attB site flanked by HindIII and PstI compatible overhangs. [top strand: SEQ ID NO: 20; bottom strand: SEQ ID NO: 21]

Example 15: Production of a Second Nucleic Acid Comprising Heterologous DNA for Maize Transformation The plasmid pACT1-BAR (FIG. 26, upper panel) was digested with Hind III and PstI, removing the Actin promoter. The resulting 3296 bp HindIII/PstI vector fragment was gel purified and ligated to a double stranded oligonucleotide containing an attB site flanked by HindIII and PstI compatible overhangs (FIG. 26, lower panel), resulting in intermediate plasmid pattB-BAR (FIG. 27, upper panel). Subsequently a fragment containing the actin promoter fragment was excised by Hind III digestion of pACT1-BAR. The gel purified 1424 bp HindIII fragment was ligated to HindIII digested pattB-BAR, yielding the plasmid pABI030 (FIG. 27, lower panel) containing the actin promoter upstream and in sense orientation with respect to the attB site and the HygR gene. Finally a GUS expression cassette (consisting of a CaMV 35S promoter, alcohol dehydrogenase intron, GUS coding sequence and NOS terminator) was excised from the plasmid pZO1016 (FIG. 28, upper panel) as a 3419 bp PvuII fragment and cloned into the HpaI site of pABI030 resulting in plasmid pABI031 (FIG. 28, lower panel).

Example 16: Transformation of Maize with First and Second Nucleic Acids

Maize Culture, Transformation and Selection: Maize callus suspension cultures are established from immature dissected A188×B73 embryo explants placed in modified N6 medium (Armstrong and Green. Planta, 164: 207-214, 1985, Songstad et al. Plant Cell Rep. 9, 699-702, 1991; Frame et al. In Vitro Cell Dev Biol Plant, 36: 21-29, 2000; Simmonds et al. Molecular Breeding, 13, 79-91, 2004) and are maintained at 25° C. in darkness. Cultures are routinely passaged by transfer of callus material to fresh modified N6 medium every 2 weeks. An obligatory subculturing is carried out 5 days prior to transformation.

Transformation: On day of transformation gold particles are coated with DNA as described above for Soybean transformation using a DNA mixture consisting of a 10:1 molar ratio of linearized corn 26S rDNA to linearized core vector pABI031. One hour prior to transformation, maize callus is transferred to N6-Mannitol medium. Biolistic transformation is carried out using parameters similar to those described in Klein et al. Proc Natl Acad Sci USA, 85: 4305-4309, 1988. Bombarded calli recover in N6-mannitol for one day and then transferred back to modified N6 medium and cultured an additional 5-7 days. Subsequently, transformed calli is placed under Bialaphos selection (2 mg/L) for up to 12 weeks with regular passaging every 2 weeks. Typically within 6-8 weeks of bombardment, Bialaphos resistant clones emerge from selected callus pieces.

Regeneration: Regeneration of transgenic callus is accomplished by transferring the Bialaphos resistant callus to Regeneration Medium I and incubating 1 week at 25° C. in the dark. Subsequently matured somatic embryos are transferred to Regeneration Medium II in light and are maintained under these conditions for 4 to 6 weeks until germination is achieved.

FISH analysis is conducted as described in example 13, specific localization of the heterologous DNA to the singular rDNA array is observed in the events where multiple copies of the heterologous genes arise as a result of insertion into the rDNA array.

CONCLUSIONS

It is observed that multiple copies of the transgene that integrated have substantial similarity. Since the method of the present invention identifies the rDNA arrays for insertion and subsequent expression, it is believed that the heterologous DNA sequences are imparted with the same degree of sequence stability as the neighbouring rDNA genes. Results of Southern blots and PCR results in examples of the invention are evident of sequence similarity among repeated heterologous genes. Thus the genetic material introduced to plant germplasm will not be subject to instability.

It is also observed that the claimed method works independently of individual plant species, providing similar results will all plant species used to exemplify the method and hence is a method universal to all plant species.

It is also observed that the results of using the method in the present invention are consistent and reproducible among independently regenerated plants, whereas, transformation based on Agrobacterial or biolistic methods result in variable expression levels (See Gelvin et al. Microbiol Mol Bio Rev, 67: 16, 2003).

It is also observed that the methods of the present invention do not typically exhibit suppression of gene expression as a result of increased copy number. Gene silencing is prevalent in multiple-copy gene insertions using other gene systems (see Agrawal et al. Microbiol Mol Bio Rev, 67: 657, 2003; and Matzke and Matztke. Science, 301: 1060, 2003).

It is also observed that the transgene and the native rDNA array behave as a single locus, as indicated by FISH and other molecular methods.

It is further observed that the phenotype of the transformed plants of the invention when compared to non-transformed plants of the same genotype remains unchanged. Plants of the present invention are "normal" in phenotype, being of similar height and biomass as the non-transformed variety. In addition, seed size, number and silique filling are nominal, yet have greatly modified oil profiles. As discussed above, integration of heterologous DNA into the rDNA array so that it becomes a part of that array minimizes impact on the plant's normal metabolism, resulting in a stable, consistent engineered plant variety capable of accumulating valuable seed oil compositions.

The teachings of the present invention are not limited to the modification of seed oil content and/or composition. The methods may be used to introduce new genetic activities that relate to agronomic improvements, modification of plant carbohydrates, sugars and fiber, alteration of plant storage proteins or expression of genes that alter plant physiological processes or secondary metabolites. The process is universal and may be applied to various crops such as corn, soybean, cotton, Canola, cereal crops, vegetable crops, algae and the like.

TABLE 1

| Medium/Buffer/Solution | Compositions composition | | |
| --- | --- | --- | --- |
| Enzyme B2 (200 mL) | For 200 ml: | | |
| | Onzuka R10 (Yakult honsha 201091) | 2 g | |
| | Macerozyme R10 (Yakult honsha 202041) | 0.4 g | |
| | Sucrose (Anachemia 87688-380, Lot 601127) | 27.38 g | |
| | B5 B5 (Sigma G5893, Lot 46K2332) | 0.64 g | |
| | CaCl2•2H2O (EMscience, B10070-34, Lot 40337237) | 0.15 g | |
| | Mes (Sigma M2933, Lot 045K5456) | 0.117 g | |
| | Polyvinylpyrrolidone (Sigma P2307, 013K0101) | 1 g | |
| | NAA (0.5 mg/ml) (Agrisoma media log book #I, page 172) | 0.4 ml | 400 ul |
| | 2,4-D (0.5 mg/ml) (Agrisoma media log book #II, page 184) | 0.4 ml | 400 ul |
| | BA (0.5 mg/ml) (Agrisoma media log book #I, page 38) | 0.4 ml | 400 ul |
| | PH 6 | | |
| 17% B5 Wash 500 mL | B5 B5 (Sigma G5893, Lot 46K2332) | 1.6 g | |
| | CaCl2•2H2O (Sigma, C7902, Lot 056k00771) | 0.375 g | |
| | Sucrose (Anachemia 87688-380, Lot 601127) | 85.5 g | |
| | Mes (Sigma M2933, Lot 045k5456) | 0.295 g | |
| | PH 6 | | |
| | autoclave for 20 min. | | |
| WW5-2 Solution (2 L) | CaCl2•2H2O (Sigma c7902, Lot 056k00771) | 33.1 g | |
| | NaCl (Emsciene, SX 0420-3, Lot 44303) | 16.2 g | |
| | KCl (Sigma P-5405, Lot 082k0032) | 0.66 g | |
| | Glucose (Sigma G-8270, Lot 123k0095) | 1.62 g | |
| | Mes (Sigma M2933, Lot 045k5456) | 1.8 g | |
| | PH 6 | | |
| | Autoclave for 25 min. | | |
| WMMM Solution (100 ml) | MgCl2•6H2O (15 mM) (Emsciene 5980, Lot 0892b41) | 0.305 g | |
| | Mes (0.1%) (Sigma M2933, Lot 045k5456) | 0.1 g | |
| | Mannitol (0.5M) (Sigma M1902, Lot 054k01362) | 9.11 g | |
| | PH 5.8 | | |
| | Autoclave for 20 min. | | |
| Embed B1 Medium (400 ml) | MS Basal (Sigma M5519, lot 066K24372) | 1.76 g | |
| | Sucrose (Anachemia 87688-380, Lot 601127) | 13.6 g | |
| | Mes (Sigma M2933, Lot 045K5456) | 0.2 g | |
| | NAA (0.5 mg/ml) (Agrisoma media log book# I, page 172) | 800 ul | |
| | 2,4-D (0.5 mg/ml) (Agrisoma media Log book# II page 184) | 800 ul | |
| | BA (0.5 mg/ml) (Agrisoma media log book# I, page38) | 800 ul | |
| | PH 6 | | |
| | Autoclave 30 min. along with other media. | | |
| Proliferation B1 (1 L) | MS basal (Sigma M5519, Lot 066K24372) | 4.4 g | |
| | Sucrose (Anachemia 87688-380, Lot 601127) | 34 g | |
| | Mes (Sigma M2933, Lot 045K5456) | 0.5 g | |
| | NAA (0.5 mg/ml) (Agrisoma media log book I, page 172) | 2 ml | |
| | 2,4-D (0.5 mg/ml) (Agrisoma media log book II, page 184) | 2 ml | |
| | BA (0.5 mg/ml) (Agrisoma media log book I, page 38) | 2 ml | |
| | PH 6 | | |
| | Sea Plaque Agarose (Cambrex, 50100, Lot AG6410) | 7 g | |
| | Autoclave for 30 min. | | |
| | Add after autoclave: | | |
| | Carnbenicilin/cefotaxin (180 mg/ml) (Agrisoma media log book III, page 59) | | |
| | 560 ul/500 ml | | |

TABLE 1-continued

Compositions

| Medium/Buffer/Solution | composition | | |
|---|---|---|---|
| Regeneration B2 10PPT (2 L) | MS Basal (Sigma M5519, Lot 115k23271) | 8.8 g | |
| | Sucrose (Anachemia 87688-380, Lot 600303) | 60 g | |
| | AgNO3 (Sigma 209139, 05621AD) | 0.01 g | |
| | PVP (Sigma P2307, 013k0101) | 1 g | |
| | Mes (Sigma M2933, Lot 012k54391) | 1 g | |
| | NAA (0.5 mg/ml) (Agrisoma lab notebook# 23, page 58) | 0.2 mg | 400 ul |
| | 2iP (1 mg/ml) (Sigma, D7660, 66k2352) | 10 mg | 10 ml |
| | GA3 (5 mg/ml) (Sigma G7645-09k0811) | 0.0002 mg | 40 ul |
| | (Lab notebook #23, page 7) | | |
| | PH 5.8 | | |
| | Sea Plaque Agarose (Cambrex, 50100, Lot AG6284) | 14 g | |
| | Autoclave for 30 min. | | |
| | When lukewarm, add filter-sterilized L-PPT (20 mg/ml) | 250 ul/500 ml | |
| | When lukewarm, add filter-sterilized (180 mg/ml stock) | 280 ul/500 ml | |
| | 100 C./100 C. | | |
| OB5 rooting media | TBD | | |
| K3P-4 medium | Kao macro stock 10X | 100 ml | |
| 1 L | Kao micro 1000X | 1 ml | |
| | Kao vitamins 100X | 10 ml | |
| | Kao organic acids 500X | 2 ml | |
| | Glucose | 68.4 g | |
| | Mes (5 mM) | 1 g | |
| | Ficoll 400 (0.5%) | 5 g | |
| | CaCl2•2H2O | 400 mg | |
| | NAA (0.5 mg/ml stock) | 1 mg (2 ml) | |
| | 2,4-D (0.5 mg/ml) | 1 mg (2 ml) | |
| | BA (0.5 mg/ml) | 1 mg (2 ml) | |
| | Ph 6 | | |
| | + C/C 200C/C (180 mg/ml stock) | 560 ul/500 ml media | |
| | Filter-sterilize | | |
| | store@ 4° C. | | |
| PEG B2 solution | 40% PEG 4000 | 33.4 mls of 60% solution | |
| 50 mls | Mannitol (0.4M) | 3.64 g | |
| | Ca(NO3)2•4H2O (0.1M) | 1.18 g | |
| | Mes 0.1% | 0.5 g | |
| | pH6 + Filter-sterilize | | |
| B5 vitamins | myo-Inositol | 0.100 g/L | |
| (Gamborg et al. 1968) | Nicotinic acid | 0.001 g/L | |
| | Pyridoxine-HCl | 0.001 g/L | |
| | Thiamine-HCl | 0.010 g/L | |
| MS salts | Macronutrient Salts | | |
| (Murashige and Skoog 1962) | Ammonium Nitrate | 1.650000 g/L | |
| | Calcium Chloride Anhydrous | 0.332020 g/L | |
| | Magnesum Sulfate Anhydrous | 0.180700 g/L | |
| | Potassium Nitrate | 1.900000 g/L | |
| | Potassium Phosphate monobasic | 0.170000 g/L | |
| | Micronutrient salts | | |
| | Boric Acid | 0.006200 g/L | |
| | Cobalt Chloride-6$H_2$O | 0.000025 g/L | |
| | Cupric Sulfate Anhydrous | 0.000025 g/L | |
| | Ferrous Sulfate-7$H_2$O | 0.027800 g/L | |
| | Manganese Sulfate-$H_2$O | 0.016900 g/L | |
| | Molybdic Acid Sodium Salt-2$H_2$O | 0.000250 g/L | |
| | Na2-EDTA-2$H_2$O | 0.037260 g/L | |
| | Potassium Iodide | 0.000830 g/L | |
| | Zinc Sulfate-7$H_2$O | 0.008600 g/L | |
| MSD40 | MS salts, | | |
| (Finer and Nagasawa 1988) | B5 vitamins | | |
| | 6% (w:v) sucrose | | |
| | 40 mg/l 2,4-D | | |
| | 0.2% Gelrite, pH 5.8 | | |
| 10A40N medium | modified MS salts (Ammonium Nitrate and Pottasium Nitrate replaced by | | |
| (Finer and Nagasawa 1988) | 10 mM NH4NO3 and 30 mM KNO3) | | |
| | B5 vitamins | | |
| | 6% sucrose | | |
| | 5 mg/l 2,4-D | | |
| | 5 mM asparagine, pH 5.8 | | |
| OMSM6 medium | MS salts | | |
| | B5 vitamins | | |
| | 6% maltose | | |
| | 0.5% activated charcoal | | |
| | 0.2% Gelrite, pH 5.8) | | |

TABLE 1-continued

| Medium/Buffer/Solution | Compositions composition | |
|---|---|---|
| B5 Medium with sucrose, phytoagar (or gelrite (Gamborg et al, 1968) | Macronutrient Salts | |
| | Ammonium Sulfate | 0.13400 g/L |
| | Calcium Chloride Anhydrous | 0.113240 g/L |
| | Magnesium Sulfate Anhydrous | 0.122090 g/L |
| | Potassium Nitrate | 2.500000 g/L |
| | Micronutrient salts | |
| | Boric Acid | 0.003000 g/L |
| | Cobalt Chloride-6$H_2$O | 0.000025 g/L |
| | Cupric Sulfate Anhydrous | 0.000025 g/L |
| | Ferrous Sulfate-7$H_2$O | 0.027800 g/L |
| | Manganese Sulfate-$H_2$O | 0.010000 g/L |
| | Molybdic Acid Sodium Salt-2$H_2$O | 0.000250 g/L |
| | Na2-EDTA-2$H_2$O | 0.037300 g/L |
| | Potassium Iodide | 0.000750 g/L |
| | Zinc Sulfate-7$H_2$O | 0.002000 g/L |
| | Vitamins | |
| | myo-Inositol | 0.100 g/L |
| | Nicotinic acid | 0.001 g/L |
| | Pyridoxine-HCl | 0.001 g/L |
| | Thiamine-HCl | 0.010 g/L |
| | Other | |
| | Sucrose | 30.0 g/L |
| | Phytoagar (or Gelrite) | 6.0 g/L (or 2.0 g/L) |
| | pH 5.8 | |
| Chu's N6 salts and vitamins Chu et al. 1975 | Macronutrient Salts | |
| | Ammonium Sulfate | 0.463000 g/L |
| | Calcium Chloride Anhydrous | 0.125330 g/L |
| | Magnesium Sulfate Anhydrous | 0.090370 g/L |
| | Potassium Nitrate | 2.830000 g/L |
| | Potassium Phosphate monobasic | 0.400000 g/L |
| | Micronutrient salts | |
| | Boric Acid | 0.001600 g/L |
| | Ferrous Sulfate-7$H_2$O | 0.027850 g/L |
| | Manganese Sulfate-$H_2$O | 0.003330 g/L |
| | Na2-EDTA-2$H_2$O | 0.037250 g/L |
| | Potassium Iodide | 0.000800 g/L |
| | Zinc Sulfate-7$H_2$O | 0.001500 g/L |
| | Vitamins | |
| | Glycine | 0.002 g/L |
| | Nicotinic acid | 0.0005 g/L |
| | Pyridoxine-HCl | 0.0005 g/L |
| | Thiamine-HCl | 0.0010 g/L |
| Modified N6 salts and vitamins | N6 salts and vitamins supplemented with: 2% sucrose, 1 mg/L 2,4-D 25 mM proline 100 mg/L vitamin-free casamino acids 10 µM silver nitrate 0.6% Phytagar | |
| Modified N6-Mannitol | Modified N6 salts and vitamins supplemented with: 0.4M Mannitol | |
| Regeneration medium 1 | Modified N6 salts and vitamins supplemented with: 0.5 mg/l 2,4-D 10 mg/l benzyl adenine | |
| Regeneration medium 2 | 0.5 × N6 salts 1% sucrose | |

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

As used in this specification and the appended claims, the singular forms "a", "an" and "the" include plural reference unless the context clearly dictates otherwise. As used in this specification and the appended claims, the terms "comprise", "comprising", "comprises" and other forms of these terms are intended in the non-limiting inclusive sense, that is, to include particular recited elements or components without excluding any other element or component. Unless defined otherwise all technical and scientific terms used herein have the same meaning as commonly understood to one of ordinary skill in the art to which this invention belongs.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

The invention claimed is:

1. A method for producing a transgenic plant, comprising:
   (a) co-transforming plant cells with:
      i. a first nucleic acid, said first nucleic acid comprising a nucleotide sequence of at least contiguous 100 nucleotides, said nucleotide sequence possessing at least 50% sequence identity over its entire length to a native ribosomal DNA (rDNA) sequence of said plant cells; and
      ii. a second nucleic acid, said second nucleic acid comprising a coding sequence operably linked to one or more regulatory elements for directing expression of said coding sequence in said plant cells;
   thereby obtaining transgenic plant cells;
   (b) regenerating a plurality of transgenic plants from said transgenic plant cells; and
   (c) selecting from said plurality of transgenic plants a transgenic plant wherein said second nucleic acids is stably integrated at or adjacent to rDNA sequences and said second nucleic acid is amplified.

2. The method according to claim 1, wherein step (c) comprises selecting from said plurality of transgenic plants a transgenic plant wherein said first and second nucleic acids are stably integrated into or adjacent to native rDNA of said transgenic plant cells and wherein said first and second nucleic acids are amplified.

3. The method according to claim 1, wherein the first and second nucleic acids are on the same construct.

4. The method according to claim 1, wherein the first and second nucleic acids are on different constructs.

5. The method according to claim 1, wherein said second nucleic acid is amplified resulting in 2 to 60 copies of said second nucleic acid.

6. The method according to claim 1, wherein said first nucleic acid is amplified resulting in 2 to 60 copies of said first nucleic acid.

7. The method according to claim 1, wherein a plurality of said second nucleic acids integrate into or adjacent to the native rDNA of said plant cell in sufficiently close proximity to one another that they segregate together as a single genetic locus.

8. The method according to claim 7, wherein one or more of said first nucleic acids integrates into or adjacent to the native rDNA of said plant cell in sufficiently close proximity to said plurality of second nucleic acids that said first and second nucleic acids segregate together as a single genetic locus.

9. The method according to claim 1, wherein said coding sequence encodes a gene product associated with plant fatty acid metabolism, and wherein said selected transgenic plant has altered fatty acid content relative to a wild type of said plant.

10. The method according to claim 1, wherein said second nucleic acid comprises a site specific recombination sequence.

11. The method according to claim 1, wherein said first nucleic acid consists of or consists essentially of said nucleotide sequence possessing at least 50% sequence identity over its entire length to a native ribosomal DNA (rDNA) sequence of said plant cells.

12. A transgenic plant produced by the method according to claim 1, or a seed, organ, tissue, part or cell thereof comprising said nucleic acids, or a descendant of said plant, seed, organ, tissue, part or cell comprising said nucleic acids.

13. A method for producing oil, said method comprising extracting oil from a plant according to claim 12.

14. The method according to claim 13, wherein said oil is extracted from seeds of said plant.

15. A transgenic plant comprising a plurality of nucleic acids heterologous to said plant, each of said nucleic acid comprising a coding sequence operably linked to one or more regulatory elements for directing expression of said coding sequence in said plant, said nucleic acid being stably integrated at or adjacent to native rDNA of said plant, or a seed, organ, tissue, part or cell thereof comprising said nucleic acids, or a descendant of said plant, seed, organ, tissue, part or cell comprising said nucleic acids.

16. The transgenic plant according to claim 15, wherein a plurality of said heterologous nucleic acids are integrated at or adjacent to the native rDNA of said plant in sufficiently close proximity to one another that they segregate together as a single genetic locus.

17. The transgenic plant according to claim 15, wherein said coding sequence encodes a gene product associated with plant fatty acid metabolism, and wherein said transgenic plant has altered fatty acid content relative to a wild type of said plant.

18. The transgenic plant according to claim 15, wherein said heterologous nucleic acid is present in 2 to 60 copies integrated at or adjacent to native rDNA of said plant.

* * * * *